US006486301B1

(12) United States Patent
Ebner et al.

(10) Patent No.: US 6,486,301 B1
(45) Date of Patent: Nov. 26, 2002

(54) INTERLEUKIN-20

(75) Inventors: Reinhard Ebner, Gaithersburg, MD (US); Marianne Murphy, Richmond (GB); Steven M. Ruben, Olney, MD (US); Jing-Shan Hu, Sunnyvale, CA (US); D. Roxanne Duan, Bethesda, MD (US); Kimberly A. Florence, Rockville, MD (US); Craig A. Rosen, Laytonsville, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

(21) Appl. No.: 09/231,788

(22) Filed: Jan. 15, 1999

Related U.S. Application Data

(63) Continuation-in-part of application No. 09/115,832, filed on Jul. 15, 1998.

(60) Provisional application No. 60/052,870, filed on Jul. 16, 1997, provisional application No. 60/060,140, filed on Sep. 26, 1997, and provisional application No. 60/055,952, filed on Aug. 18, 1997.

(51) Int. Cl.[7] ....................... C07K 14/475; A61K 38/19

(52) U.S. Cl. ....................................... 530/351; 424/85.1

(58) Field of Search .......................... 530/351; 424/85.1

(56) References Cited

FOREIGN PATENT DOCUMENTS

| | | |
|---|---|---|
| WO | 9518826 | 7/1995 |
| WO | 9849310 | 11/1998 |
| WO | 9935267 | 7/1999 |

OTHER PUBLICATIONS

Yao et al., "Human IL–17: A Novel Cytokine Derived from T Cells," *J. Immunol.*, 155(12) : 5483–5486 (Dec. 15, 2000).

EMBL Accession No. Y08090 (Sep. 16, 1999) Wuechner, "H. sapiens FGFR3 gene, intron 7".

Shi et al., "A Novel Cytokine Receptor–Ligand Pair: Identification, molecular characterization and in vivo immunomodulatory activity," *J. Biol. Chem*, 275(23): 19167–19176 (Jun. 23, 2000).

Li et al. (2000) PNAS "*Cloning and characterization of IL–17B and IL–17C, two new members of the IL–17 cytokine family*," 97(2):773–778.

Genbank Accession No. AAF01318 (Jan. 13, 2000).

Genbank Accession No. AF184969 (Jan. 13, 2000).

Genbank Accession No. AAF01319 (Jan. 13, 2000).

Genbank Accession No. AA780147 (Feb. 5, 1998).

Genbank Accession No. AA033733 (Feb. 1, 1997).

Genbank Accession No. AA476704 ((Aug. 8, 1997).

Genbank Accession No. AA704834 (Dec. 24, 1997).

Genbank Accession No. AA960023 (May 8, 1998).

EST–STS, No. AA443286 (Jun. 3, 1997).

EST–STS, No. AA680405 (Dec. 19, 1997).

EST–STS, No. W74664 (Oct. 16, 1996).

EST–STS, No. AA044549 (Sep. 5, 1996).

EST–STS, No. W74558 (Oct. 16, 1996).

Hall, S. (1995) Science 270:915–916.

*Primary Examiner*—Yvonne Eyler
*Assistant Examiner*—Fozia Hamud
(74) *Attorney, Agent, or Firm*—Human Genome Sciences Inc.

(57) ABSTRACT

The present invention relates to a novel IL-20 protein which is a member of the cytokine polypeptide family. In particular, isolated nucleic acid molecules are provided encoding the human IL-20 protein. IL-20 polypeptides are also provided as are vectors, host cells and recombinant methods for producing the same. The invention further relates to screening methods for identifying agonists and antagonists of IL-20 activity. Also provided are diagnostic methods for detecting immune system-related disorders and therapeutic methods for treating immune system-related disorders.

18 Claims, 5 Drawing Sheets

SEQUENCE LISTING

```
<160> NUMBER OF SEQ ID NOS: 29

<210> SEQ ID NO 1
<211> LENGTH: 705
<212> TYPE: DNA
<213> ORGANISM: Homo sapiens
<220> FEATURE:
<221> NAME/KEY: CDS
<222> LOCATION: (45)..(584)
<220> FEATURE:
<221> NAME/KEY: sig_peptide
<222> LOCATION: (45)..(104)
<220> FEATURE:
<221> NAME/KEY: mat_peptide
<222> LOCATION: (105)..(584)

<400> SEQUENCE: 1

tccaggcggg cagcagctgc aggctgacct tgcagcttgg cgga atg gac tgg cct       56
                                                 Met Asp Trp Pro
                                                 -20

cac aac ctg ctg ttt ctt ctt acc att tcc atc ttc ctg ggg ctg ggc       104
His Asn Leu Leu Phe Leu Leu Thr Ile Ser Ile Phe Leu Gly Leu Gly
    -15                 -10                 -5                  -1

cag ccc agg agc ccc aaa agc aag agg aag ggg caa ggg cgg cct ggg       152
Gln Pro Arg Ser Pro Lys Ser Lys Arg Lys Gly Gln Gly Arg Pro Gly
  1               5                  10                  15

ccc ctg gcc cct ggc cct cac cag gtg cca ctg gac ctg gtg tca cgg       200
Pro Leu Ala Pro Gly Pro His Gln Val Pro Leu Asp Leu Val Ser Arg
            20                  25                  30

atg aaa ccg tat gcc cgc atg gag gag tat gag agg aac atc gag gag       248
Met Lys Pro Tyr Ala Arg Met Glu Glu Tyr Glu Arg Asn Ile Glu Glu
        35                  40                  45

atg gtg gcc cag ctg agg aac agc tca gag ctg gcc cag aga aag tgt       296
Met Val Ala Gln Leu Arg Asn Ser Ser Glu Leu Ala Gln Arg Lys Cys
    50                  55                  60

gag gtc aac ttg cag ctg tgg atg tcc aac aag agg agc ctg tct ccc       344
Glu Val Asn Leu Gln Leu Trp Met Ser Asn Lys Arg Ser Leu Ser Pro
 65                  70                  75                  80

tgg ggc tac agc atc aac cac gac ccc agc cgt atc ccc gtg gac ctg       392
Trp Gly Tyr Ser Ile Asn His Asp Pro Ser Arg Ile Pro Val Asp Leu
                 85                  90                  95
```

-continued

```
ccg gag gca cgg tgc ctg tgt ctg ggc tgt gtg aac ccc ttc acc atg     440
Pro Glu Ala Arg Cys Leu Cys Leu Gly Cys Val Asn Pro Phe Thr Met
        100                 105                 110

cag gag gac cgc agc atg gtg agc gtg ccg gtg ttc agc cag gtt cct     488
Gln Glu Asp Arg Ser Met Val Ser Val Pro Val Phe Ser Gln Val Pro
    115                 120                 125

gtg cgc cgc cgc ctc tgc ccg cca ccg ccc cgc aca ggg cct tgc cgc     536
Val Arg Arg Arg Leu Cys Pro Pro Pro Pro Arg Thr Gly Pro Cys Arg
130                 135                 140

cag cgc gca gtc atg gag acc atc gct gtg ggc tgc acc tgc atc ttc     584
Gln Arg Ala Val Met Glu Thr Ile Ala Val Gly Cys Thr Cys Ile Phe
145                 150                 155                 160

tgaattacct ggcccagaag ccaggccagc agcccgagac catcctcctt gcacctttgt    644

gccaagaaag gcctatgaaa agtaaacact gacttttgaa agcaaaaaaa aaaaaaaaaa    704

a                                                                    705
```

<210> SEQ ID NO 2
<211> LENGTH: 180
<212> TYPE: PRT
<213> ORGANISM: Homo sapiens

<400> SEQUENCE: 2

```
Met Asp Trp Pro His Asn Leu Leu Phe Leu Leu Thr Ile Ser Ile Phe
-20                 -15                 -10                  -5

Leu Gly Leu Gly Gln Pro Arg Ser Pro Lys Ser Lys Arg Lys Gly Gln
            -1   1                   5                  10

Gly Arg Pro Gly Pro Leu Ala Pro Gly Pro His Gln Val Pro Leu Asp
         15                  20                  25

Leu Val Ser Arg Met Lys Pro Tyr Ala Arg Met Glu Glu Tyr Glu Arg
     30                  35                  40

Asn Ile Glu Glu Met Val Ala Gln Leu Arg Asn Ser Ser Glu Leu Ala
 45                  50                  55                  60

Gln Arg Lys Cys Glu Val Asn Leu Gln Leu Trp Met Ser Asn Lys Arg
                 65                  70                  75

Ser Leu Ser Pro Trp Gly Tyr Ser Ile Asn His Asp Pro Ser Arg Ile
             80                  85                  90

Pro Val Asp Leu Pro Glu Ala Arg Cys Leu Cys Leu Gly Cys Val Asn
         95                 100                 105

Pro Phe Thr Met Gln Glu Asp Arg Ser Met Val Ser Val Pro Val Phe
     110                 115                 120

Ser Gln Val Pro Val Arg Arg Arg Leu Cys Pro Pro Pro Pro Arg Thr
125                 130                 135                 140

Gly Pro Cys Arg Gln Arg Ala Val Met Glu Thr Ile Ala Val Gly Cys
                145                 150                 155

Thr Cys Ile Phe
            160
```

<210> SEQ ID NO 3
<211> LENGTH: 155
<212> TYPE: PRT
<213> ORGANISM: Homo sapiens

<400> SEQUENCE: 3

```
Met Thr Pro Gly Lys Thr Ser Leu Val Ser Leu Leu Leu Leu Leu Ser
  1               5                  10                  15

Leu Glu Ala Ile Val Lys Ala Gly Ile Thr Ile Pro Arg Asn Pro Gly
             20                  25                  30
```

-continued

```
Cys Pro Asn Ser Glu Asp Lys Asn Phe Pro Arg Thr Val Met Val Asn
         35                  40                  45

Leu Asn Ile His Asn Arg Asn Thr Asn Thr Asn Pro Lys Arg Ser Ser
     50                  55                  60

Asp Tyr Tyr Asn Arg Ser Thr Ser Pro Trp Asn Leu His Arg Asn Glu
 65                  70                  75                  80

Asp Pro Glu Arg Tyr Pro Ser Val Ile Trp Glu Ala Lys Cys Arg His
                 85                  90                  95

Leu Gly Cys Ile Asn Ala Asp Gly Asn Val Asp Tyr His Met Asn Ser
            100                 105                 110

Val Pro Ile Gln Gln Glu Ile Leu Val Leu Arg Arg Glu Pro Pro His
        115                 120                 125

Cys Pro Asn Ser Phe Arg Leu Glu Lys Ile Leu Val Ser Val Gly Cys
    130                 135                 140

Thr Cys Val Thr Pro Ile Val His His Val Ala
145                 150                 155


<210> SEQ ID NO 4
<211> LENGTH: 498
<212> TYPE: DNA
<213> ORGANISM: Homo sapiens
<220> FEATURE:
<221> NAME/KEY: misc_feature
<222> LOCATION: (13)
<223> OTHER INFORMATION: n equals a, t, g or c
<220> FEATURE:
<221> NAME/KEY: misc_feature
<222> LOCATION: (58)
<223> OTHER INFORMATION: n equals a, t, g or c
<220> FEATURE:
<221> NAME/KEY: misc_feature
<222> LOCATION: (173)
<223> OTHER INFORMATION: n equals a, t, g or c
<220> FEATURE:
<221> NAME/KEY: misc_feature
<222> LOCATION: (179)
<223> OTHER INFORMATION: n equals a, t, g or c
<220> FEATURE:
<221> NAME/KEY: misc_feature
<222> LOCATION: (213)
<223> OTHER INFORMATION: n equals a, t, g or c
<220> FEATURE:
<221> NAME/KEY: misc_feature
<222> LOCATION: (288)
<223> OTHER INFORMATION: n equals a, t, g or c
<220> FEATURE:
<221> NAME/KEY: misc_feature
<222> LOCATION: (312)
<223> OTHER INFORMATION: n equals a, t, g or c
<220> FEATURE:
<221> NAME/KEY: misc_feature
<222> LOCATION: (323)
<223> OTHER INFORMATION: n equals a, t, g or c
<220> FEATURE:
<221> NAME/KEY: misc_feature
<222> LOCATION: (331)
<223> OTHER INFORMATION: n equals a, t, g or c
<220> FEATURE:
<221> NAME/KEY: misc_feature
<222> LOCATION: (337)
<223> OTHER INFORMATION: n equals a, t, g or c
<220> FEATURE:
<221> NAME/KEY: misc_feature
<222> LOCATION: (340)
<223> OTHER INFORMATION: n equals a, t, g or c
<220> FEATURE:
<221> NAME/KEY: misc_feature
<222> LOCATION: (348)
<223> OTHER INFORMATION: n equals a, t, g or c
<220> FEATURE:
```

-continued

<221> NAME/KEY: misc_feature
<222> LOCATION: (363)
<223> OTHER INFORMATION: n equals a, t, g or c
<220> FEATURE:
<221> NAME/KEY: misc_feature
<222> LOCATION: (365)
<223> OTHER INFORMATION: n equals a, t, g or c
<220> FEATURE:
<221> NAME/KEY: misc_feature
<222> LOCATION: (369)
<223> OTHER INFORMATION: n equals a, t, g or c
<220> FEATURE:
<221> NAME/KEY: misc_feature
<222> LOCATION: (375)
<223> OTHER INFORMATION: n equals a, t, g or c
<220> FEATURE:
<221> NAME/KEY: misc_feature
<222> LOCATION: (386)
<223> OTHER INFORMATION: n equals a, t, g or c
<220> FEATURE:
<221> NAME/KEY: misc_feature
<222> LOCATION: (391)
<223> OTHER INFORMATION: n equals a, t, g or c
<220> FEATURE:
<221> NAME/KEY: misc_feature
<222> LOCATION: (393)
<223> OTHER INFORMATION: n equals a, t, g or c
<220> FEATURE:
<221> NAME/KEY: misc_feature
<222> LOCATION: (395)
<223> OTHER INFORMATION: n equals a, t, g or c
<220> FEATURE:
<221> NAME/KEY: misc_feature
<222> LOCATION: (398)
<223> OTHER INFORMATION: n equals a, t, g or c
<220> FEATURE:
<221> NAME/KEY: misc_feature
<222> LOCATION: (403)
<223> OTHER INFORMATION: n equals a, t, g or c
<220> FEATURE:
<221> NAME/KEY: misc_feature
<222> LOCATION: (405)
<223> OTHER INFORMATION: n equals a, t, g or c
<220> FEATURE:
<221> NAME/KEY: misc_feature
<222> LOCATION: (407)
<223> OTHER INFORMATION: n equals a, t, g or c
<220> FEATURE:
<221> NAME/KEY: misc_feature
<222> LOCATION: (409)
<223> OTHER INFORMATION: n equals a, t, g or c
<220> FEATURE:
<221> NAME/KEY: misc_feature
<222> LOCATION: (413)
<223> OTHER INFORMATION: n equals a, t, g or c
<220> FEATURE:
<221> NAME/KEY: misc_feature
<222> LOCATION: (415)
<223> OTHER INFORMATION: n equals a, t, g or c
<220> FEATURE:
<221> NAME/KEY: misc_feature
<222> LOCATION: (420)
<223> OTHER INFORMATION: n equals a, t, g or c
<220> FEATURE:
<221> NAME/KEY: misc_feature
<222> LOCATION: (423)
<223> OTHER INFORMATION: n equals a, t, g or c
<220> FEATURE:
<221> NAME/KEY: misc_feature
<222> LOCATION: (428)
<223> OTHER INFORMATION: n equals a, t, g or c
<220> FEATURE:
<221> NAME/KEY: misc_feature
<222> LOCATION: (433)
<223> OTHER INFORMATION: n equals a, t, g or c
<220> FEATURE:
<221> NAME/KEY: misc_feature
<222> LOCATION: (435)
<223> OTHER INFORMATION: n equals a, t, g or c -continued
<220> FEATURE:
<221> NAME/KEY: misc_feature
<222> LOCATION: (440)
<223> OTHER INFORMATION: n equals a, t, g or c
<220> FEATURE:
<221> NAME/KEY: misc_feature
<222> LOCATION: (450)
<223> OTHER INFORMATION: n equals a, t, g or c
<220> FEATURE:
<221> NAME/KEY: misc_feature
<222> LOCATION: (452)
<223> OTHER INFORMATION: n equals a, t, g or c
<220> FEATURE:
<221> NAME/KEY: misc_feature
<222> LOCATION: (460)
<223> OTHER INFORMATION: n equals a, t, g or c
<220> FEATURE:
<221> NAME/KEY: misc_feature
<222> LOCATION: (465)
<223> OTHER INFORMATION: n equals a, t, g or c
<220> FEATURE:
<221> NAME/KEY: misc_feature
<222> LOCATION: (467)
<223> OTHER INFORMATION: n equals a, t, g or c
<220> FEATURE:
<221> NAME/KEY: misc_feature
<222> LOCATION: (470)
<223> OTHER INFORMATION: n equals a, t, g or c
<220> FEATURE:
<221> NAME/KEY: misc_feature
<222> LOCATION: (475)
<223> OTHER INFORMATION: n equals a, t, g or c
<220> FEATURE:
<221> NAME/KEY: misc_feature
<222> LOCATION: (490)
<223> OTHER INFORMATION: n equals a, t, g or c
<220> FEATURE:
<221> NAME/KEY: misc_feature
<222> LOCATION: (492)
<223> OTHER INFORMATION: n equals a, t, g or c

<400> SEQUENCE: 4
aattcggcac gantccaggc gggcagcagc tgcaggctga ccttgcagct tggcggantg 60
gactggcctc acaacctgct gtttcttctt accatttcca tcttcctggg gctgggccag 120
cccaggagcc ccaaaagcaa gaggaagggg caagggcggc ctgggcccct ggncctggnc 180
ctcaccaggt gccactggac ctggtgtcac ggntgaaacc gtatgcccgc atggaggagt 240
atgagaggaa catcgaggag atggtggccc agctgaggaa cagctcanag ctgggcccag 300
agaaagtttg angntcaact ttncaagctt ntgggtnttn caacaagnag gtagcctgtt 360
ttncntggng gttannagta tgaatncaag nancncangc gtnnntncng ttngnncttn 420
tcnggagnac gtntnncttn tttttttggn tnnttgaacn ctttnanatn gtagnnggac 480
ctagaattgn tnagggtg 498

<210> SEQ ID NO 5
<211> LENGTH: 42
<212> TYPE: DNA
<213> ORGANISM: Homo sapiens

<400> SEQUENCE: 5
gatcgcggat cccagcccag gagccccaaa agcaagagga ag 42

<210> SEQ ID NO 6
<211> LENGTH: 47
<212> TYPE: DNA
<213> ORGANISM: Homo sapiens

<400> SEQUENCE: 6

-continued

```
gatcgcggta cccaggttta tcagaagatg caggtgcagc ccacagc                  47


<210> SEQ ID NO 7
<211> LENGTH: 53
<212> TYPE: DNA
<213> ORGANISM: Homo sapiens

<400> SEQUENCE: 7

gatcgcggat ccgccatcat ggactggcct cacaacctgc tgtttcttct tac           53


<210> SEQ ID NO 8
<211> LENGTH: 47
<212> TYPE: DNA
<213> ORGANISM: Homo sapiens

<400> SEQUENCE: 8

gatcgcggta cccaggttta tcagaagatg caggtgcagc ccacagc                  47


<210> SEQ ID NO 9
<211> LENGTH: 53
<212> TYPE: DNA
<213> ORGANISM: Homo sapiens

<400> SEQUENCE: 9

gatcgcggta ccgccatcat ggactggcct cacaacctgc tgtttcttct tac           53


<210> SEQ ID NO 10
<211> LENGTH: 47
<212> TYPE: DNA
<213> ORGANISM: Homo sapiens

<400> SEQUENCE: 10

gatcgcggat cccaggttta tcagaagatg caggtgcagc ccacagc                  47


<210> SEQ ID NO 11
<211> LENGTH: 87
<212> TYPE: PRT
<213> ORGANISM: Homo sapiens

<400> SEQUENCE: 11

Ala Arg Val Asp Thr Asp Glu Asp Arg Tyr Pro Gln Lys Leu Ala Phe
  1               5                  10                  15

Ala Glu Cys Leu Cys Arg Gly Cys Ile Asp Ala Arg Thr Gly Arg Glu
             20                  25                  30

Thr Ala Ala Leu Asn Ser Val Arg Leu Leu Gln Ser Leu Leu Val Leu
         35                  40                  45

Arg Arg Arg Pro Cys Ser Arg Asp Gly Ser Gly Leu Pro Thr Pro Gly
     50                  55                  60

Ala Phe Ala Phe His Thr Glu Phe Ile His Val Pro Val Gly Cys Thr
 65                  70                  75                  80

Cys Val Leu Pro Arg Ser Val
                 85


<210> SEQ ID NO 12
<211> LENGTH: 160
<212> TYPE: PRT
<213> ORGANISM: Homo sapiens

<400> SEQUENCE: 12

Asn Ser Ala Arg Ala Arg Ala Val Leu Ser Ala Phe His His Thr Leu
  1               5                  10                  15
```

-continued

```
Gln Leu Gly Pro Arg Glu Gln Ala Arg Asn Ala Ser Cys Pro Ala Gly
            20                  25                  30

Gly Arg Pro Ala Asp Arg Arg Phe Arg Pro Pro Thr Asn Leu Arg Ser
        35                  40                  45

Val Ser Pro Trp Ala Tyr Arg Ile Ser Tyr Asp Pro Ala Arg Tyr Pro
    50                  55                  60

Arg Tyr Leu Pro Glu Ala Tyr Cys Leu Cys Arg Gly Cys Leu Thr Gly
65                  70                  75                  80

Leu Phe Gly Glu Glu Asp Val Arg Phe Arg Ser Ala Pro Val Tyr Met
                85                  90                  95

Pro Thr Val Val Leu Arg Arg Thr Pro Ala Cys Ala Gly Gly Arg Ser
            100                 105                 110

Val Tyr Thr Glu Ala Tyr Val Thr Ile Pro Val Gly Cys Thr Cys Val
        115                 120                 125

Pro Glu Pro Glu Lys Asp Ala Asp Ser Ile Asn Ser Ser Ile Asp Lys
    130                 135                 140

Gln Gly Ala Lys Leu Leu Leu Gly Pro Asn Asp Ala Pro Ala Gly Pro
145                 150                 155                 160


<210> SEQ ID NO 13
<211> LENGTH: 158
<212> TYPE: PRT
<213> ORGANISM: Mus musculus

<400> SEQUENCE: 13

Met Ser Pro Gly Arg Ala Ser Ser Val Ser Leu Met Leu Leu Leu Leu
  1               5                  10                  15

Leu Ser Leu Ala Ala Thr Val Lys Ala Ala Ala Ile Ile Pro Gln Ser
            20                  25                  30

Ser Ala Cys Pro Asn Thr Glu Ala Lys Asp Phe Leu Gln Asn Val Lys
        35                  40                  45

Val Asn Leu Lys Val Phe Asn Ser Leu Gly Ala Lys Val Ser Ser Arg
    50                  55                  60

Arg Pro Ser Asp Tyr Leu Asn Arg Ser Thr Ser Pro Trp Thr Leu His
65                  70                  75                  80

Arg Asn Glu Asp Pro Asp Arg Tyr Pro Ser Val Ile Trp Glu Ala Gln
                85                  90                  95

Cys Arg His Gln Arg Cys Val Asn Ala Glu Gly Lys Leu Asp His His
            100                 105                 110

Met Asn Ser Val Leu Ile Gln Gln Glu Ile Leu Val Leu Lys Arg Glu
        115                 120                 125

Pro Glu Ser Cys Pro Phe Thr Phe Arg Val Glu Lys Met Leu Val Gly
    130                 135                 140

Val Gly Cys Thr Cys Val Ala Ser Ile Val Arg Gln Ala Ala
145                 150                 155


<210> SEQ ID NO 14
<211> LENGTH: 151
<212> TYPE: PRT
<213> ORGANISM: Homo sapiens

<400> SEQUENCE: 14

Met Thr Phe Arg Met Thr Ser Leu Val Leu Leu Leu Leu Leu Ser Ile
  1               5                  10                  15

Asp Cys Ile Val Lys Ser Glu Ile Thr Ser Ala Gln Thr Pro Arg Cys
            20                  25                  30
```

-continued

```
Leu Ala Ala Asn Asn Ser Phe Pro Arg Ser Val Met Val Thr Leu Ser
        35                  40                  45

Ile Arg Asn Trp Asn Thr Ser Ser Lys Arg Ala Ser Asp Tyr Tyr Asn
    50                  55                  60

Arg Ser Thr Ser Pro Trp Thr Leu His Arg Asn Glu Asp Gln Asp Arg
65                  70                  75                  80

Tyr Pro Ser Val Ile Trp Glu Ala Lys Cys Arg Tyr Leu Gly Cys Val
                85                  90                  95

Asn Ala Asp Gly Asn Val Asp Tyr His Met Asn Ser Val Pro Ile Gln
            100                 105                 110

Gln Glu Ile Leu Val Val Arg Lys Gly His Gln Pro Cys Pro Asn Ser
        115                 120                 125

Phe Arg Leu Glu Lys Met Leu Val Thr Val Gly Cys Thr Cys Val Thr
    130                 135                 140

Pro Ile Val His Asn Val Asp
145                 150


<210> SEQ ID NO 15
<211> LENGTH: 126
<212> TYPE: PRT
<213> ORGANISM: Homo sapiens

<400> SEQUENCE: 15

Met Asp Trp Pro His Asn Leu Leu Phe Leu Leu Thr Ile Ser Ile Phe
  1               5                  10                  15

Leu Gly Leu Gly Gln Pro Arg Ser Pro Lys Ser Lys Arg Lys Gly Gln
            20                  25                  30

Gly Arg Pro Gly Pro Leu Ala Pro Gly Pro His Gln Val Pro Leu Asp
        35                  40                  45

Leu Val Ser Arg Met Lys Pro Tyr Ala Arg Met Glu Glu Tyr Glu Arg
    50                  55                  60

Asn Ile Glu Glu Met Val Ala Gln Leu Arg Asn Ser Ser Glu Leu Ala
65                  70                  75                  80

Gln Arg Lys Cys Glu Val Asn Leu Gln Leu Trp Met Ser Asn Lys Arg
                85                  90                  95

Ser Leu Ser Pro Trp Gly Tyr Ser Ile Asn His Asp Pro Ser Arg Ile
            100                 105                 110

Pro Val Asp Leu Pro Glu His Gly Ala Cys Val Trp Ala Val
        115                 120                 125


<210> SEQ ID NO 16
<211> LENGTH: 733
<212> TYPE: DNA
<213> ORGANISM: Homo sapiens

<400> SEQUENCE: 16

gggatccgga gcccaaatct tctgacaaaa ctcacacatg cccaccgtgc ccagcacctg      60

aattcgaggg tgcaccgtca gtcttcctct tcccccaaaa acccaaggac accctcatga     120

tctcccggac tcctgaggtc acatgcgtgg tggtggacgt aagccacgaa gaccctgagg     180

tcaagttcaa ctggtacgtg gacggcgtgg aggtgcataa tgccaagaca aagccgcggg     240

aggagcagta caacagcacg taccgtgtgg tcagcgtcct caccgtcctg caccaggact     300

ggctgaatgg caaggagtac aagtgcaagg tctccaacaa agccctccca acccccatcg     360

agaaaaccat ctccaaagcc aaagggcagc cccgagaacc acaggtgtac accctgcccc     420

catcccggga tgagctgacc aagaaccagg tcagcctgac ctgcctggtc aaaggcttct     480
```

-continued atccaagcga catcgccgtg gagtgggaga gcaatgggca gccggagaac aactacaaga 540
ccacgcctcc cgtgctggac tccgacggct ccttcttcct ctacagcaag ctcaccgtgg 600
acaagagcag gtggcagcag gggaacgtct tctcatgctc cgtgatgcat gaggctctgc 660
acaaccacta cacgcagaag agcctctccc tgtctccggg taaatgagtg cgacggccgc 720
gactctagag gat 733

<210> SEQ ID NO 17
<211> LENGTH: 5
<212> TYPE: PRT
<213> ORGANISM: Homo sapiens

<400> SEQUENCE: 17

Trp Ser Xaa Trp Ser
1 5

<210> SEQ ID NO 18
<211> LENGTH: 86
<212> TYPE: DNA
<213> ORGANISM: Homo sapiens

<400> SEQUENCE: 18
gcgcctcgag atttccccga aatctagatt tccccgaaat gatttccccg aaatgatttc 60
cccgaaatat ctgccatctc aattag 86

<210> SEQ ID NO 19
<211> LENGTH: 27
<212> TYPE: DNA
<213> ORGANISM: Homo sapiens

<400> SEQUENCE: 19
gcggcaagct ttttgcaaag cctaggc 27

<210> SEQ ID NO 20
<211> LENGTH: 271
<212> TYPE: DNA
<213> ORGANISM: Homo sapiens

<400> SEQUENCE: 20
ctcgagattt ccccgaaatc tagatttccc cgaaatgatt tccccgaaat gatttccccg 60
aaatatctgc catctcaatt agtcagcaac catagtcccg cccctaactc cgcccatccc 120
gcccctaact ccgcccagtt ccgcccattc tccgccccat ggctgactaa ttttttttat 180
ttatgcagag gccgaggccg cctcggcctc tgagctattc cagaagtagt gaggaggctt 240
ttttggaggc ctaggctttt gcaaaaagct t 271

<210> SEQ ID NO 21
<211> LENGTH: 32
<212> TYPE: DNA
<213> ORGANISM: Homo sapiens

<400> SEQUENCE: 21
gcgctcgagg gatgacagcg atagaacccc gg 32

<210> SEQ ID NO 22
<211> LENGTH: 31
<212> TYPE: DNA
<213> ORGANISM: Homo sapiens

<400> SEQUENCE: 22

-continued

```
gcgaagcttc gcgactcccc ggatccgcct c                                31


<210> SEQ ID NO 23
<211> LENGTH: 12
<212> TYPE: DNA
<213> ORGANISM: Homo sapiens

<400> SEQUENCE: 23

ggggactttc cc                                                     12


<210> SEQ ID NO 24
<211> LENGTH: 73
<212> TYPE: DNA
<213> ORGANISM: Homo sapiens

<400> SEQUENCE: 24

gcggcctcga ggggactttc ccggggactt tccggggact ttccgggact ttccatcctg  60

ccatctcaat tag                                                     73


<210> SEQ ID NO 25
<211> LENGTH: 27
<212> TYPE: DNA
<213> ORGANISM: Homo sapiens

<400> SEQUENCE: 25

gcggcaagct ttttgcaaag cctaggc                                      27


<210> SEQ ID NO 26
<211> LENGTH: 256
<212> TYPE: DNA
<213> ORGANISM: Homo sapiens

<400> SEQUENCE: 26

ctcgagggga ctttcccggg gactttccgg ggactttccg ggactttcca tctgccatct  60

caattagtca gcaaccatag tcccgcccct aactccgccc atcccgcccc taactccgcc 120

cagttccgcc cattctccgc cccatggctg actaattttt tttatttatg cagaggccga 180

ggccgcctcg gcctctgagc tattccagaa gtagtgagga ggcttttttg gaggcctagg 240

cttttgcaaa aagctt                                                 256


<210> SEQ ID NO 27
<211> LENGTH: 130
<212> TYPE: PRT
<213> ORGANISM: Homo sapiens

<400> SEQUENCE: 27

Ser Arg Met Lys Pro Tyr Ala Arg Met Glu Glu Tyr Glu Arg Asn Ile
  1               5                  10                  15

Glu Glu Met Val Ala Gln Leu Arg Asn Ser Ser Glu Leu Ala Gln Arg
             20                  25                  30

Lys Cys Glu Val Asn Leu Gln Leu Trp Met Ser Asn Lys Arg Ser Leu
         35                  40                  45

Ser Pro Trp Gly Tyr Ser Ile Asn His Asp Pro Ser Arg Ile Pro Val
     50                  55                  60

Asp Leu Pro Glu Ala Arg Cys Leu Cys Leu Gly Cys Val Asn Pro Phe
 65                  70                  75                  80

Thr Met Gln Glu Asp Arg Ser Met Val Ser Val Pro Val Phe Ser Gln
                 85                  90                  95
```

-continued

```
Val Pro Val Arg Arg Arg Leu Cys Pro Pro Pro Pro Arg Thr Gly Pro
            100                 105                 110

Cys Arg Gln Arg Ala Val Met Glu Thr Ile Ala Val Gly Cys Thr Cys
        115                 120                 125

Ile Phe
    130


<210> SEQ ID NO 28
<211> LENGTH: 723
<212> TYPE: DNA
<213> ORGANISM: Homo sapiens

<400> SEQUENCE: 28

gaattcggca cgagtccagg cgggcagcag ctgcaggctg accttgcagc ttggcggaat     60

ggactggcct cacaacctgc tgtttcttct taccatttcc atcttcctgg ggctgggcca    120

gcccaggagc cccaaaagca agaggaaggg gcaagggcgg cctgggcccc tggcccctgg    180

ccctcaccag gtgccactgg acctggtgtc acggatgaaa ccgtatgccc gcatggagga    240

gtatgagagg aacatcgagg agatggtggc ccagctgagg aacagctcag agctggccca    300

gagaaagtgt gaggtcaact tgcagctgtg gatgtccaac aagaggagcc tgtctccctg    360

gggctacagc atcaaccacg accccagccg tatccccgtg gacctgccgg agcacggtgc    420

ctgtgtctgg gctgtgtgaa ccccttcacc atgcaggagg accgcagcat ggtgagcgtg    480

ccggtgttca gccaggttcc tgtgcgccgc cgcctctgcc cgccaccgcc ccgcacaggg    540

ccttgccgcc agcgcgcagt catggagacc atcgctgtgg gctgcacctg catcttctga    600

attacctggc ccagaagcca ggccagcagc ccgagaccat cctccttgca cctttgtgcc    660

aagaaaggcc tatgaaaagt aaacactgac ttttgaaagc aaaaaaaaaa aaaaaaaact    720

cga                                                                  723


<210> SEQ ID NO 29
<211> LENGTH: 723
<212> TYPE: DNA
<213> ORGANISM: Homo sapiens

<400> SEQUENCE: 29

tcgagttttt tttttttttt tttgctttca aaagtcagtg tttacttttc ataggccttt     60

cttggcacaa aggtgcaagg aggatggtct cgggctgctg gcctggcttc tgggccaggt    120

aattcagaag atgcaggtgc agcccacagc gatggtctcc atgactgcgc gctggcggca    180

aggccctgtg cggggcggtg gcgggcagag gcggcggcgc acaggaacct ggctgaacac    240

cggcacgctc accatgctgc ggtcctcctg catggtgaag gggttcacac agcccagaca    300

caggcaccgt gctccggcag gtccacgggg atacggctgg ggtcgtggtt gatgctgtag    360

ccccagggag acaggctcct cttgttggac atccacagct gcaagttgac ctcacacttt    420

ctctgggcca gctctgagct gttcctcagc tgggccacca tctcctcgat gttcctctca    480

tactcctcca tgcgggcata cggtttcatc cgtgacacca ggtccagtgg cacctggtga    540

gggccagggg ccaggggccc aggccgccct tgccccttcc tcttgctttt ggggctcctg    600

ggctggccca gccccaggaa gatggaaatg gtaagaagaa acagcaggtt gtgaggccag    660

tccattccgc caagctgcaa ggtcagcctg cagctgctgc ccgcctggac tcgtgccgaa    720

ttc                                                                  723
```

Interleukin-20

```
  1              TCCAGGCGGGCAGCAGCTGCAGGCTGACCTTGCAGCTTGGCGGAA   45
  1                                                          M   1

 46 TGGACTGGCCTCACAACCTGCTGTTTCTTCTTACCATTTCCATCTTCCTGGGGCTGGGCC 105
  2  D  W  P  H  N  L  L  F  L  L  T  I  S  I  F  L  G  L  G  Q   21
           *     *
106 AGCCCAGGAGCCCCAAAAGCAAGAGGAAGGGGCAAGGGCGGCCTGGGCCCCTGGCCCCTG 165
 22  P  R  S  P  K  S  K  R  K  G  Q  G  R  P  G  P  L  A  P  G   41

166 GCCCTCACCAGGTGCCACTGGACCTGGTGTCACGGATGAAACCGTATGCCCGCATGGAGG 225
 42  P  H  Q  V  P  L  D  L  V  S  R  M  K  P  Y  A  R  M  E  E   61
                                           #
226 AGTATGAGAGGAACATCGAGGAGATGGTGGCCCAGCTGAGGAACAGCTCAGAGCTGGCCC 285
 62  Y  E  R  N  I  E  E  M  V  A  Q  L  R  N  S  S  E  L  A  Q   81
                                        *
286 AGAGAAAGTGTGAGGTCAACTTGCAGCTGTGGATGTCCAACAAGAGGAGCCTGTCTCCCT 345
 82  R  K  C  E  V  N  L  Q  L  W  M  S  N  K  R  S  L  S  P  W  101
                      CD-I                                 CD-II
346 GGGGCTACAGCATCAACCACGACCCCAGCCGTATCCCCGTGGACCTGCCGGAGGCACGGT 405
102  G  Y  S  I  N  H  D  P  S  R  I  P  V  D  L  P  E  A  R  C  121
         CD-II                 *
406 GCCTGTGTCTGGGCTGTGTGAACCCCTTCACCATGCAGGAGGACCGCAGCATGGTGAGCG 465
122  L  C  L  G  C  V  N  P  F  T  M  Q  E  D  R  S  M  V  S  V  141
                         CD-III
466 TGCCGGTGTTCAGCCAGGTTCCTGTGCGCCGCCGCCTCTGCCCGCCACCGCCCCGCACAG 525
142  P  V  F  S  Q  V  P  V  R  R  R  L  C  P  P  P  P  R  T  G  161
                                             CD-IV
526 GGCCTTGCCGCCAGCGCGCAGTCATGGAGACCATCGCTGTGGGCTGCACCTGCATCTTCT 585
162  P  C  R  Q  R  A  V  M  E  T  I  A  V  G  C  T  C  I  F  *  180

586 GAATTACCTGGCCCAGAAGCCAGGCCAGCAGCCCGAGACCATCCTCCTTGCACCTTTGTG 645

646 CCAAGAAAGGCCTATGAAAAGTAAACACTGACTTTTGAAAGCAAAAAAAAAAAAAAAAAA 705
```

```
                    .         .         .         .         .
  1 MDWPHNLLFLLTISIFL..GLGQPRSPKSKRKGQGRPGPLAPGPHQVPLD 48
    ...   .||:||.:. ::   |:.  ||.| :...::
  5 KTSLVSLLLLLSLEAIVKAGITIPRNPGCPNSED................ 38

                    .         .         .         .         .
 49 LVSRMKPYARMEEYERNIEEMVAQLRNSSELAQRKCEVNLQLWMSNKRSL 98
         | ::|    : ||.:     ||... :.|.::          .||
 39 .....KNFPRTVMVNLNIHN.....RNTNTNPKRSSDY.......YNRST 71

                    .         .         .         .         .
 99 SPWGYSINHDPSRIPVDLPEARCLCLGCVNPFTMQEDRSMVSVPVFSQVP 148
    |||..  |.||.|.|  : ||:|  |||:|: . . |  | |||:  ::
 72 SPWNLHRNEDPERYPSVIWEAKCRHLGCINA.DGNVDYHMNSVPIQQEIL 120

                    .         .         .
149 VRRRLCPPPPRTGPCRQRAVMETIAVGCTCI 179
    | ||  .||. ... |   ::  :.|||||:
121 VLRR..EPPHCPNSFRLEKIL..VSVGCTCV 147
```

FIG. 2

```
122 LRREP----PHCP--NSFRLEKILVSVGCTCVTPIVHHVA        IL-17.aa
125 LKREP----ESCP--FTFRVEKMLVGVGCTCVASIVRQAA        mIL-17.aa
118 VRKGH----QPCP--NSFRLEKMLVTVGCTCVTPIVHNVD        vIL-17.aa
149 VRRRLCPPPRTGPCRQ--RAVMETIAVGCTCI-               IL20.aa
 48 LRRRPCSRDGSGLPTPGAFAFHTEFIHVPVGCTCV-            IL-21.aa
101 LRRTPACAGGRSV----YTEAYVTIPVGCTCVPEPEKDADSINSSID IL-22.aa

155 --------F            IL-17.aa
158 --------             mIL-17.aa
151 --------             vIL-17.aa
180 --------             IL20.aa
 83 ----LPRSV            IL-21.aa
144 KQGAKLLLGPNDAPAGP    IL-22.aa
```

INTERLEUKIN-20

This application is a continuation-in-part of copending U.S. application Ser. No. 09/115,832, filed on Jul. 15, 1998, which, in turn, claims benefit under 35 U.S.C. §119(e) of the filing date of U.S. Provisional Application Ser. No. 60/052,870, filed on Jul. 16, 1997, U.S. Provisional Applicaton Ser. No. 60/060,140, filed on Sep. 26, 1997, and U. S. Provisional Application Ser. No. 60/055,952 filed Aug. 18, 1997. Each of these four U.S. Patent Applications are hereby incorporated herein by reference in its entirety.

FIELD OF THE INVENTION

The present invention relates to a novel human gene encoding a polypeptide which is a novel human cytokine. More specifically, isolated nucleic acid molecules are provided encoding a human polypeptide named Interleukin 20, hereinafter referred to as "IL-20". IL-20 polypeptides are also provided, as are vectors, host cells and recombinant methods for producing the same. Also provided are diagnostic methods for detecting disorders related to the immune system, and therapeutic methods for treating such disorders.

The invention further relates to screening methods for identifying agonists and antagonists of IL-20 activity.

BACKGROUND OF THE INVENTION

Cytokines typically exert their respective biochemical and physiological effects by binding to specific receptor molecules. Receptor binding will then stimulate specific signal transduction pathways (Kishimoto, T., et al., *Cell* 76:253–262 (1994). The specific interactions of cytokines with their receptors are often the primary regulators of a wide variety of cellular processes including activation, proliferation, and differentiation (Arai, K.-I, et al., *Ann. Rev. Biochem.* 59:783–836 (1990); Paul, W. E. and Seder, R. A., *Cell* 76:241–251 (1994)).

Human interleukin (IL)-17 was only recently identified. IL-17 is a 155 amino acid polypetide which was molecularly cloned from a CD4+ T-cell cDNA library (Yao, Z., et al., *J. Immunol.* 155:5483–5486 (1995)). The IL-17 polypeptide contains an N-terminal signal peptide and contains approximately 72% identity at the amino acid level with a T-cell trophic herpesvirus saimiri (HVS) gene designated HVS13. High levels of IL-17 are secreted from CD4-positive primary peripheral blood leukocytes (PBL) upon stimulation (Yao, Z., et al., *Immunity* 3:811–821 (1995)). Treatment of fibroblasts with IL-17, HVS13, or another murine homologue, designated CTLA8, activate signal transduction pathways and result in the stimulation of the NF-κB transcription factor family, the secretion of IL-6, and the costimulation of T-cell proliferation (Yao, Z., et al., *Immunity* 3:811–821 (1995)).

An HVS13-Fc fusion protein was used to isolate a murine IL-17 receptor molecule which does not appear to belong to any of the previously described cytokine receptor families (Yao, Z., et al., *Immunity* 3:811–821 (1995)). The murine IL-17 receptor (mIL-17R) is predicted to encode a type I transmembrane protein of 864 amino acids with an apparent molecular mass of 97.8 kDa. mIL-17R is predicted to possess an N-terminal signal peptide with a cleavage site between alanine-31 and serine-32. The molecule also contains a 291 amino acid extracellular domain, a 21 amino acid transmembrane domain, and a 521 amino acid cytoplasmic tail. A soluble recombinant IL-17R molecule consisting of 323 amino acids of the extracellular domain of IL-17R fused to the Fc portion of human immunoglobulin IgG1 was able to significantly inhibit IL-17-induced IL-6 production by murine NIH-3T3 cells (supra).

Interestingly, the expression of the IL-17 gene is highly restricted. It is typically observed primarily in activated T-lymphocyte memory cells (Broxmeyer, H. *J. Exp. Med.* 183:2411–2415 (1996); Fossiez, F., et al., *J. Exp. Med.* 183:2593–2603 (1996)). Conversely, the IL-17 receptor appears to be expressed in a large number of cells and tissues (Rouvier, E., et al., *J. Immunol.* 150:5445–5456 (1993); Yao, Z., et al., *J. Immunol.* 155:5483–5486 (1995)). It remains to be seen, however, if IL-17 itself can play an autocrine role in the expression of IL-17. IL-17 has been implicated as a causitive agent in the expression of IL-6, IL-8, G-CSF, Prostaglandin E ($PGE_2$), and intracellular adhesion molecule (ICAM)-1 (Fossiez, F., supra; Yao, Z., et al., *Immunity* 3:811–821 (1995)). Each of these molecules possesses highly relevent and potentially therapeutically valuable properties. For instance, IL-6 is involved in the regulation of hematopoietic stem and progenitor cell growth and expansion (Ikebuchi, K., et al., *Proc. Natl. Acad. Sci. USA* 84:9035–9039 (1987); Gentile, P. and Broxmeyer, H. E. *Ann. N.Y. Acad. Sci. USA* 628:74–83 (1991)). IL-8 exhibits a myelosuppressive activity for stem cells and immature subsets of myeloid progenitors (Broxmeyer, H. E., et al., *Ann. Hematol.* 71:235–246 (1995); Daly, T. J., et al., *J. Biol. Chem.* 270:23282–23292 (1995)). G-CSF acts both early and late to activate and stimulate hematopoiesis in general, and more specifically on neutrophil hematopoiesis, while $PGE_2$ enhances erythropoiesis, suppresses lymphopoiesis and myelopoiesis in general, and strongly suppresses monocytopoiesis (Broxmeyer, H. E. *Amer. J. Ped. Hematol./Oncol.* 14:22–30 (1992); Broxmeyer, H. E. and Williams, D. E. *CRC Crit. Rev. Oncol./Hematol.* 8:173–226 (1988)).

Thus, there is a need for polypeptides that function as immunoregulatory molecules and, thereby, function in the transfer of an extracelluIlar signal ultimately to the nucleus of the cell, since disturbances of such regulation may be involved in disorders relating to cellular activation, hemostasis, angiogenesis, tumor metastasis, cellular migration and ovulation, as well as neurogenesis. Therefore, there is a need for identification and characterization of such human polypeptides which can play a role in detecting, preventing, ameliorating or correcting such disorders.

SUMMARY OF THE INVENTION

The present invention provides isolated nucleic acid molecules comprising a polynucleotide encoding at least a portion of the IL-20 polypeptide having the complete amino acid sequence shown in SEQ ID NO:2 or the complete amino acid sequence encoded by the cDNA clone deposited as plasmid DNA as ATCC Deposit Number 209232 on Aug. 29, 1997. The nucleotide sequence determined by sequencing the deposited IL-20 clone, which is shown in FIG. 1 (SEQ ID NO:1), contains an open reading frame encoding a complete polypeptide of 180 amino acid residues, including an initiation codon encoding an N-terminal methionine at nucleotide positions 45–47, and a predicted molecular weight of about 20.4 kDa. Nucleic acid molecules of the invention include those encoding the complete amino acid sequence excepting the N-terminal methionine shown in SEQ ID NO:2, or the complete amino acid sequence excepting the N-terminal methionine encoded by the cDNA clone in ATCC Deposit Number 209232, which molecules also can encode additional amino acids fused to the N-terminus of the IL-20 amino acid sequence.

The present invention also provides isolated nucleic acid molecules comprising a polynucleotide encoding at least a portion of the IL-20 polypeptide having the complete amino acid sequence shown in SEQ ID NO:15 or the complete amino acid sequence encoded by the cDNA clone deposited in a pool of 50 distinct plasmid DNA molecules as ATCC Deposit Number 209138 on Jul. 3, 1997. The sense and antisense nucleotide sequences determined by 209138 on Jul. 3, 1997. The sense and antisense nucleotide sequences determined by respectively, contain an open reading frame in the sense sequence (SEQ ID NO:28) encoding a polypeptide of 118 amino acid residues, including an initiation codon encoding an N-terminal methionine at nucleotide positions 59–61. Nucleic acid molecules of the invention include those encoding the complete amino acid sequence excepting the N-terminal methionine shown in SEQ ID NO:15, or the complete amino acid sequence excepting the N-terminal methionine encoded by the cDNA clone in ATCC Deposit Number 209138, which molecules also can encode additional amino acids fused to the N-terminus of the IL-20 amino acid sequence. Nucleic acid molecules of the invention further include those encoding any of the N-terminal and/or C-terminal IL-20 deletion mutations with termini of $n^3$ and/or $m^3$ as set forth below.

IL-20 has a predicted leader sequence of 20 amino acids underlined in FIG. 1; and the amino acid sequence of the predicted mature IL-20 protein is also shown in FIG. 1, as amino acid residues 21–180 and as residues 1–160 in SEQ ID NO:2. The encoded polypeptide also has a predicted leader sequence of 20 amino acids of the IL-20 polypeptide of the invention as shown as amino acid residues 1–20 in SEQ ID NO:15, and a predicted mature protein comprising amino acids residues 21–118 of the IL-20 polypeptide of the invention as shown in SEQ ID NO:15.

Thus, one aspect of the invention provides an isolated nucleic acid molecule comprising a polynucleotide having a nucleotide sequence selected from the group consisting of: (a) a nucleotide sequence encoding the IL-20 polypeptide having the complete amino acid sequence in SEQ ID NO:2 (i.e., positions −20 to 160 of SEQ ID NO:2); (b) a nucleotide sequence encoding the IL-20 polypeptide having the complete amino acid sequence in SEQ ID NO:15 (i.e., positions 1 to 118 of SEQ ID NO:2); (c) a nucleotide sequence encoding the IL-20 polypeptide having the complete amino acid sequence in SEQ ID NO:2 excepting the N-terminal methionine (i.e., positions −19 to 160 of SEQ ID NO:2); (d) a nucleotide sequence encoding the IL-20 polypeptide having the complete amino acid sequence in SEQ ID NO:15 excepting the N-terminal methionine (i.e., positions 2 to 118 of SEQ ID NO:15); (e) a nucleotide sequence encoding the predicted mature IL-20 polypeptide having the amino acid sequence at positions 1 to 160 in SEQ ID NO:2; (f) a nucleotide sequence encoding the predicted mature IL-20 polypeptide having the amino acid sequence at positions 21 to 118 in SEQ ID NO:15; (g) a nucleotide sequence encoding the IL-20 polypeptide having the complete amino acid sequence encoded by the cDNA clone contained in ATCC Deposit No. 209232; (h) a nucleotide sequence encoding the IL-20 polypeptide having the complete amino acid sequence encoded by the cDNA clone contained in ATCC Deposit No. 209138; (i) a nucleotide sequence encoding the IL-20 polypeptide having the complete amino acid sequence excepting the N-terminal methionine encoded by the cDNA clone contained in ATCC Deposit No. 209232; (j) a nucleotide sequence encoding the IL-20 polypeptide having the complete amino acid sequence excepting the N-terminal methionine encoded by the cDNA clone contained in ATCC Deposit No. 209138; (k) a nucleotide sequence encoding the mature IL-20 polypeptide having the amino acid sequence encoded by the cDNA clone contained in ATCC Deposit No. 209232; (l) a nucleotide sequence encoding the mature IL-20 polypeptide having the amino acid sequence encoded by the cDNA clone contained in ATCC Deposit No. 209138; and, (m) a nucleotide sequence complementary to any of the nucleotide sequences in (a), (b), (c), (d), (e), (f), (g), (h), (i), (j), (k) or (l), above.

Further embodiments of the invention include isolated nucleic acid molecules that comprise a polynucleotide having a nucleotide sequence at least 90% identical to (that is to say, at most 10% different from), and more preferably at least 95%, 96%, 97%, 98% or 99% identical to (that is to say, at most 5%, 4%, 3%, 2% or 1% different from), any of the nucleotide sequences in (a), (b), (c), (d), (e), (f), (g), (h), (i), (j), (k), (l) or (m), above, or a polynucleotide which hybridizes under stringent hybridization. conditions to a polynucleotide in (a), (b), (c), (d), (e), (f), (g), (h), (i), (j), (k), (l) or (m), above. This polynucleotide which hybridizes does not hybridize under stringent hybridization conditions to a polynucleotide having a nucleotide sequence consisting of only A residues or of only T residues. An additional nucleic acid embodiment of the invention relates to an isolatled nucleic acid molecule comprising a polynucleotide which encodes the amino acid sequence of an epitope-bearing portion of an IL-20 polypeptide having an amino acid sequence in (a), (b), (c), (d), (e), (f), (g), (h), (i), (j), (k) or (l), above. A further nucleic acid embodiment of the invention relates to an isolated nucleic acid molecule comprising a polynucleotide which encodes the amino acid sequence of an IL-20 polypeptide having an amino acid sequence which contains at least one conservative amino acid substitution, but not more than 50 conservative amino acid substitutions, even more preferably, not more than 40 conservative amino acid substitutions, still more preferably not more than 30 conservative amino acid substitutions, and still even more preferably not more than 20 conservative amino acid substitutions. Of course, in order of ever-increasing preference, it is highly preferable for a polynucleotide which encodes the amino acid sequence of an IL-20 polypeptide to have an amino acid sequence which contains not more than 10, 9, 8, 7, 6, 5, 4, 3, 2 or 1 conservative amino acid substitutions.

The present invention also relates to recombinant vectors, which include the isolated nucleic acid molecules of the present invention, and to host cells containing the recombinant vectors, as well as to methods of making such vectors and host cells and for using them for production of IL-20 polypeptides or peptides by recombinant techniques.

The invention further provides an isolated IL-20 polypeptide comprising an amino acid sequence selected from the group consisting of: (a) the amino acid sequence of the full-length IL-20 polypeptide having the complete amino acid sequence shown in SEQ ID NO:2 (i.e., positions −20 to 160 of SEQ ID NO:2); (b) the amino acid sequence of the full-length IL-20 polypeptide having the complete amino acid sequence shown in SEQ ID NO:15 (i.e., positions 1 to 118 of SEQ ID NO:2); (c) the amino acid sequence of the full-length IL-20 polypeptide having the complete amino acid sequence shown in SEQ ID NO:2 excepting the N-terminal methionine (i.e., positions −19 to 160 of SEQ ID NO:2); (d) the amino acid sequence of the full-length IL-20 polypeptide having the complete amino acid sequence shown in SEQ ID NO:15 excepting the N-terminal methionine (i.e., positions 2 to 118 of SEQ ID NO:15); (e) the amino acid sequence of the predicted mature IL-20 polypeptide having the amino acid sequence at positions 1 to 160 in SEQ ID NO:2; (f) the amino acid sequence of the predicted mature IL-20 polypeptide having the amino acid sequence at positions 21 to 118 in SEQ ID NO:15; (f) the complete amino acid sequence encoded by the cDNA clone contained in the ATCC Deposit No. 209232; (g) the complete amino acid sequence encoded by the cDNA clone contained in the ATCC Deposit No. 209138; (h) the complete amino acid sequence excepting the N-terminal methionine encoded by the cDNA clone contained in the ATCC Deposit No. 209232; (i) the complete amino acid sequence excepting the N-terminal methionine encoded by the cDNA clone contained in the ATCC Deposit No. 209138; (j) the complete amino acid sequence of the predicted mature IL-20 polypeptide encoded by the cDNA clone contained in the ATCC Deposit No. 209232; and, (k) the complete amino acid sequence of the predicted mature IL-20 polypeptide encoded by the cDNA clone contained in the ATCC Deposit No. 209138. The polypeptides of the present invention also include polypeptides having an amino acid sequence at least 80% identical to (that is to say, at most 20% different from), more preferably at least 90% identical to (that is to say, at most 10% different from), and still more preferably 95%, 96%, 97%, 98% or 99% identical to (that is to say, at most 5%, 4%, 3%, 2% or 1% different from) those described in (a), (b), (c), (d), (c), (f), (g), (h), (i), (j) or (k), above, as well as polypeptides having an amino acid sequence with at least 90% similarity, and more preferably at least 95% similarity, to those above.

An additional embodiment of this aspect of the invention relates to a peptide or polypeptide which comprises the amino acid sequence of an epitope-bearing portion of an IL-20 polypeptide having an amino acid sequence described in (a), (b), (c), (d), (e), (f), (g), (h), (i), (j) or (k), above. Peptides or polypeptides having the amino acid sequence of an epitope-bearing portion of an IL-20 polypeptide of the invention include portions of such polypeptides with at least six or seven, preferably at least nine, and more preferably at least about 30 amino acids to about 50 amino acids, although epitope-bearing polypeptides of any length up to and including the entire amino acid sequence of a polypeptide of the invention described above also are included in the invention.

A further embodiment of the invention relates to a peptide or polypeptide which comprises the amino acid sequence of an IL-20 polypeptide having an amino acid sequence which contains at least one conservative amino acid substitution, but not more than 50 conservative amino acid substitutions, even more preferably, not more than 40 conservative amino acid substitutions, still more preferably not more than 30 conservative amino acid substitutions, and still even more preferably not more than 20 conservative amino acid substitutions. Of course, in order of ever-increasing preference, it is highly preferable for a peptide or polypeptide to have an amino acid sequence which comprises the amino acid sequence of an IL-20 polypeptide, which contains at least one, but not more than 10, 9, 8, 7, 6, 5,14, 3, 2 or 1 conservative amino acid substitutions.

In another embodiment, the invention provides an isolated antibody that binds specifically to an IL-20 polypeptide having an amino acid sequence described in (a), (b), (c), (d), (e), (f), (g), (h), (i), (j) or (k), above. The invention further provides methods for isolating antibodies that bind specifically to an IL-20 polypeptide having an amino acid sequence as described herein. Such antibodies are useful diagnostically or therapeutically as described below.

The invention also provides for pharmaceutical compositions comprising IL-20 polypeptides, particularly human IL-20 polypeptides, which may be employed, for instance, to treat disorders relating to the proliferation or differentiation of T-cells, cellular activation, hemostasis, angiogenesis, tumor metastasis, cellular migration and ovulation, as well as neurogenesis. Methods of treating individuals in need of IL-20 polypeptides are also provided.

The invention further provides compositions comprising an IL-20 polynucleotide or an IL-20 polypeptide for administration to cells in vitro, to cells ex vivo and to cells in vivo, or to a multicellular organism. In certain particularly preferred embodiments of this aspect of the invention, the compositions comprise an IL-20 polynucleotide for expression of an IL-20 polypeptide in a host organism for treatment of disease. Particularly preferred in this regard is expression in a human patient for treatment of a dysfunction associated with aberrant endogenous activity of IL-20.

The present invention also provides a screening method for identifying compounds capable of enhancing or inhibiting a biological activity of the IL-20 polypeptide, which involves contacting a receptor which is enhanced by the IL-20 polypeptide with the candidate compound in the presence of an IL-20 polypeptide, assaying the IL-6 secretion or lymphocyte proliferation activity of the receptor in the presence of the candidate compound and of IL-20 polypeptide, and comparing the receptor activity to a standard level of activity, the standard being assayed when contact is made between the receptor and in the presence of the IL-20 polypeptide and the absence of the candidate compound In this assay, an increase in receptor activity over the standard indicates that the candidate compound is an agonist of IL-20 activity and a decrease in receptor activity compared to the standard indicates that the compound is an antagonist of IL-20 activity.

In another aspect, a screening assay for)agonists and antagonists is provided which involves determining the effect a candidate compound has on IL-20 binding to a receptor. In particular, the method involves contacting the receptor with an IL-20 polypeptide and a candidate compound and determining whether IL-20 polypeptide binding to the receptor is increased or decreased due to the presence of the candidate compound. In this assay, an increase in binding of IL-20 over the standard binding indicates that the candidate compound is an agonist of IL-20 binding activity and a decrease in IL-20 binding compared to the standard indicates that the compound is an antagonist of IL-20 binding activity.

In yet another aspect, the IL-20 polypeptide may bind to a cell surface protein which also function as a viral receptor or coreceptor. Thus, IL-20, or agonists or antagonists thereof, may be used to regulate viral infectivity at the level of viral binding or interaction with the IL-20 receptor or coreceptor or during the process of viral internalization or entry into the cell.

It has been discovered that IL-20 is expressed not only in thymus, but also in thymus tumor and 12 week old whole human embryo. Therefore, nucleic acids of the invention are useful as hybridization probes for differential identification of the tissue(s) or cell type(s) present in a biological sample. Similarly, polypeptides and antibodies directed to those polypeptides are useful to provide immunological probes for differential identification of the tissue(s) or cell type(s). In addition, for a number of disorders of the above tissues or cells, particularly of the immune, significantly higher or lower levels of IL-20 gene expression may be detected in certain tissues (e.g., cancerous and wounded tissues) or bodily fluids (e.g., serum, plasma, urine, synovial fluid or spinal fluid) taken from an individual having such a disorder, relative to a "standard" IL-20 gene expression level, i.e., the IL-20 expression level in healthy tissue from an individual not having the immune system disorder. Thus, the invention provides a diagnostic method useful during diagnosis of such a disorder, which involves: (a) assaying IL-20 gene expression level in cells or body fluid of an individual; (b) comparing the IL-20 gene expression level with a standard IL-20 gene expression level, whereby an increase or decrease in the assayed IL-20 gene expression level compared to the standard expression level is indicative of disorder in the immune system.

A further consequence of the observed thymus-restricted expression of endogenous IL-20 is that the IL-20 of the present invention may be useful in the regulation of the proliferation or differentiation of T-cells in general, for specific subsets of T-cells, for other immune cells in general, for other specific subsets of other immune cells, or any combination thereof. Thus, IL-20 of the present invention may be used therapeutically to treat disorders related to the immune system, including autoimmune and hematopoietic diseases or disorders, including AIDS, arthritis, or normal or abnormal cellular or systemic processes related to aging, and the like.

An additional aspect of the invention is related to a method for treating an individual in need of an increased level of IL-20 activity in the body comprising administering to such an individual a composition comprising a therapeutically effective amount of an isolated IL-20 polypeptide of the invention or an agonist thereof.

A still further aspect of the invention is related to a method for treating an individual in need of a decreased level of IL-20 activity in the body comprising, administering to such an individual a composition comprising a therapeutically effective amount of an IL-20 antagonist. Preferred antagonists for use in the present invention are IL-20-specific antibodies.

BRIEF DESCRIPTION OF THE FIGURES

FIG. 1 shows the nucleotide sequence (SEQ ID NO:1) and deduced amino acid sequence (SEQ ID NO:2) of IL-20. The predicted leader sequence of about 20 amino acids is underlined with a single underline. Note that the methionine residue at the beginning of the leader sequence in FIG. 1 is shown in position number (positive) 1, whereas the leader positions in the corresponding sequence of SEQ ID NO:2 are designated with negative position numbers. Thus, the leader sequence positions 1 to 20 in FIG. 1 correspond to positions −20 to −1 in SEQ ID NO:2. The leader sequence positions 1 to 20 in FIG. 1 also correspond to positions 1 to 20 in SEQ ID NO:15.

The amino acid sequence of positions 1–118 of the polypeptide shown in FIG. 1 (i.e., positions −20 to 98 of SEQ ID NO:2) corresponds exactly to the amino acid sequence of positions 1 to 118 of SEQ ID NO:15. The nucleotide sequence set forth in FIG. 1 (SEQ ID NO:1) corresponds to nucleotide positions 15–719 of the nucleotide sequence set forth as SEQ ID NO:28 with the exception of a single "G" nucleotide at position 399 of SEQ ID NO:1 which is absent from SEQ ID NO:28. The sequence set forth in FIG. 1 (SEQ ID NO:1) is the reverse complement of nucleotides 6–709 of SEQ ID NO:29 with with the exception of the complement of a single "G" nucleotide at position 399 of SEQ ID NO:1 which is absent from SEQ ID NO:29.

A single potential asparagine-linked glycosylation site is marked in the amino acid sequence of IL-20 in FIG. 1. The site is located from asparagine-75 through glutamic acid-78 in FIG. 1 (N-75, S-76, S-77, E-78) [this sequence corresponds exactly to asparagine-55 through glutamic acid-58 in SEQ ID NO:2 (N-55, S-56, S-57, E-58)], and is marked with a bolded pound symbol (#) above the nucleotide sequence coupled with a bolded one letter abbreviation for the asparagine (N) in the amino acid sequence in FIG. 1; i.e, the actual asparagine residue which is potentially glycosylated is bolded in FIG. 1.

Three potential Protein Kinase C (PKC) phosphorylation sites are also marked in FIG. 1 with a bolded serine symbol (S) in the IL-20 amino acid sequence and an asterisk (*) above the first nucleotide encoding that serine residue in the IL-20 nucleotide sequence. The potential PKC phosphorylation sequences are found at the following locations in the IL-20 amino acid sequence: S-24 through K-26 (S-24, P-25, K-26); S-27 through R-29 (S-27, K-28, R-29); and S-93 through K-95 (S-93, N-94, K-95). A potential Casein Kinase II (CK2) phosphorylation site is also marked in FIG. 1 with a bolded threonine symbol (T) in the IL-20 amino acid sequence and an asterisk (*) above the first nucleotide encoding the appropriate threonine residue in the IL-20 nucleotide sequence. The potential CK2 phosphorylation sequence is found at the following location in the IL-20 amino acid sequence: T-131 through E-134 (T-131, M-132, Q-133, E-134).

Regions of high identity between IL-20 and the closely related IL-21, IL-22, mouse IL-17, and viral IL-17 (an aligment of these sequences is presented in FIGS. 4A and 4B) are delineated in FIG. 1 with a double underline. These regions are not limiting and are labeled as Conserved Domain (CD)-I, CD-II, CD-III, and CD-IV in FIG. 1.

FIG. 2 shows the regions of identity between the amino acid sequences of the IL-20 protein and translation product of the human mRNA for IL-17 (SEQ ID NO:3), determined by the computer program Bestfit (Wisconsin Sequence Analysis Package, Version 8 for Unix, Genetics Computer Group, University Research Park, 575 Science Drive, Madison, Wis. 53711) using the default parameters.

Figure 3:
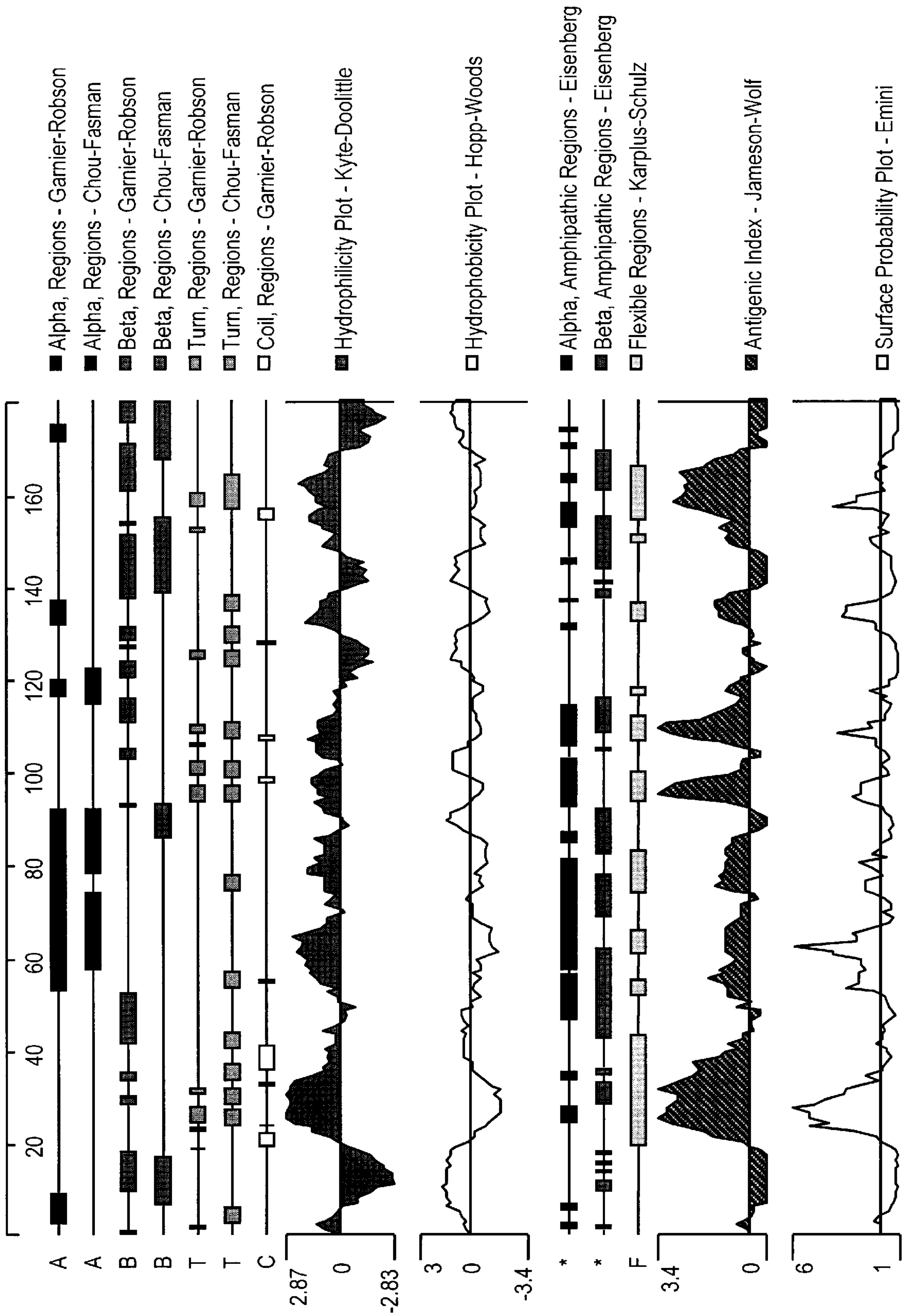

FIG. 3 shows an analysis of the IL-20 amino acid sequence. Alpha, beta, turn and coil regions; hydrophilicity and hydrophobicity; amphipathic regions; flexible regions; antigenic index and surface probability are shown. In the "Antigenic Index or Jameson-Wolf" graph, the positive peaks indicate locations of the highly antigenic regions of the IL-20 protein, i.e., regions from which epitope-bearing peptides of the invention can be obtained.

The data presented in FIG. 3 is also represented in tabular form in Table I. The columns in Table I are labeled with the headings "Res", "Position", and Roman Numerals I–XIV. The column headings refer to the following features of the amino acid sequence presented in FIG. 3 and Table I: "Res": amino acid residue of SEQ ID NO:2 and FIG. 1; "Position": position of the corresponding residue within SEQ ID NO:2 and FIG. 1; I: Alpha, Regions—Garnier-Robson; II: Alpha, Regions—Chou-Fasman; III: Beta, Regions—Garnier-Robson; IV: Beta, Regions—Chou-Fasman; V: Turn, Regions—Garnier-Robson; VI: Turn, Regions—Chou-Fasman; VII: Coil, Regions—Garnier-Robson; VIII: Hydrophilicity Plot—Kyte-Doolittle; LX: Hydrophobicity Plot—Hopp-Woods; X: Alpha, Amphipathic Regions—Eisenberg; XI: Beta, Amphipathic Regions—Eisenberg; XII: Flexible Regions—Karplus-Schulz; XIII: Antigenic Index—Jameson-Wolf; and XIV: Surface Probability Plot—Emini.

Figure 4A:
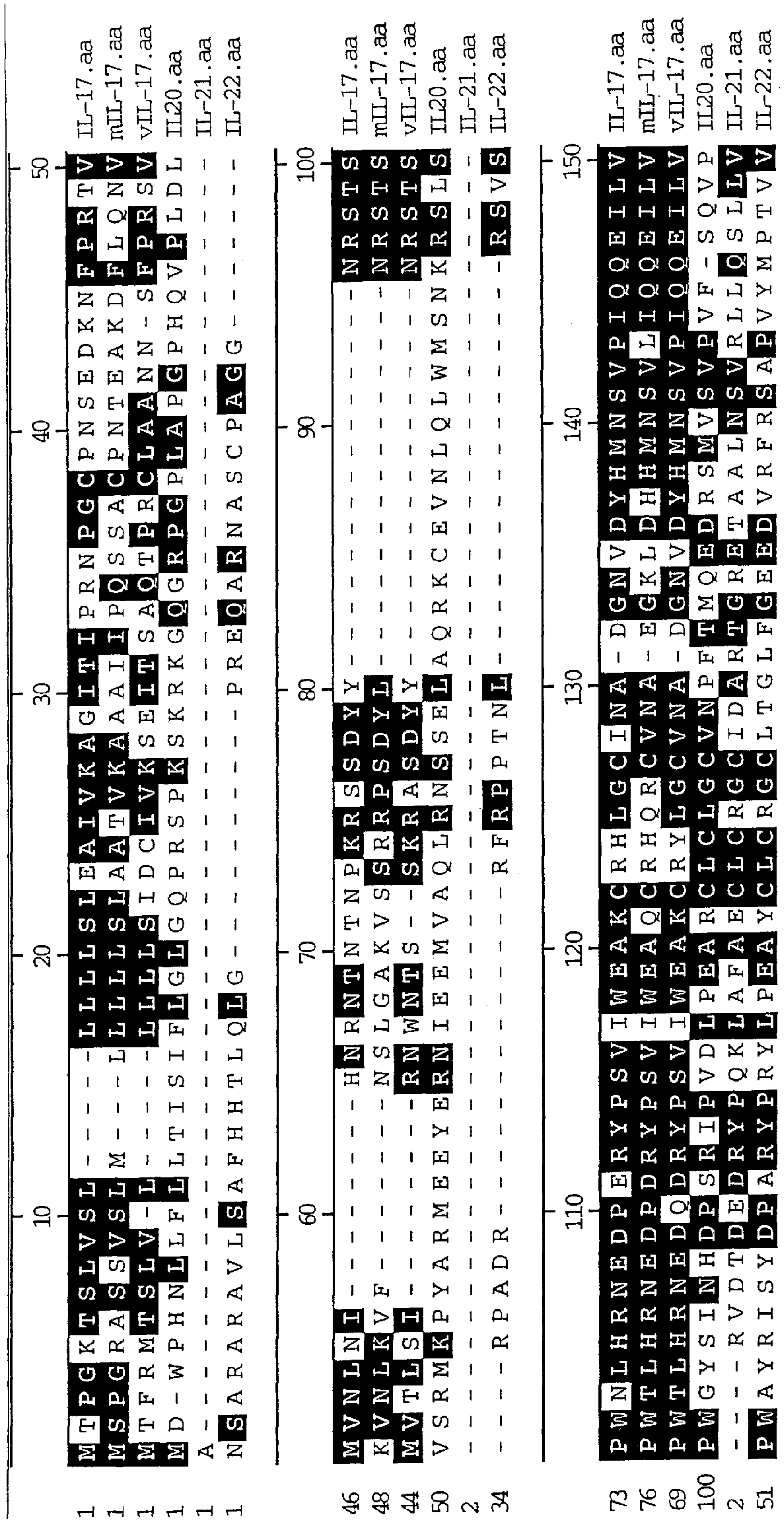
Figure 4B:
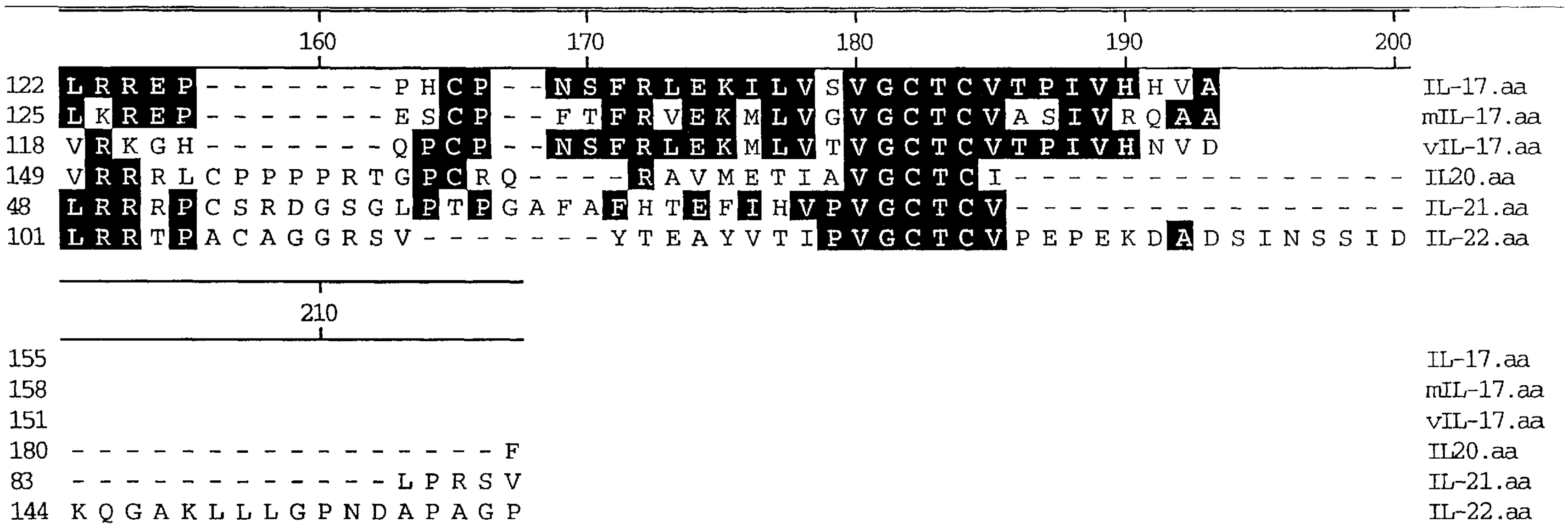

FIGS. 4A and 4B show the regions of identity between the amino acid sequence of IL-20, the amino acid sequence of the IL-21 and IL-22 proteins (disclosed in copending U.S. Provisional Application Serial No. 60/087,340; filed May 29, 1998; IL-21 and IL-22 are shown as SEQ ID NO:1 and SEQ ID NO:12, respectively), and the translation products of human Interleukin-17 (ATCC Accession No. U32659; SEQ ID NO:3), mouse Interleukin-17 (ATCC Accession No. U43088: SEQ ID NO:13), and viral Interleukin-17 (ATCC Accession No. X64346; SEQ ID NO:14), as determined by the MegAlign component of the computer program DNA*Star (DNASTAR, Inc.) using the default parameters.

DETAILED DESCRIPTION

The present invention provides isolated nucleic acid molecules comprising a polynucleotide encoding an IL-20 polypeptide having the amino acid sequence shown in positions 1–118 of SEQ ID NO:15, which was determined by sequencing a cloned cDNA. The nucleotide sequences shown in SEQ ID NO:28 and in SEQ ID NO:29 were obtained by sequencing the HTSGS30 clone, which was deposited as plasmid DNA in ATCC Deposit Number 209138 on Jul. 3, 1997 at the American Type Culture Collection, 10801 University Boulevard, Manassas, Va. 20110. The deposited clone is contained in the pBluescript SK(−) plasmid (Stratagene, La Jolla, Calif.).

The present invention provides isolated nucleic acid molecules comprising a polynucleotide encoding an IL-20 polypeptide having the amino acid sequence shown in SEQ ID NO:2, which was determined by sequencing a cloned cDNA. The nucleotide sequence shown in FIG. 1 (SEQ ID NO:1) was obtained by sequencing the HTSGS30 clone, which was deposited on Aug. 29, 1997 at the American Type Culture Collection, 10801 University Boulevard, Manassas, Va. 20110, and given accession number ATCC 209232. The deposited clone is contained in the pBluescript SK(−) plasmid (Stratagene, La Jolla, Calif.).

The IL-20 protein of the present invention shares sequence homology with the translation product of the human mRNA for IL-17 (FIG. 2; SEQ ID NO:3). Human IL-17 is thought to be an important immunoregulatory molecule. The IL-17/IL-17 receptor complex activates NF-κB activity. NF-κB is a transcription factor known to regulate a large number of gene products involved in growth control. NF-κB-induced gene products include molecules involved in immune, inflammatory, or actute phase responses, such as immunoglobulin light chain, major histocompatibility complex (MHC), IL-2R α chain, and cytokines such as IL-1β, IL-6, and TNFα. NF-κB directly stimulates the HIV enhancer in T-cells and can itself be activated by different viral proteins with oncogenic potential such as the hepatitis B virus HBX protein, EBV LMP1, and HTLV-1 Tax protein. The induction of NF-κB by Tax results in up-regulation of IL-2 and IL-2R and subsequently uncontrolled T-cell growth. IL-17 and HVS13, a gene product of HVS and a murine counterpart of IL-17, strongly induce IL-6 expression. IL-6 is a potent growth factor for myelomas, plasmacytomas, and hybridomas and is involved in the growth of Lennert's Lymphoma T-cells.

Nucleic Acid Molecules

Unless otherwise indicated, all nucleotide sequences determined by sequencing a DNA molecule herein were determined using an automated DNA sequencer (such as the Model 373 from Applied Biosystems, Inc., Foster City, Calif.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

By "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymridine deoxyribonucleotide (T) in the specified deoxyribonucleotide sequence is replaced by the ribonucleotide uridine (U).

Using the information provided herein, such as the nucleotide sequence in FIG. 1 (SEQ ID NO:1), a nucleic acid molecule of the present invention encoding an IL-20 polypeptide may be obtained using standard cloning and screening procedures, such as those for cloning cDNAs using mRNA as starting material. Illustrative of the invention, the nucleic acid molecule described in FIG. 1 (SEQ ID NO:1) and in SEQ ID NO:28 and SEQ ID NO:29 was discovered in a cDNA library derived from thymus. Additional clones of the same gene were also identified in thymus tumor and 12 week old whole human embryo cDNA libraries.

The determined nucleotide sequence of the IL-20 cDNA of FIG. 1 (SEQ ID NO:1) contains an open reading frame encoding a protein of 180 amino acid residues, with an initiation codon at nucleotide positions 45–47 of the nucleotide sequence in FIG. 1 (SEQ ID NO:1), and a deduced molecular weight of about 20.4 kDa. The determined nucleotide sequence of the IL-20 cDNA of SEQ ID NO:15 comprises an open reading frame encoding a protein of 118 amino acid residues, with an initiation codon at nucleotide positions 59–61 of the nucleotide sequence in SEQ ID NO:15. The amino acid sequence of the IL-20 protein shown in SEQ ID NO:2 is about 34.0 % identical to human mRNA for IL-17 (FIG. 2; Yao, Z., et al., *J. Immunol.* 155:5483–5486 (1995); GenBank Accession No. U32659).

Leader and Mature Sequences

The amino acid sequence of the complete IL-20 protein includes a leader sequence and a mature protein, as shown in SEQ ID NO:2. More in particular, the present invention provides nucleic acid molecules encoding a mature form of the IL-20 protein. Thus, according to the signal hypothesis, once export of the growing protein chain across the rough endoplasmic reticulum has been initiated, proteins secreted by mammalian cells have a signal or secretory leader sequence which is cleaved from the complete polypeptide to produce a secreted "mature" form of the protein. Most mammalian cells and even insect cells cleave secreted proteins with the same specificity. However, in some cases, cleavage of a secreted protein is not entirely uniform, which results in two or more mature species of the protein. Further, it has long been known that the cleavage specificity of a secreted protein is ultimately determined by the primary structure of the complete protein, that is, it is inherent in the amino acid sequence of the polypeptide. Therefore, the present invention provides a nucleotide sequence encoding the mature IL-20 polypeptide having the amino acid sequence encoded by the cDNA clone contained in ATCC Deposit No. 209232. By the "mature IL-20 polypeptide having the amino acid sequence encoded by the cDNA clone in ATCC Deposit No. 209232" is meant the mature form(s) of the IL-20 protein produced by expression in a mammalian cell (e.g., COS cells, as described below) of the complete open reading frame encoded by the human DNA sequence of the deposited clone. The present invention also provides a nucleotide sequence encoding the mature IL-20 polypeptide having the amino acid sequence encoded by the cDNA clone contained in ATCC Deposit No. 209138. By the "mature IL-20 polypeptide having the amino acid sequence encoded by the cDNA clone in ATCC Deposit No. 209138" is meant the mature form(s) of the IL-20 protein produced by expression in a mammalian cell (e.g., COS cells, as described below) of the complete open reading frame encoded by the human DNA sequence of the deposited clone.

In addition, methods for predicting whether a protein has a secretory leader as well as the cleavage point for that leader sequence are available. For instance, the method of McGeoch (*Virus Res.* 3:271–286 (1985)) uses the information from a short N-terminal charged region and a subsequent uncharged region of the complete (uncleaved) protein. The method of von Heinje (*Nucleic Acids Res.* 14:4683–4690 (1986)) uses the information from the residues surrounding the cleavage site, typically residues −13 to +2 where +1 indicates the amino terminus of the mature protein. The accuracy of predicting the cleavage points of known mammalian secretory proteins for each of these methods is in the range of 75–80% (von Heinje, supra). However, the two methods do not always produce the same predicted cleavage point(s) for a given protein.

In the present case, the deduced amino acid sequence of the complete IL-20 polypeptide was analyzed by a computer program "PSORT", available from Dr. Kenta Nakai of the Institute for Chemical Research, Kyoto University (Nakai, K. and Kanehisa, M. *Genomics* 14:897–911 (1992)), which is an expert system for predicting the cellular location of a protein based on the amino acid sequence. As part of this computational prediction of localization, the methods of McGeoch and von Heinje are incorporated. Thus, the computation analysis above predicted a single cleavage site within the complete amino acid sequence shown in SEQ ID NO:2 and in SEQ ID NO:15.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

In specific embodiments, the polynucleotides of this invention are less than 300 kb, 200 kb, 100 kb, 50 kb, 15 kb, 10 kb or 7.5 kb in length. In a further embodiment, polynucleotides of the invention comprise at least 15 contiguous nucleotides of IL-20 coding sequence, but do not comprise all or a portion of any IL-20 intron. In another embodiment, the nucleic acid comprising IL-20 coding sequence does not contain coding sequences of a genomic flanking gene (i.e. 5' or 3' to the IL-20 coding sequence in the genome).

By "isolated" nucleic acid molecule(s) is intended a nucleic acid molecule, DNA or RNA, which has been removed from its native environment For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) with an initiation codon at positions 45–47 of the nucleotide sequence shown in FIG. 1 (SEQ ID NO:1). Isolated nucleic acid molecules of the present invention also include DNA molecules comprising an open reading frame (ORF) with an initiation codon at positions 59–61 of the nucleotide sequence shown in SEQ ID NO:28.

Also included are DNA molecules comprising the coding sequence for the predicted mature IL-20 protein shown at positions 1–160 of SEQ ID NO:2. In addition, DNA molecules comprising the coding sequence for the predicted mature IL-20 protein shown at positions 21–118 of SEQ ID NO:15 are also included in the present invention.

In addition, isolated nucleic acid molecules of the invention include DNA molecules which comprise a sequence substantially different from those described above but which, due to the degeneracy of the genetic code; still encode the IL-20 protein. Of course, the genetic code and species-specific codon preferences are well known in the art. Thus, it would be routine for one skilled in the art to generate the degenerate variants described above, for instance, to optimize codon expression for a particular host (e.g., change codons in the human mRNA to those preferred by a bacterial host such as *E. coli*).

In another aspect, the invention provides isolated nucleic acid molecules encoding the IL-20 polypeptide having an amino acid sequence encoded by the cDNA clone contained in the plasmid deposited as ATCC Deposit No. 209232 on Aug. 29, 1997. Preferably, this nucleic acid molecule will encode the mature polypeptide encoded by the above-described deposited cDNA clone.

In another aspect, the invention provides isolated nucleic acid molecules encoding the IL-20 polypeptide having an amino acid sequence encoded by the cDNA clone contained in the plasmid deposited as ATCC Deposit No. 209138 on Jul. 3, 1997. Preferably, this nucleic acid plasmid deposited as ATCC Deposit No. 209138 on Jul. 3, 1997. Preferably, this nucleic acid clone.

The invention further provides an isolated nucleic acid molecule having the nucleotide sequence shown in FIG. 1 (SEQ ID NO:1) or the nucleotide sequence of the IL-20 cDNA contained in the above-described deposited clone (ATCC Deposit No. 209232), or a nucleic acid molecule having a sequence complementary to one of the above sequences. The invention also provides an isolated nucleic acid molecule having the nucleotide sequence shown in SEQ ID NO:28 or the nucleotide sequence of the IL-20 cDNA contained in the above-described deposited clone (ATCC Deposit No. 209138), or a nucleic acid molecule having a sequence complementary to one of the above sequences. Such isolated molecules, particularly DNA molecules, are useful as probes for gene mapping, by in situ hybridization with chromosomes, and for detecting expression of the IL-20 gene in human tissue, for instance, by Northern blot analysis.

The present invention is further directed to nucleic acid molecules encoding portions of the nucleotide sequences described herein as well as to fragments of the isolated nucleic acid molecules described herein. In particular, the invention provides a polynucleotide having a nucleotide sequence representing the portion of SEQ ID NO:I which consists of positions 1–687 of SEQ ID NO:1. Also in particular, the invention provides a polynucleotide having a nucleotide sequence representing the portion of SEQ ID NO:28 which consists of positions 1–700 of SEQ ID NO:28.

In addition, the invention provides nucleic acid molecules having nucleotide sequences related to extensive portions of SEQ ID NO:1: HTYSK30Rb (SEQ ID NO:4). Preferably, this related polynucleotide is specifically excluded from the scope of the present invention. However, many polynucleotide sequences, such as EST sequences, are publicly available and accessible through sequence databases. Some of these sequences are related to SEQ ID NO:1 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 690 of SEQ ID NO:1, b is an integer of 15 to 705, where both a and b correspond to the positions of nucleotide residues shown in SEQ ID NO:1, and where the b is greater than or equal to a+14.

Further, the invention includes a polynucleotide comprising any portion of at least about 30 nucleotides, preferably at least about 50 nucleotides, of SEQ ID NO:1 from residue 60 to 599. Preferably, the invention includes a polynucleotide comprising any portion of at least about 30 nucleotides, preferably at least about 50 nucleotides, of SEQ ID NO:1 from residue 103 to 584. More preferably, the invention includes a polynucleotide comprising nucleotide residues 1–500, 25–525, 50–550, 75–575, 100–600, 125–625, 150–650, 175–675, 200–700, 103–595, 103–545 103–585, 103–580, 103–575, 103–570, 103–565, 103–560, 103–555, 103–550, 103–545, 103–540, 103–535, 103–530, 103–525, 103–520, 103–515, and 103–510.

Moreover, the invention includes a polynucleotide comprising any portion of at least about 30 nucleotides, preferably at least about 50 nucleotides, of SEQ ID NO:28 from residue 75 to 614. Preferably, the invention includes a polynucleotide comprising any portion of at least about 30 nucleotides, preferably at least about 50 nucleotides, of SEQ ID NO:28 from residue 118 to 599. More preferably, the invention includes a polynucleotide comprising nucleotide residues 15–515, 40–540, 65–565, 90–590, 115–615, 140–640, 165–665, 190–690, 215–715, 118–610, 118–605, 118–600, 118–595, 118–590, 118–585, 118–580, 118–575, 118–570, 118–565, 118–560, 118–555, 118–550, 118–545, 118–540, 118–535, 118–530, and 118–525.

More generally, by a fragment of an isolated nucleic acid molecule having the nucleotide sequence of the deposited cDNA or the nucleotide sequence shown in FIG. 1 (SEQ ID NO:1) is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50–300 nt in length are also useful according to the present invention as are fragments corresponding to most, if not all, of the nucleotide sequence of the deposited cDNA or as shown in FIG. 1 (SEQ ID NO:1). By a fragment at least 20 nt in length, for example, is intended fragments which include 20 or more contiguous bases from the nucleotide sequence of the deposited cDNA or the nucleotide sequence as shown in FIG. 1 (SEQ ID NO:1). Preferred nucleic acid fragments of the present invention include nucleic acid molecules encoding epitope-bearing portions of the IL-20 polypeptide as identified in FIG. 3 and described in more detail below.

Further, by a fragment of an isolated nucleic acid molecule having the nucleotide sequence of the deposited cDNA or the nucleotide sequence shown in SEQ ID NO:28 is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50–300 nt in length are also useful according to the present invention as are fragments corresponding to most, if not all, of the nucleotide sequence of the deposited cDNA or as shown in SEQ ID NO:28. By a fragment at least 20 nt in length, for example, is intended fragments which include 20 or more contiguous bases from the nucleotide sequence of the deposited cDNA or the nucleotide sequence as shown in SEQ ID NO:28. Preferred nucleic acid fragments of the present invention include nucleic acid molecules encoding epitope-bearing portions of the IL-20 polypeptide as identified in FIG. 3 and described in more detail below.

Also preferred in this aspect of the invention are fragments characterized by structural or functional attributes of IL-20. Preferred embodiments of the invention in this regard include fragments that comprise alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of IL-20.

Certain preferred regions in these regards are set out in FIG. 3, but may also be represented or identified by using a tabular representation of the data presented in FIG. 3. The DNA*STAR computer algorithm used to generate FIG. 3 (set on the original default parameters) will easily present the data in FIG. 3 in such a tabular format. A tabular format of the data in FIG. 3 may be used to easily determine specific boundaries of a preferred region.

The above-mentioned preferred regions set out in FIG. 3 include, but are not limited to, regions of the aforementioned types identified by analysis of the amino acid sequence set out in FIG. 1. As set out in FIG. 3, such preferred regions include Garnier-Robson alpha-regions, beta-regions, turn-regions, and coil-regions, Chou-Fasman alpha-regions, beta-regions, and coil-regions, Kyte-Doolittle hydrophilic regions and hydrophobic regions, Eisenberg alpha- and beta-amphipathic regions, Karplus-Schulz flexible regions, Emini surface-forming regions and Jameson-Wolf regions of high antigenic index.

TABLE I

| Res | Position | I | II | III | IV | V | VI | VII | VIII | IX | X | XI | XII | XIII | XIV |
|---|---|---|---|---|---|---|---|---|---|---|---|---|---|---|---|
| Met | 1 | . | . | B | . | . | . | . | 0.81 | 0.24 | . | . | . | 0.05 | 1.01 |
| Asp | 2 | . | . | . | . | T | . | . | 1.20 | 0.31 | * | * | . | 0.45 | 1.07 |
| Trp | 3 | A | . | . | . | . | T | . | 0.78 | 0.29 | * | . | . | 0.25 | 1.35 |
| Pro | 4 | A | . | . | . | . | T | . | 0.36 | 0.54 | . | . | . | −0.05 | 1.12 |
| His | 5 | A | . | . | . | . | T | . | 0.04 | 0.61 | . | . | . | −0.20 | 0.55 |
| Asn | 6 | A | . | . | . | . | T | . | −0.17 | 1.40 | * | . | . | −0.20 | 0.46 |
| Leu | 7 | A | . | . | B | . | . | . | −0.98 | 1.17 | * | . | . | −0.60 | 0.24 |
| Leu | 8 | A | . | . | B | . | . | . | −1.00 | 1.43 | . | . | . | −0.60 | 0.15 |
| Phe | 9 | A | . | . | B | . | . | . | −1.68 | 1.41 | . | . | . | −0.60 | 0.13 |
| Leu | 10 | . | . | B | B | . | . | . | −1.94 | 1.70 | . | * | . | −0.60 | 0.11 |
| Leu | 11 | . | . | B | B | . | . | . | −2.83 | 1.40 | . | * | . | −0.60 | 0.18 |
| Thr | 12 | . | . | B | B | . | . | . | −2.72 | 1.40 | . | * | . | −0.60 | 0.15 |
| Ile | 13 | . | . | B | B | . | . | . | −2.72 | 1.40 | . | . | . | −0.60 | 0.16 |
| Ser | 14 | . | . | B | B | . | . | . | −2.37 | 1.40 | . | * | . | −0.60 | 0.16 |
| Ile | 15 | . | . | B | B | . | . | . | −2.37 | 1.14 | . | . | . | −0.60 | 0.11 |
| Phe | 16 | . | . | B | B | . | . | . | −1.90 | 1.34 | . | * | . | −0.60 | 0.13 |
| Leu | 17 | . | . | B | B | . | . | . | −1.59 | 1.09 | . | . | . | −0.60 | 0.09 |
| Gly | 18 | . | . | B | . | . | . | . | −0.91 | 1.10 | . | * | . | −0.40 | 0.23 |
| Leu | 19 | . | . | . | . | T | . | . | −0.50 | 0.84 | . | . | . | 0.00 | 0.41 |
| Gly | 20 | . | . | . | . | . | . | C | 0.09 | 0.06 | . | . | F | 0.25 | 0.97 |
| Gln | 21 | . | . | . | . | . | . | C | 0.58 | −0.24 | . | . | F | 1.34 | 1.32 |
| Pro | 22 | . | . | . | . | . | . | C | 1.43 | −0.24 | . | . | F | 1.68 | 2.47 |
| Arg | 23 | . | . | . | . | T | . | . | 1.48 | −0.93 | . | . | F | 2.52 | 4.98 |
| Ser | 24 | . | . | . | . | . | T | C | 2.33 | −0.97 | . | . | F | 2.86 | 3.86 |
| Pro | 25 | . | . | . | . | T | T | . | 2.79 | −1.37 | * | . | F | 3.40 | 4.99 |
| Lys | 26 | . | . | . | . | T | T | . | 2.83 | −1.80 | * | . | F | 3.06 | 4.99 |
| Ser | 27 | . | . | . | . | T | T | . | 2.70 | −1.80 | * | . | F | 3.06 | 7.44 |
| Lys | 28 | . | . | . | . | T | . | . | 2.59 | −1.76 | * | . | F | 2.86 | 4.76 |
| Arg | 29 | . | . | B | . | . | T | . | 2.54 | −1.79 | . | * | F | 2.66 | 4.12 |
| Lys | 30 | . | . | B | . | . | T | . | 2.87 | −1.36 | . | * | F | 2.66 | 3.05 |
| Gly | 31 | . | . | . | . | T | T | . | 2.61 | −1.74 | . | * | F | 3.40 | 2.98 |
| Gln | 32 | . | . | . | . | T | T | . | 2.57 | −1.31 | . | * | F | 3.06 | 2.35 |
| Gly | 33 | . | . | . | . | . | . | C | 2.31 | −0.89 | . | * | F | 2.53 | 1.17 |
| Arg | 34 | . | . | B | . | . | T | . | 1.39 | −0.46 | * | . | F | 2.10 | 1.82 |
| Pro | 35 | . | . | B | . | . | T | . | 0.76 | −0.20 | * | * | F | 1.82 | 0.87 |
| Gly | 36 | . | . | . | . | . | T | C | 0.89 | −0.10 | . | * | F | 1.89 | 0.89 |
| Pro | 37 | . | . | . | . | . | T | C | 0.54 | −0.10 | . | . | F | 2.10 | 0.70 |
| Leu | 38 | . | . | . | . | . | . | C | 0.68 | 0.33 | . | . | F | 1.09 | 0.45 |
| Ala | 39 | . | . | . | . | . | . | C | 0.53 | 0.33 | . | . | F | 0.88 | 0.70 |
| Pro | 40 | . | . | . | . | . | . | C | 0.74 | 0.40 | . | . | F | 0.37 | 0.61 |
| Gly | 41 | . | . | . | . | . | T | C | 0.23 | 0.37 | . | . | F | 0.81 | 1.29 |
| Pro | 42 | . | . | B | . | . | T | . | 0.23 | 0.33 | . | . | F | 0.25 | 0.95 |
| His | 43 | . | . | B | . | . | T | . | 0.23 | 0.26 | . | * | F | 0.25 | 0.95 |
| Gln | 44 | . | . | B | . | . | T | . | 0.82 | 0.51 | . | * | . | −0.20 | 0.79 |
| Val | 45 | . | . | B | . | . | . | . | 0.22 | 0.09 | . | * | . | −0.10 | 0.85 |
| Pro | 46 | . | . | B | . | . | . | . | −0.29 | 0.34 | . | * | . | −0.10 | 0.52 |
| Leu | 47 | . | . | B | . | . | . | . | −0.38 | 0.49 | * | * | . | −0.40 | 0.22 |
| Asp | 48 | . | . | B | . | . | . | . | −0.23 | 0.47 | * | * | . | −0.40 | 0.40 |
| Leu | 49 | . | . | B | . | . | . | . | −0.83 | −0.17 | * | * | . | 0.50 | 0.51 |
| Val | 50 | . | . | B | . | . | . | . | 0.07 | 0.01 | * | * | . | −0.10 | 0.61 |
| Ser | 51 | . | . | B | . | . | . | . | 0.07 | −0.67 | * | * | . | 0.80 | 0.73 |
| Arg | 52 | . | . | B | . | . | . | . | 0.63 | −0.24 | * | * | F | 0.80 | 1.37 |
| Met | 53 | A | . | . | . | . | . | . | 0.04 | −0.17 | * | * | F | 0.80 | 2.89 |
| Lys | 54 | A | . | . | . | . | T | . | 0.97 | −0.31 | * | * | F | 1.00 | 2.17 |
| Pro | 55 | A | . | . | . | . | T | C | 1.22 | −0.70 | * | * | F | 1.50 | 2.17 |
| Tyr | 56 | A | . | . | . | . | T | . | 1.52 | −0.09 | * | * | . | 0.85 | 2.17 |
| Ala | 57 | A | . | . | . | . | T | . | 1.41 | −0.70 | . | * | . | 1.15 | 1.88 |
| Arg | 58 | A | A | . | . | . | . | . | 1.77 | −0.70 | * | * | . | 0.75 | 2.11 |
| Met | 59 | A | A | . | . | . | . | . | 1.72 | −0.37 | * | * | . | 0.45 | 2.11 |
| Glu | 60 | A | A | . | . | . | . | . | 2.04 | −1.13 | * | * | . | 0.75 | 3.62 |
| Glu | 61 | A | A | . | . | . | . | . | 2.29 | −1.63 | * | * | F | 0.90 | 3.62 |
| Tyr | 62 | A | A | . | . | . | . | . | 1.99 | −1.23 | * | * | F | 0.90 | 5.88 |
| Glu | 63 | A | A | . | . | . | . | . | 1.88 | −1.16 | * | . | F | 0.90 | 2.38 |
| Arg | 64 | A | A | . | . | . | . | . | 2.48 | −1.16 | * | . | F | 0.90 | 2.38 |
| Asn | 65 | A | A | . | . | . | . | . | 1.88 | −1.16 | * | . | F | 0.90 | 2.63 |
| Ile | 66 | A | A | . | . | . | . | . | 1.02 | −1.30 | * | . | F | 0.90 | 1.50 |
| Glu | 67 | A | A | . | . | . | . | . | 0.68 | −0.66 | * | . | . | 0.60 | 0.57 |
| Glu | 68 | A | A | . | . | . | . | . | 0.68 | −0.16 | * | . | . | 0.30 | 0.36 |
| Met | 69 | A | A | . | . | . | . | . | −0.24 | −0.16 | * | * | . | 0.30 | 0.88 |
| Val | 70 | A | A | . | . | . | . | . | −0.13 | −0.16 | * | * | . | 0.30 | 0.42 |
| Ala | 71 | A | A | . | . | . | . | . | 0.76 | −0.16 | * | * | . | 0.30 | 0.48 |
| Gln | 72 | A | A | . | . | . | . | . | 0.46 | 0.24 | * | * | . | −0.30 | 0.77 |
| Leu | 73 | A | A | . | . | . | . | . | 0.16 | 0.01 | * | * | . | −0.15 | 1.40 |
| Arg | 74 | A | A | . | . | . | . | . | 0.76 | −0.24 | * | * | F | 0.60 | 1.85 |
| Asn | 75 | A | . | . | . | . | T | . | 0.80 | −0.74 | * | * | F | 1.30 | 1.85 |
| Ser | 76 | A | . | . | . | . | T | . | 0.80 | −0.46 | * | * | F | 1.00 | 1.85 |
| Ser | 77 | A | . | . | . | . | T | . | 0.80 | −0.64 | * | * | F | 1.15 | 0.96 |

TABLE I-continued

| Res | Position | I | II | III | IV | V | VI | VII | VIII | IX | X | XI | XII | XIII | XIV |
|---|---|---|---|---|---|---|---|---|---|---|---|---|---|---|---|
| Glu | 78 | A | . | . | . | . | T | . | 1.72 | −0.24 | * | * | F | 1.00 | 1.03 |
| Leu | 79 | A | A | . | . | . | . | . | 1.66 | −0.64 | * | . | F | 0.90 | 1.50 |
| Ala | 80 | A | A | . | . | . | . | . | 0.99 | −1.03 | * | . | F | 0.90 | 2.24 |
| Gln | 81 | A | A | . | . | . | . | . | 1.29 | −0.84 | * | . | F | 0.75 | 0.69 |
| Arg | 82 | A | A | . | . | . | . | . | 0.73 | −0.84 | . | . | F | 0.90 | 1.46 |
| Lys | 83 | A | A | . | . | . | . | . | 0.73 | −0.89 | . | * | F | 0.90 | 1.07 |
| Cys | 84 | A | A | . | . | . | . | . | 0.73 | −0.99 | . | * | . | 0.60 | 0.99 |
| Glu | 85 | A | A | . | . | . | . | . | 1.32 | −0.70 | * | * | . | 0.60 | 0.42 |
| Val | 86 | A | A | . | B | . | . | . | 0.51 | −0.30 | * | * | . | 0.30 | 0.36 |
| Asn | 87 | A | A | . | B | . | . | . | 0.11 | 0.39 | * | * | . | −0.30 | 0.56 |
| Leu | 88 | A | A | . | B | . | . | . | −0.53 | 0.73 | . | * | . | −0.60 | 0.34 |
| Gln | 89 | A | A | . | B | . | . | . | −0.17 | 1.34 | . | * | . | −0.60 | 0.45 |
| Leu | 90 | A | A | . | B | . | . | . | −0.17 | 1.09 | . | * | . | −0.60 | 0.38 |
| Trp | 91 | A | A | . | B | . | . | . | 0.73 | 1.09 | . | * | . | −0.26 | 0.73 |
| Met | 92 | A | A | . | B | . | . | . | 0.84 | 0.40 | . | * | . | 0.08 | 0.85 |
| Ser | 93 | . | . | B | B | . | . | . | 1.36 | 0.00 | * | . | . | 0.87 | 2.01 |
| Asn | 94 | . | . | . | . | T | T | . | 0.54 | −0.30 | * | . | F | 2.76 | 2.57 |
| Lys | 95 | . | . | . | . | T | T | . | 1.06 | −0.53 | * | . | F | 3.40 | 2.14 |
| Arg | 96 | . | . | . | . | T | T | . | 1.13 | −0.76 | * | . | F | 3.06 | 2.14 |
| Ser | 97 | . | . | . | . | T | T | . | 1.44 | −0.71 | * | . | F | 2.72 | 2.06 |
| Leu | 98 | . | . | . | . | . | . | C | 1.40 | −0.20 | * | . | F | 1.68 | 1.08 |
| Ser | 99 | . | . | . | . | . | T | C | 1.16 | 0.23 | * | . | F | 0.79 | 0.55 |
| Pro | 100 | . | . | . | . | T | T | . | 0.81 | 0.99 | * | . | F | 0.35 | 0.64 |
| Trp | 101 | . | . | . | . | T | T | . | −0.19 | 0.99 | * | . | . | 0.35 | 1.04 |
| Gly | 102 | . | . | . | . | T | T | . | 0.11 | 0.99 | * | . | . | 0.20 | 0.54 |
| Tyr | 103 | . | . | B | . | . | . | . | 0.89 | 1.00 | * | . | . | −0.40 | 0.56 |
| Ser | 104 | . | . | B | . | . | . | . | 1.19 | 1.07 | . | . | . | −0.40 | 0.73 |
| Ile | 105 | . | . | B | . | . | . | . | 1.19 | 0.16 | . | * | . | 0.39 | 1.23 |
| Asn | 106 | . | . | . | . | T | . | . | 1.18 | 0.16 | * | . | . | 1.13 | 1.22 |
| His | 107 | . | . | . | . | . | . | C | 1.63 | −0.21 | * | . | F | 2.02 | 1.22 |
| Asp | 108 | . | . | . | . | . | T | C | 0.99 | −0.60 | * | . | F | 2.86 | 3.40 |
| Pro | 109 | . | . | . | . | T | T | . | 1.08 | −0.60 | * | * | F | 3.40 | 1.48 |
| Ser | 110 | . | . | . | . | T | T | . | 1.11 | −0.57 | * | * | F | 3.06 | 1.68 |
| Arg | 111 | . | . | B | . | . | T | . | 1.11 | −0.43 | * | * | F | 1.87 | 0.75 |
| Ile | 112 | . | . | B | . | . | . | . | 0.33 | −0.43 | * | * | F | 1.33 | 0.81 |
| Pro | 113 | . | . | B | . | . | . | . | 0.12 | −0.17 | * | * | . | 0.84 | 0.50 |
| Val | 114 | . | . | B | . | . | . | . | 0.33 | −0.13 | * | * | . | 0.50 | 0.39 |
| Asp | 115 | . | A | B | . | . | . | . | 0.04 | −0.13 | . | * | . | 0.30 | 0.97 |
| Leu | 116 | . | A | B | . | . | . | . | 0.04 | −0.31 | . | * | . | 0.30 | 0.63 |
| Pro | 117 | A | A | . | . | . | . | . | 0.27 | −0.74 | . | . | F | 0.90 | 1.67 |
| Glu | 118 | A | A | . | . | . | . | . | −0.33 | −0.81 | . | . | F | 0.75 | 0.54 |
| Ala | 119 | A | A | . | . | . | . | . | −0.14 | −0.13 | . | . | . | 0.30 | 0.54 |
| Arg | 120 | A | A | . | . | . | . | . | −0.96 | −0.24 | . | . | . | 0.30 | 0.19 |
| Gys | 121 | . | A | B | . | . | . | . | −0.49 | 0.01 | . | . | . | −0.30 | 0.09 |
| Leu | 122 | . | A | B | . | . | . | . | −0.94 | 0.44 | . | . | . | −0.60 | 0.09 |
| Cys | 123 | . | . | B | . | . | T | . | −1.80 | 0.51 | . | . | . | −0.20 | 0.02 |
| Leu | 124 | . | . | B | . | . | T | . | −1.21 | 1.16 | . | . | . | −0.20 | 0.03 |
| Gly | 125 | . | . | . | . | T | T | . | −1.53 | 0.99 | . | . | . | 0.20 | 0.06 |
| Gys | 126 | . | . | . | . | T | T | . | −1.57 | 0.73 | . | . | . | 0.20 | 0.19 |
| Val | 127 | . | . | B | . | . | . | . | −1.07 | 0.94 | . | . | . | −0.40 | 0.19 |
| Asn | 128 | . | . | . | . | . | T | C | −1.00 | 0.74 | . | . | . | 0.00 | 0.28 |
| Pro | 129 | . | . | B | . | . | T | . | −0.19 | 0.93 | . | . | . | −0.20 | 0.52 |
| Phe | 130 | . | . | B | . | . | T | . | 0.16 | 0.76 | . | . | . | −0.05 | 1.22 |
| Thr | 131 | . | . | B | . | . | T | . | 0.82 | 0.11 | * | . | . | 0.25 | 1.31 |
| Met | 132 | A | . | . | . | . | . | . | 1.79 | −0.29 | * | . | . | 0.65 | 1.42 |
| Gln | 133 | A | . | . | . | . | . | . | 1.49 | −0.71 | . | . | F | 1.10 | 3.21 |
| Glu | 134 | A | . | . | . | . | . | . | 1.10 | −1.11 | . | . | F | 1.10 | 2.98 |
| Asp | 135 | A | . | . | . | . | T | . | 0.94 | −0.99 | . | . | F | 1.30 | 2.98 |
| Arg | 136 | A | . | . | . | . | T | . | 0.96 | −0.96 | . | . | F | 1.30 | 1.28 |
| Ser | 137 | A | . | . | . | . | T | . | 0.70 | −0.97 | * | . | . | 1.00 | 0.99 |
| Met | 138 | . | . | B | . | . | T | . | 0.49 | −0.33 | . | * | . | 0.70 | 0.44 |
| Val | 139 | . | . | B | B | . | . | . | −0.37 | 0.10 | . | * | . | −0.30 | 0.35 |
| Ser | 140 | . | . | B | B | . | . | . | −1.07 | 0.74 | . | . | . | −0.60 | 0.19 |
| Val | 141 | . | . | B | B | . | . | . | −1.48 | 1.14 | . | * | . | −0.60 | 0.17 |
| Pro | 142 | . | . | B | B | . | . | . | −1.18 | 0.91 | . | . | . | −0.60 | 0.30 |
| Val | 143 | . | . | B | B | . | . | . | −1.43 | 0.67 | . | . | . | −0.60 | 0.39 |
| Phe | 144 | . | . | B | B | . | . | . | −0.79 | 0.93 | . | * | . | −0.60 | 0.39 |
| Ser | 145 | . | . | B | B | . | . | . | −1.34 | 0.71 | * | * | . | −0.60 | 0.39 |
| Gln | 146 | . | . | B | B | . | . | . | −0.38 | 0.93 | * | * | . | −0.60 | 0.39 |
| Val | 147 | . | . | B | B | . | . | . | −0.06 | 0.29 | . | * | . | −0.30 | 0.89 |
| Pro | 148 | . | . | B | B | . | . | . | 0.91 | −0.50 | . | * | . | 0.45 | 1.30 |
| Val | 149 | . | . | B | B | . | . | . | 0.80 | −0.89 | . | * | . | 0.75 | 1.47 |
| Arg | 150 | . | . | B | B | . | . | . | 0.43 | −0.60 | . | * | F | 0.90 | 1.63 |
| Arg | 151 | . | . | B | B | . | . | . | 0.22 | −0.67 | . | * | F | 0.75 | 0.57 |
| Arg | 152 | . | . | . | B | T | . | . | 0.87 | −0.67 | . | * | . | 1.15 | 1.18 |
| Leu | 153 | . | . | . | B | T | . | . | 0.87 | −0.89 | * | * | . | 1.00 | 0.93 |
| Cys | 154 | . | . | B | B | . | . | . | 1.51 | −0.46 | * | * | . | 0.58 | 0.73 |

TABLE I-continued

| Res | Position | I | II | III | IV | V | VI | VII | VIII | IX | X | XI | XII | XIII | XIV |
|---|---|---|---|---|---|---|---|---|---|---|---|---|---|---|---|
| Pro | 155 | . | . | . | B | . | . | C | 1.51 | −0.03 | * | * | F | 1.21 | 0.58 |
| Pro | 156 | . | . | . | . | . | . | C | 1.09 | −0.03 | * | . | F | 1.84 | 1.38 |
| Pro | 157 | . | . | . | . | . | T | C | 0.63 | −0.23 | * | . | F | 2.32 | 3.70 |
| Pro | 158 | . | . | . | . | T | T | . | 1.23 | −0.37 | * | . | F | 2.80 | 2.37 |
| Arg | 159 | . | . | . | . | T | T | . | 1.23 | −0.37 | . | . | F | 2.52 | 2.37 |
| Thr | 160 | . | . | . | . | T | T | . | 1.56 | −0.23 | . | . | F | 2.35 | 0.82 |
| Gly | 161 | . | . | B | . | . | T | . | 1.77 | −0.66 | . | * | F | 2.38 | 1.04 |
| Pro | 162 | . | . | B | . | . | T | . | 2.09 | −0.69 | . | * | F | 2.21 | 0.92 |
| Cys | 163 | . | . | B | . | . | T | . | 1.71 | −0.69 | * | * | F | 2.34 | 1.25 |
| Arg | 164 | . | . | B | . | . | T | . | 0.74 | −0.67 | * | * | F | 2.60 | 1.28 |
| Cln | 165 | . | . | B | . | . | . | . | 0.46 | −0.46 | . | * | F | 1.69 | 0.61 |
| Arg | 166 | . | . | B | . | . | . | . | 0.80 | −0.27 | . | * | F | 1.58 | 1.13 |
| Ala | 167 | . | . | B | . | . | . | . | 0.70 | −0.84 | . | * | . | 1.32 | 1.00 |
| Val | 168 | . | . | B | B | . | . | . | 0.48 | −0.36 | . | * | . | 0.56 | 0.83 |
| Met | 169 | . | . | B | B | . | . | . | −0.22 | −0.07 | . | * | . | 0.30 | 0.30 |
| Glu | 170 | . | . | B | B | . | . | . | −1.08 | 0.43 | * | . | . | −0.60 | 0.30 |
| Thr | 171 | . | . | B | B | . | . | . | −1.53 | 0.57 | * | . | . | −0.60 | 0.30 |
| Ile | 172 | A | . | . | B | . | . | . | −1.61 | 0.36 | . | . | . | −0.30 | 0.30 |
| Ala | 173 | A | . | . | B | . | . | . | −1.07 | 0.31 | . | . | . | −0.30 | 0.09 |
| Val | 174 | A | . | . | B | . | . | . | −1.13 | 0.80 | * | . | . | −0.60 | 0.09 |
| Gly | 175 | A | . | . | B | . | . | . | −2.02 | 0.89 | . | . | . | −0.60 | 0.07 |
| Gys | 176 | . | . | B | B | . | . | . | −2.41 | 0.89 | . | . | . | −0.60 | 0.05 |
| Thr | 177 | . | . | B | B | . | . | . | −1.91 | 1.17 | . | . | . | −0.60 | 0.06 |
| Cys | 178 | . | . | B | B | . | . | . | −1.71 | 0.96 | . | . | . | −0.60 | 0.07 |
| Ile | 179 | . | . | B | B | . | . | . | −1.24 | 0.96 | . | . | . | −0.60 | 0.18 |
| Phe | 180 | . | . | B | B | . | . | . | −1.29 | 0.81 | . | . | . | −0.60 | 0.16 |

Among highly preferred fragments in this regard are those that comprise reigons of IL-20 that combine several structural features, such as several of the features set out above.

In another aspect, the invention provides an isolated nucleic acid molecule comprising a polynucleotide which hybridizes under stringent hybridization conditions to a portion of the polynucleotide in a nucleic acid molecule of the invention described above, for instance, the cDNA clone contained in ATCC Deposit No. 209232 or the IL-20-encoding cDNA clone contained in ATCC Deposit No. 209138. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 (e.g., 50) nt of the reference polynucleotide. These are useful as diagnostic probes and primers as discussed above and in more detail below.

By a portion of a polynucleotide of "at least 20 nt in length," for example, is intended 20 or more contiguous nucleotides from the nucleotide sequence of the reference polynucleotide (e.g., the deposited cDNA (ATCC Deposit No. 209232 or ATCC Deposit No. 209138) or the nucleotide sequence as shown in FIG. 1 (SEQ ID NO:1) or in SEQ ID NO:28 or in SEQ ID NO:29). Of course, a polynucleotide which hybridizes only to a poly A sequence (such as the 3' terminal poly(A) tract of the IL-20 cDNA shown in FIG. 1 (SEQ ID NO:1)), or to a complementary stretch of T (or U) residues, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

As indicated, nucleic acid molecules of the present invention which encode an IL-20 polypeptide may include, but are not limited to those encoding the amino acid sequence of the mature polypeptide, by itself; and the coding sequence for the mature polypeptide and additional sequences, such as those encoding the about 20 amino acid leader or secretory sequence, such as a pre-, or pro- or prepro-protein sequence; the coding sequence of the mature polypeptide, with or without the aforementioned additional coding sequences.

Also encoded by nucleic acids of the invention are the above protein sequences together with additional, non-coding sequences, including for example, but not limited to introns and non-coding 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities.

Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described by Gentz and colleagues (*Proc. Natl. Acad. Sci. USA* 86:821–824 (1989)), for instance, hexa-histidine provides for convenient purification of the fusion protein. The "HA" tag is another peptide useful for purification which corresponds to an epitope derived from the influenza hemagglutinin protein, which has been described by Wilson and coworkers (*Cell* 37:767 (1984)). As discussed below, other such fusion proteins include the IL-20 fused to Fc at the N- or C-terminus.

Variant and Mutant Polynucleotides

The present invention further relates to variants of the nucleic acid molecules of the present invention, which encode portions, analogs or derivatives of the IL-20 protein.

Variants may occur naturally, such as a natural allelic variant. By an "allelic variant" is intended one of several alternate forms of a gene occupying a given locus on a chromosome of an organism (*Genes II*, Lewin, B., ed., John Wiley & Sons, New York (1985)). Non-naturally occurring variants may be produced using art-known mutagenesis techniques.

Such variants include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the IL-20 protein or portions thereof. Also especially preferred in this regard are conservative substitutions.

Polynucleotides encoding IL-20 muteins which contain amino acid mutations in regions of the IL-20 polypeptide sequence which exhibit a high degree of sequence identity with several to closely related molecules (see FIGS. 4A and 4B) have a high potential for possessing a change in an IL-20 biological activity. Such preferred embodiments may function as antagonists of innate IL-20 activities.

Most highly preferred are nucleic acid molecules encoding the mature protein having the amino acid sequence shown in SEQ ID NO:2 or the mature IL-20 amino acid sequence encoded by the deposited cDNA clones in ATCC Deposit No. 209232 or ATCC Deposit No. 209138.

Thus, one aspect of the invention provides an isolated nucleic acid molecule comprising a polynucleotide having a nucleotide sequence selected from the group consisting of: (a) a nucleotide sequence encoding the IL-20 polypeptide having the complete amino acid sequence in SEQ ID NO:2 (i.e., positions −20 to 160 of SEQ ID NO:2); (b) a nucleotide sequence encoding the IL-20 polypeptide having the complete amino acid sequence in SEQ ID NO:15 (i.e., positions 1 to 118 of SEQ ID NO:2); (c) a nucleotide sequence encoding the IL-20 polypeptide having the complete amino acid sequence in SEQ ID NO:2 excepting the N-terminal methionine (i.e., positions −19 to 160 of SEQ ID NO:2); (d) a nucleotide sequence encoding the IL-20 polypeptide having the complete amino acid sequence in SEQ ID NO:15 excepting the N-terminal methionine (i.e., positions 2 to 118 of SEQ ID NO:15); (e) a nucleotide sequence encoding the predicted mature IL-20 polypeptide having the amino acid sequence at positions 1 to 160 in SEQ ID NO:2; (f) a nucleotide sequence encoding the predicted mature IL-20 polypeptide having the amino acid sequence at positions 21 to 118 in SEQ ID NO:15; (g) a nucleotide sequence encoding the IL-20 polypeptide having the complete amino acid sequence encoded by the cDNA clone contained in ATCC Deposit No. 209232; (h) a nucleotide sequence encoding the IL-20 polypeptide having the complete amino acid sequence encoded by the cDNA clone contained in ATCC Deposit No. 209138; (i) a nucleotide sequence encoding the IL-20 polypeptide having the complete amino acid sequence excepting the N-terminal methionine encoded by the cDNA clone contained in ATCC Deposit No. 209232; (j) a nucleotide sequence encoding the IL-20 polypeptide having the complete amino acid sequence excepting the N-terminal methionine encoded by the cDNA clone contained in ATCC Deposit No. 209138; (k) a nucleotide sequence encoding the mature IL-20 polypeptide having the amino acid sequence encoded by the cDNA clone contained in ATCC Deposit No. 209232; (l) a nucleotide sequence encoding the mature IL-20 polypeptide having the amino acid sequence encoded by the cDNA clone contained in ATCC Deposit No. 209138; and, (m) a nucleotide sequence complementary to any of the nucleotide sequences in (a), (b), (c), (d), (e), (f), (g), (h), (i), (j), (k) or (l), above.

Further embodiments of the invention include isolated nucleic acid molecules that comprise a polynucleotide having a nucleotide sequence at least 90% identical to (that is to say, at most 10% different from), and more preferably at least 95%, 96%, 97%, 98% or 99% identical to (that is to say, at most 5%, 4%, 3%, 2% or 1% different from), any of the nucleotide sequences in (a), (b), (c), (d), (e), (f), (g), (h), (i), (j), (k), (l) or (m), above, or a polynucleotide which hybridizes under stringent hybridization conditions to a polynucleotide in (a), (b), (c), (d), (e), (f), (g), (h), (i), (j), (k), (l) or (m), above. This polynucleotide which hybridizes does not hybridize under stringent hybridization conditions to a polynucleotide having a nucleotide sequence consisting of only A residues or of only T residues. An additional nucleic acid embodiment of the invention relates to an isolated nucleic acid molecule comprising a polynucleotide which encodes the amino acid sequence of an epitope-bearing portion of an IL-20 polypeptide having an amino acid sequence in (a), (b), (c), (d), (e), (f), (g), (h), (i), (j), (k) or (l), above. A further nucleic acid embodiment of the invention relates to an isolated nucleic acid molecule comprising a polynucleotide which encodes the amino acid sequence of an IL-20 polypeptide having an amino acid sequence which contains at least one conservative amino acid substitution, but not more than 50 conservative amino acid substitutions, even more preferably, not more than 40 conservative amino acid substitutions, still more preferably not more than 30 conservative amino acid substitutions, and still even more preferably not more than 20 conservative amino acid substitutions. Of course, in order of ever-increasing preference, it is highly preferable for a polynucleotide which encodes the amino acid sequence of an IL-20 polypeptide to have an amino acid sequence which contains not more than 10, 9, 8, 7, 6, 5, 4, 3, 2 or 1 conservative amino acid substitutions.

The present invention also relates to recombinant vectors, which include the isolated nucleic acid molecules of the present invention, and to host cells containing the recombinant vectors, as well as to methods of making such vectors and host cells and for using them for production of IL-20 polypeptides or peptides by recombinant techniques.

In addition to encompassing host cells containing the vector constructs discussed herein, the invention also encompasses primary, secondary, and immortalized host cells of vertebrate origin, particularly those of mammalian origin, that have been engineered to delete or replace endogenous genetic material (e.g. IL-20 coding sequence), and/or to include genetic material (e.g. heterologous polynucleotide sequences) that is operably associated with IL-20 polynucleotides of the invention, and which activates, alters, and/or amplifies endogenous IL-20 polynucleotides. For example, techniques known in the art may be used to operably associate heterologous control regions (e.g. promoter and/or enhancer) and endogenous IL-20 polynucleotide sequences via homologous recombination (see, e.g. U.S. Pat. No. 5,641,670, issued Jun. 24, 1997; Internation Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra, et al., Nature 342:435–438 (1989), the disclosures of each of which are hereby incorporated by reference in their entireties).

By a polynucleotide having a nucleotide sequence at least, for example, 95% "identical" to a reference nucleotide sequence encoding an IL-20 polypeptide is intended that the nucleotide sequence of the polynucleotide is identical to the reference sequence except that the polynucleotide sequence may include up to five point mutations per each 100 nucleotides of the reference nucleotide sequence encoding the IL-20 polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. The query sequence may be an entire sequence shown as SEQ ID NO:1 or any fragement specified as described herein.

As a practical matter, whether any particular nucleic acid molecule is at least 90%, 95%, 96%, 97%, 98% or 99% identical to, for instance, the nucleotide sequence shown in FIG. 1 or to the nucleotides sequence of the deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman to find the best segment of homology between two sequences (*Advances in Applied Mathematics* 2:482489 (1981)). When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed. A preferred method for determing the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237–245). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identify are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to made for the purposes of the present invention.

The present application is directed to nucleic acid molecules at least 90%, 95%, 96%, 97%, 98% or 99% identical to the nucleic acid sequence shown in FIG. 1 (SEQ ID NO:1), SEQ ID NO:28, or SEQ ID NO:29, or to the nucleic acid sequence of the deposited cDNA (ATCC Deposit No. 209232 and ATCC Deposit No. 209138), irrespective of whether they encode a polypeptide having IL-20 activity. This is because even where a particular nucleic acid molecule does not encode a polypeptide having IL-20 activity, one of skill in the art would still know how to use the nucleic acid molecule, for instance, as a hybridization probe or a polymerase chain reaction (PCR) primer. Uses of the nucleic acid molecules of the present invention that do not encode a polypeptide having IL-20 activity include, inter alia, (1) isolating the IL-20 gene or allelic variants thereof in a cDNA library; (2) in situ hybridization (e.g., "FISH") to metaphase chromosomal spreads to provide precise chromosomal location of the IL-20 gene, as described by Verma and colleagues (*Human Chromosomes: A Manual of Basic Techniques*, Pergamon Press, New York (1988)); and Northern Blot analysis for detecting IL-20 mRNA expression in specific tissues.

Preferred, however, are nucleic acid molecules having sequences at least 90%, 95%, 96%, 97%, 98% or 99% identical to the nucleic acid sequence shown in FIG. 1 (SEQ ID NO:1), SEQ ID NO:28, SEQ ID NO:29, or to the nucleic acid sequence of the deposited cDNA (ATCC Deposit No. 209232 and ATCC Deposit No. 209138) which do, in fact, encode a polypeptide having IL-20 protein activity. By "a polypeptide having IL-20 activity" is intended polypeptides exhibiting activity similar, but not necessarily identical, to an activity of the mature IL-20 protein of the invention, as measured in a particular biological assay. For example, the IL-20 protein of the present invention modulates IL-6 secretion from NIH-3T3 cells. An in vitro ELISA assay which quantitates the amount of IL-6 secreted from cells in response to treatment with cytokines or the soluble extracellular domains of cytokine receptors has been described (Yao, Z., et al., *Immunity* 3:811–821 (1995)). Briefly, the assay involves plating the target cells at a density of approximately $5\times10^6$ cells/mL in a volume of 500 $\mu$L in the wells of a 24 well flat-bottomed culture plate (Costar). The cultures are then treated with various concentrations of the cytokine or the soluble extracellular domain of cytokine receptor in question The cells are then cultured for 24 hours at 37° C. At this time, 50 $\mu$L of supernatant is removed and assayed for the quantity of IL-6 essentially as described by the manufacturer (Genzyme, Boston, Mass.). IL-6 levels are then calculated by reference to a standard curve constructed with recombinant IL-17 cytokine. Such activity is useful for determining the level of IL-20-mediated IL-6 secretion.

IL-20 protein modulates immune system cell proliferation and differentiation in a dose-dependent manner in the above-described assay. Thus, "a polypeptide having IL-20 protein activity" includes polypeptides that also exhibit any of the same stimulatory activities in the above-described assays in a dose-dependent manner. Although the ° of dose-dependent activity need not be identical to that of the IL-20 protein, preferably, "a polypeptide having IL-20 protein activity" will exhibit substantially similar dose-dependence in a given activity as compared to the IL-20 protein (i.e., the candidate polypeptide will exhibit greater activity or not more than about 25-fold less and, preferably, not more than about tenfold less activity relative to the reference IL-20 protein).

Lymphocyte proliferation is another in vitro assay which may be performed to determine the activity of IL-20. For example, Yao and colleagues (*Immunity* 3:811–821 (1995)) have recently described an in vitro assay for determining the effects of various cytokines and soluble cytokine receptors on the proliferation of murine leukocytes. Briefly, lymphoid organs are harvested aseptically, lymphocytes are isolated from the harvested organs, and the resulting collection of lymphoid cells are suspended in standard culture medium as described by Fanslow and coworkers (J. Immunol. 147:535–5540 (1991)). The lymphoid cell suspensions may then be divided into several different subclasses of lymphoid cells including splenic T-cells, lymph node B-cells, $CD4^+$ and $CD8^+$ T-cells, and mature adult thymocytes. For splenic T-cells, spleen cell suspensions ($200\times10^6$ cells) are incubated with CD11b mAb and class II MHC mAb for 30 mm at 4° C., loaded on a T-cell purification column (Pierce, Rockford, Ill.), and the T-cells eluted according to the manufacturer's instructions. Using this method, purity of the resulting T-cell populations should be >95% $CD3^+$ and <1% $sIgM^+$. For purification of lymph node subsets, B-cells are removed from by adherence to tissue culture dishes previously coated with goat anti-mouse IgG (10 $\mu$g/mL). Remaining cells were then incubated with anti-CD4 or anti-CD8 for 30 min at 4° C. then washed and placed on tissue culture dishes previously coated with goat anti-rat IgG (20 $\mu$g/mL). After 45 min, nonadherent cells are removed and tested for purity by flow cytometry. CD4 and surface Ig-depleted cells should be >90% TCR-ab, $CD8^+$, whereas CD8 and surface Ig-depleted cells should be >95% TCR-ab, $CD4^+$. Finally, to enrich for mature adult thymocytes, cells are suspended at $10^8$/mL in 10% anti-HSA and 10% low tox rabbit complement (Cedarlane, Ontario, Canada), incubated for 45 min at 37° C., and remaining viable cells isolated over Ficoll-Hypaque (Pharmacia, Piscataway, N.J.). This procedure should yield between 90 and 95% $CD3^{hi}$ cells that are either $CD4^+8^-$ or $CD4^-8^+$.

To analyze the proliferative response of the above-described primary cell cultures, in vitro proliferation assays are set up in round bottom or flat bottom 96-well plates using $0.5–1.5\times10^5$ cells/well. For stimulation, T-cells are incubated with suboptimal concentrations (0.25–0.5 $\mu$g/mL) of Con A (Sigma, St. Louis, Mo.), PHA (0.25–0.5%; Difco, Detroit, Mich.), immobilized anti-CD3, or immobilized anti-TCR-ab. Anti-CD3 and anti-TCR-ab are immobilized for >2 hours at 37° C. before the addition of effector cells. Incubations are done in the presence and absence of fixed CV-1/EBNA cells transfected with IL 17RLP, muteins thereof, a control vector, or a control antigen such as rCD40L (Armitage, et al., *Nature* 357:80 (1992)); Spriggs, et a., *J. Exp. Med.* 176:1543 (1992)). Surface expression of CD40L is monitored by flow cytometry using a human CD40-Fc fusion protein. Cell cultures are pulsed overnight with [$^3$H]-thymidine (1 $\mu$Ci/well) for the last 18 hours of a 3 day culture. Labeled cultures are then harvested on a 96-well Inotech harvester and radioactive counts detected using a scintillation counter.

Like other cytokines, IL-20 exhibits activity on leukocytes including for example monocytes, lymphocytes and neutrophils. For this reason IL-20 is active in directing the proliferation and differentiation of these cell types. Such activity is useful for immune enhancement or suppression, myeloprotection, stem cell mobilization, acute and chronic inflammatory control and treatment of leukemia. Assays for measuring such activity are well known in the art (Peters, et al., *Immun. Today* 17:273 (1996); Young, et al., *J. Exp. Med.* 182:1111 (1995); Caux, et al., *Nature* 390:258 (1992); and Santiago-Schwarz, et al., *Adv. Exp. Med. Biol.* 378:7 (1995).

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the deposited cDNA or the nucleic acid sequence shown in FIG. 1 (SEQ ID NO:1) will encode a polypeptide "having IL-20 protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having IL-20 protein activity. This is because the skilled artisan is fully aware of amino acid substitutions that are either less likely or not likely to significantly effect protein function (e.g., replacing one aliphatic amino acid with a second aliphatic amino acid), as further described below.

Vectors and Host Cells

The present invention also relates to vectors which include the isolated DNA molecules of the present invention, host cells which are genetically engineered with the recombinant vectors, and the production of IL-20 polypeptides or fragments thereof by recombinant techniques. The vector may be, for example, a phage, plasmid, viral or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert should be operatively linked to an appropriate promoter, such as the phage lambda PL promoter, the *E. coli* lac, trp, phoA and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Representative examples of appropriate hosts include, but are not limited to, bacterial cells, such as *E. coli*, Streptomyces and *Salmonella typhimurium* cells; fungal cells, such as yeast cells; insect cells such as Drosophila S2 and Spodoptera Sf9 cells; animal cells such as CHO, COS, 293 and Bowes melanoma cells; and plant cells. Appropriate culture mediums and conditions for the above-described host cells are known in the art.

Vectors preferred for use in bacteria include pHE4-5, pQE70, pQE60 and pQE-9 (QIAGEN, Inc., supra); pBS vectors, Phagescript vectors, Bluescript vectors, pNH8A, pNH16a, pNH18A, pNH46A (Stratagene); and ptrc99a, pKK223-3, pKK233-3, pDR540, pRIT5 (Pharmacia). Among preferred eukaryotic vectors are pWLNEO, pSV2CAT, pOG44, pXT1, and pSG (Stratagene); and pSVK3, pBPV, pMSG and pSVL (Pharmacia). Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals (for example, Davis, et al., *Basic Methods In Molecular Biology* (1986)).

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to stabilize and purify proteins. For example, EP-A-O 464 533 (Canadian counterpart 2045869) discloses fusion proteins comprising various portions of constant region of immunoglobulin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as hIL-5, have been fused with Fc portions for the purpose of high-throughput screening assays to identify antagonists of hIL-5 (Bennett, D., et al., *J. Molecular Recognition* 8:52–58 (1995); Johanson, K., et al., *J. Biol. Chem.* 270:9459–9471 (1995)).

The IL-20 protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins this prokaryotic removal process is inefficient, depending on the nature of the amino acid to which the N-terminal methionine is covalently linked.

Polypeptides and Fragments

The invention further provides an isolated IL-20 polypeptide having the amino acid sequence encoded by the deposited cDNA (ATCC Deposit No. 209232 and ATCC Deposit No. 209138), or the amino acid sequence in SEQ ID NO:2, or the amino acid sequence in SEQ ID NO:15, or a peptide or polypeptide comprising a portion of the above polypeptides.

Variant and Mutant Polypeptides

To improve or alter the characteristics of IL-20 polypeptides, protein engineering may be employed. Recombinant DNA technology known to those skilled in the art can be used to create novel mutant proteins or muteins including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions.

N-Terminal and C-Terminal Deletion Mutants

For instance, for many proteins, including the extracellular domain of a membrane associated protein or the mature form(s) of a secreted protein, it is known in the art that one or more amino acids may be deleted from the N-terminus or C-terminus without substantial loss of biological function. For instance, Ron and colleagues (*J. Biol. Chem.*, 268:2984–2988 (1993)) reported modified KGF proteins that had heparin binding activity even if 3, 8, or 27 N-terminal amino acid residues were missing. In the present case, since the protein of the invention is a member of the interleukin-17 polypeptide family, deletions of N-terminal amino acids up to the lysine at position 10 of SEQ ID NO:2 may retain some biological activity such as receptor binding or modulation of target cell activities.

However, even if deletion of one or more amino acids from the N-terminus of a protein results in modification or loss of one or more biological functions of the protein, other biological activities may still be retained. Thus, the ability of the shortened protein to induce and/or bind to antibodies which recognize the complete or mature form of the protein generally will be retained when less than the majority of the residues of the complete or mature form of the protein are removed from the N-terminus. Whether a particular polypeptide lacking N-terminal residues of a complete protein retains such immunologic activities can readily be determined by routine methods described herein and otherwise known in the art.

Accordingly, the present invention further provides polypeptides having one or more residues deleted from the amino terminus of the amino acid sequence of the IL-20 shown in SEQ ID NO:2, up to the lysine residue at position number 10, and polynucleotides encoding such polypeptides. In particular, the present invention provides polypeptides comprising the amino acid sequence of residues $n^1$-160 of SEQ ID NO:2, where $n^1$ is an integer in the range of −20 to 10, and 10 is the position of the first residue from the N-terminus of the complete IL-20 polypeptide (shown in SEQ ID NO:2) believed to be required for receptor binding activity of the IL-20 protein.

More in particular, the invention provides polynucleotides encoding polypeptides having the amino acid sequence of residues of −20–160, −19–160, −18–160, −17–160, −16–160, −15–160, −14–160, −13–160, −12–160, −11–160, −10–160, −9–160, −8–160, −7–160, −6–160, −5–160, −4–160, −3–160, −2–160, −1–160, 1–160, 2–160, 3–160, 4–160, 5–160, 6–160, 7–160, 8–160, 9–160, and 10–160, of SEQ ID NO:2. Polynucleotides encoding these polypeptides also are provided.

Similarly, many examples of biologically functional C-terminal deletion muteins are known. For instance, Interferon gamma shows up to ten times higher activities by deleting 8–10 amino acid residues from the carboxy terminus of the protein (Dobeli, et al., *J. Biotechnology* 7:199–216 (1988)). In the present case, since the protein of the invention is a member of the interleukin-17 polypeptide family, deletions of C-terminal amino acids up to the cysteine at position 158 of SEQ ID NO:2 may retain some biological activity such as receptor binding or modulation of target cell activities, for chemokines.

However, even if deletion of one or more amino acids from the C-terminus of a protein results in modification of loss of one or more biological functions of the protein, other biological activities may still be retained. Thus, the ability of the shortened protein to induce and/or bind to antibodies which recognize the complete or mature form of the protein generally will be retained when less than the majority of the residues of the complete or mature form of the protein are removed from the C-terminus. Whether a particular polypeptide lacking C-terminal residues of a complete protein retains such immunologic activities can readily be determined by routine methods described herein and otherwise known in the art.

Accordingly, the present invention further provides polypeptides having one or more residues from the carboxy terminus of the amino acid sequence of the IL-20 shown in SEQ ID NO:2, up to the cysteine residue at position 158 of SEQ ID NO:2, and polynucleotides encoding such polypeptides. In particular, the present invention provides polypeptides having the amino acid sequence of residues −20-$m^1$ of the amino acid sequence in SEQ ID NO:2, where $m^1$ is any integer in the range of 158 to 160, and residue 158 is the position of the first residue from the C-terminus of the complete IL-20 polypeptide (shown in SEQ ID NO:2) believed to be required for receptor binding activity of the IL-20 protein.

More in particular, the invention provides polynucleotides encoding polypeptides having the amino acid sequence of residues −20–158, −20–159, and −20–160 of SEQ ID NO:2. Polynucleotides encoding these polypeptides also are provided.

The invention also provides polypeptides having one or more amino acids deleted from both the amino and the carboxyl termini, which may be described generally as having residues $n^1$-$m^1$ of SEQ ID NO:2, where n and m are integers as described above.

Also included are a nucleotide sequence encoding a polypeptide consisting of a portion of the complete IL-20 amino acid sequence encoded by the cDNA clone contained in ATCC Deposit No. 209232, where this portion excludes from 1 to about 30 amino acids from the amino terminus of the complete amino acid sequence encoded by the cDNA clone contained in ATCC Deposit No. 209232, or from 1 to about 3 amino acids from the carboxy terminus, or any combination of the above amino terminal and carboxy terminal deletions, of the complete amino acid sequence encoded by the cDNA clone contained in ATCC Deposit No. 209232. Polynucleotides encoding all of the above deletion mutant polypeptide forms also are provided.

As mentioned above, even if deletion of one or more amino acids from the N-terminus of a protein results in modification of loss of one or more biological functions of the protein, other biological activities may still be retained. Thus, the ability of the shortened IL-20 mutein to induce and/or bind to antibodies which recognize the complete or mature of the protein generally will be retained when less than the majority of the residues of the complete or mature protein are removed from the N-terminus. Whether a particular polypeptide lacking N-terminal residues of a complete protein retains such immunologic activities can readily be determined by routine methods described herein and otherwise known in the art. It is not unlikely that an IL-20 mutein with a large number of deleted N-terminal amino acid residues may retain some biological or immunogenic activities. In fact, peptides composed of as few as six IL-20 amino acid residues may often evoke an immune response.

Accordingly, the present invention further provides polypeptides having one or more residues deleted from the amino terminus of the IL-20 amino acid sequence shown in FIG. 1 (SEQ ID NO:2), up to the glycine residue at position number 175 and polynucleotides encoding such polypeptides. In particular, the present invention provides polypeptides comprising the amino acid sequence of residues $n^1$-180 of FIG. 1 (SEQ ID NO:2), where $n^1$ is an integer in the range of 2 to 175, and 176 is the position of the first residue from the N-terminus of the complete IL-20 polypeptide believed to be required for at least immunogenic activity of the IL-20 protein.

More in particular, the invention provides polynucleotides encoding polypeptides comprising, or alternatively consisting of, the amino acid sequence of residues of D-2 to F-180; W-3 to F-180; P-4 to F-180; H-5 to F-180; N-6 to F-180; L-7 to F-180; L-8 to F-180; L-10 to F-180; L-11 to F-180; T-12 to F-180; I-13 to F-180; S-14 to F-180; I-15 to F-180; F-16 to F-180; L-17 to F-180; G-18 to F-180; L-19 to F-180; G-20 to F-180; Q-21 to F-180; P-22 to F-180; R-23 to F-180; S-24 to F-180; P-25 to F-180; K-26 to F-180; S-27 to F-180; K-28 to F-180; R-29 to F-180; K-30 to F-180; G-31 to F-180; Q-32 to F-180; G-33 to F-180; R-34 to F-180; P-35 to F-180; G-36 to F-180; P-37 to F-180; L-38 to F-180; A-39 to F-180; P-40 to F-180; G-41 to F-180; P-42 to F-180; H-43 to F-180; Q-44 to F-180; V-45 to F-180; P-46 to F-180; L-47 to F-180; D-48 to F-180; L-49 to F-180; V-50 to F-180; S-51 to F-180; R-52 to F-180; M-53 to F-180; K-54 to F-180; P-55 to F-180; Y-56 to F-180; A-57 to F-180; R-58 to F-180; M-59 to F-180; E-60 to F-180; E-61 to F-180; Y-62 to F-180; E-63 to F-180; R-64 to F-180; N-65 to F-180; I-66 to F-180; E-67 to F-180; E-68 to F-180; M-69 to F-180; V-70 to F-180; A-71 to F-180; Q-72 to F-180; L-73 to F-180; R-74 to F-180; N-75 to F-180; S-76 to F-180; S-77 to F-180; E-78 to F-180; L-79 to F-180; A-80 to F-180; Q-81 to F-180; R-82 to F-180; K-83 to F-180; C-84 to F-180; E-85 to F-180; V-86 to F-180; N-87 to F-180; L-88 to F-180; Q-89 to F-180; L-90 to F-180; W-91 to F-180; M-92 to F-180; S-93 to F-180; N-94 to F-180; K-95 to F-180; R-96 to F-180; S-97 to F-180; L-98 to F-180; S-99 to F-180; P-100 to F-180; W-101 to F-180; G-102 to F-180; Y-103 to F-180; S-104 to F-180; I-105 to F-180; N-106 to F-180; H-107 to F-180; D-108 to F-180; P-109 to F-180; S-110 to F-180; R-111 to F-180; I-112 to F-180; P-113 to F-180; V-114 to F-180; D-115 to F-180; L-116 to F-180; P-117 to F-180; E-118 to F-180; A-119 to F-180; R-120 to F-180; C-121 to F-180; R-120 to F-180; L-122 to F-180; C-123 to F-180; L-124 to F-180; G-125 to F-180; C-126 to F-180; V-127 to F-180; N-128 to F-180; P-129 to F-180; F-130 to F-180; T-131 to F-180; M-132 to F-180; Q-133 to F-180; E-134 to F-180; D-135 to F-180; R-136 to F-180; S-137 to F-180; M-138 to F-180; V-139 to F-180; S-140 to F-180; V-141 to F-180; P-142 to F-180; V-143 to F-180; F-144 to F-180; S-145 to F-180; Q-146 to F-180; V-147 to F-180; P-148 to F-180; V-149 to F-180; R-150 to F-180; R-151 to F-180; R-152 to F-180; L-153 to F-180; C-154 to F-180; P-155 to F-180; P-156 to F-180; P-157 to F-180; P-158 to F-180; R-159 to F-180; T-160 to F-180; G-161 to F-180; P-162 to F-180; C-163 to F-180; R-164 to F-180; Q-165 to F-180; R-166 to F-180; A-167 to F-180; V-168 to F-180; M-169 to F-180; E-170 to F-180; T-171 to F-180; I-172 to F-180; A-173 to F-180; V-174 to F-180; and G-175 to F-180 of the IL-20 sequence shown in FIG. 1 (which is identical to the sequence shown as SEQ ID NO:2, with the exception that the amino acid residues in FIG. 1 are numbered consecutively from 1 through 180 from the N-terminus to the C-termninus, while the amino acid residues in SEQ ID NO:2 are numbered consecutively from −20 through 160 to reflect the position of the predicted signal peptide). Polynucleotides encoding these polypeptides are also encompassed by the invention.

Also as mentioned above, even if deletion of one or more amino acids from the C-terminus of a protein results in modification of loss of one or more biological functions of the protein, other biological activities may still be retained. Thus, the ability of the shortened IL-20 mutein to induce and/or bind to antibodies which recognize the complete or mature of the protein generally will be retained when less than the majority of the residues of the complete or mature protein are removed from the C-terminus. Whether a particular polypeptide lacking C-terminal residues of a complete protein retains such immunologic activities can readily be determined by routine methods described herein and otherwise known in the art. It is not unlikely that an IL-20 mutein with a large number of deleted C-terminal amino acid residues may retain some biological or immungenic activities. In fact, peptides composed of as few as six IL-20 amino acid residues may often evoke an immune response.

Accordingly, the present invention further provides polypeptides having one or more residues deleted from the carboxy terminus of the amino acid sequence of the IL-20 shown in FIG. 1 (SEQ ID NO:2), up to the asparagine residue at position number 6, and polynucleotides encoding such polypeptides. In particular, the present invention provides polypeptides comprising the amino acid sequence of residues 1-$m^1$ of FIG. 1 (SEQ ID NO:2), where $m^1$ is an integer in the range of 6 to 179, and 6 is the position of the first residue from the C-terminus of the complete IL-20 polypeptide believed to be required for at least immunogenic activity of the IL-20 protein.

More in particular, the invention provides polynucleotides encoding polypeptides comprising, or alternatively consisting of, the amino acid sequence of residues M-1 to I-179; M-1 to C-178; M-1 to T-177; M-1 to C-176; M-1 to G-175; M-1 to V-174; M-1 to A-173; M-1 to I-172; M-1 to T-171; M-1 to E-170; M-1 to M-169; M-1 to V-168; M-1 to A-167; M-1 to R-166; M-1 to Q-165; M-1 to R-164; M-1 to C-163; M-1 to P-162; M-1 to G-161; M-1 to T-160; M-1 R-159; M-1 to P-158; M-1 to P-157; M-1 to P-156; M-1 to P-155; M-1 to C-154; M-1 to L-153; M-1 to R-152; M-1 to R-151; M-1 to R-150; M-1 to V-149; M-1 to P-148; M-1 to V-147; M-1 to Q-146; M-1 to S-145; M-1 to F-144; M-1 to V-143; M-1 to P-142; M-1 to V-141; M-1 to S-140; M-1 to V-139; M-1 to M-138; M-1 to S-137; M-1 to R-136; M-1 to D-135; M-1 to E-134; M-1 to Q-133; M-1 to M-132; M-1 to T-131; M-1 to F-130; M-1 to P-129; M-1 to N-128; M-1 to V-127; M-1 to C-126; M-1 to G-125; M-1 to L-124; M-1 to C-123; M-1 to L-122; M-1 to C-121; M-1 to R-120; M-1 to A-119; M-1 to E-118; M-1 to P-117; M-1 to L-116; M-1 to D-115; M-1 to V-114; M-1 to P-113; M-1 to I-112; M-1 to R-111; M-1 to S-110; M-1 to P-109; M-1 to D-108; M-1 to H-107; M-1 to N-106; M-1 to I-105; M-1 to S-104; M-1 to Y-103; M-1 to G-102; M-1 to W-101; M-1 to P-100; M-1 to S-99; M-1 to L-98; M-1 to S-97; M-1 to R-96; M-1 to K-95; M-1 to N-94; M-1 to S-93; M-1 to M-92; M-1 to W-91; M-1 to L-90; M-1 to Q-89; M-1 to L-88; M-1 to N-87; M-1 to V-86; M-1 to E-85; M-1 to C-84; M-1 to K-83; M-1 to R-82; M-1 to Q-81; M-1 to A-80; M-1 to L-79; M-1 to E-78; M-1 to S-77; M-1 to S-76; M-1 to N-75; M-1 to R-74; M-1 to L-73; M-1 to Q-72; M-1 to A-71; M-1 to V-70; M-1 to M-69; M-1 to E-68; M-1 to E-67; M-1 to I-66; M-1 to N-65; M-1 to R-64; M-1 to E-63; M-1 to Y-62; M-1 to E-61; M-1 to E-60; M-1 to M-59; M-1 to R-58; M-1 to A-57; M-1 to Y-56; M-1 to P-55; M-1 to K-54; M-1 to M-53; M-1 to R-52; M-1 to S-51; M-1 to V-50; M-1 to L-49; M-1 to D-48; M-1 to L-47; M-1 to P-46; M-1 to V-45; M-1 to Q-44; M-1 to H-43; M-1 to P-42; M-1 to G-41; M-1 to P-40; M-1 to A-39; M-1 to L-38; M-1 to P-37; M-1 to G-36; M-1 to P-35; M-1 to R-34; M-1 to G-33; M-1 to Q-32; M-1 to G-31; M-1 to K-30; M-1 to R-29; M-1 to K-28; M-1 to S-27; M-1 to K-26; M-1 to P-25; M-1 to S-24; M-1 to R-23; M-1 to P-22; M-1 to Q-21; M-1 to G-20; M-1 to L-19; M-1 to G-18; M-1 to L-17; M-1 to F-16; M-1 to I-15; M-1 to S-14; M-1 to I-13; M-1 to T-12; M-1 to L-11; M-1 to L-10; M-1 to F-9; M-1 to L-8; M-1 to L-7; and M-1 to N-6 of the sequence of the IL-20 sequence shown in FIG. 1 (which is identical to the sequence shown as SEQ ID NO:2, with the exception that the amino acid residues in FIG. 1 are numbered consecutively from 1 through 180 from the N-terminus to the C-terminus, while the amino acid residues in SEQ ID NO:2 are numbered consecutively from −20 through 160 to reflect the position of the predicted signal peptide). Polynucleotides encoding these polypeptides also are provided.

The invention also provides polypeptides having one or more amino acids deleted from both the amino and the carboxyl termini of an IL-20 polypeptide, which may be described generally as having residues $n^1$-$m^1$ of FIG. 1 (SEQ ID NO:2), where $n^1$ and $m^1$ are integers as described above.

Also as mentioned above, even if deletion of one or more amino acids from the N-terminus of a protein results in modification of loss of one or more biological functions of the protein, other biological activities may still be retained. Thus, the ability of the shortened IL-20 mutein to induce and/or bind to antibodies which recognize the complete or mature of the protein generally will be retained when less than the majority of the residues of the complete or mature protein are removed from the N-termninus. Whether a particular polypeptide lacking N-terminal residues of a complete protein retains such immunologic activities can readily be determined by routine methods described herein and otherwise known in the art. It is not unlikely that an IL-20 mutein with a large number of deleted N-terminal amino acid residues may retain some biological or immungenic activities. In fact, peptides composed of as few as six IL-20 amino acid residues may often evoke an immune response.

Accordingly, the present invention further provides polypeptides having one or more residues deleted from the amino terminus of the IL-20 amino acid sequence shown in SEQ ID NO:15, up to the isoleucine residue at position number 112 and polynucleotides encoding such polypeptides. In particular, the present invention provides polypeptides comprising the amino acid sequence of residues $n^3$-118 of SEQ ID NO:15, where $n^3$ is an integer in the range of 2 to 112, and 113 is the position of the first residue from the N-terminus of the IL-20 polypeptide believed to be required for at least immunogenic activity of the IL-20 protein.

More in particular, the invention provides polynucleotides encoding polypeptides comprising, or alternatively consisting of, the amino acid sequence of residues of D-2 to E-118; W-3 to E-118; P-4 to E-118; H-5 to E-118; N-6 to E-118; L-7 to E-118; L-8 to E-118; F-9 to E-118; L-10 to E-118; L-11 to E-118; T-12 to E-118; I-13 to E-118; S-14 to E-118; I-15 to E-118; F-16 to E-118; L-17 to E-118; G-18 to E-118; L-19 to E-118; G-20 to E-118; Q-21 to E-118; P-22 to E-118; R-23 to E-118; S-24 to E-118; P-25 to E-118; K-26 to E-118; S-27 to E-118; K-28 to E-118; R-29 to E-118; K-30 to E-118; G-31 to E-118; Q-32 to E-118; G-33 to E-118; R-34 to E-118; P-35 to E-118; G-36 to E-118; P-37 to E-118; L-38 to E-118; A-39 to E-118; P-40 to E-118; G-41 to E-118; P-42 to E-118; H-43 to E-118; Q-44 to E-118; V-45 to E-118; P-46 to E-118; L-47 to E-118; D-48 to E-118; L-49 to E-118; V-50 to E-118; S-51 to E-118; R-52 to E-118; M-53 to E-118; K-54 to E-118; P-55 to E-118; Y-56 to E-118; A-57 to E-118; R-58 to E-118; M-59 to E-118; E-60 to E-118; E-61 to E-118; Y-62 to E-118; E-63 to E-118; R-64 to E-118; N-65 to E-118; I-66 to E-118; E-67 to E-118; E-68 to E-118; M-69 to E-118; V-70 to E-118; A-71 to E-118; Q-72 to E-118; L-73 to E-118; R-74 to E-118; N-75 to E-118; S-76 to E-118; S-77 to E-118; E-78 to E-118; L-79 to E-118; A-80 to E-118; Q-81 to E-118; R-82 to E-118; K-83 to E-118; C-84 to E-118; E-85 to E-118; V-86 to E-118; N-87 to E-118; L-88 to E-118; Q-89 to E-118; L-90 to E-118; W-91 to E-118; M-92 to E-118; S-93 to E-118; N-94 to E-118; K-95 to E-118; R-96 to E-118; S-97 to E-118; L-98 to E-118; S-99 to E-118; P-100 to E-118; W-101 to E-118; G-102 to E-118; Y-103 to E-118; S-104 to E-118; I-105 to E-118; N-106 to E-118; H-107 to E-118; D-108 to E-118; P-109 to E-118; E-118; R-111 to E-118; and I-112 to E-118 of the IL-20 sequence shown in SEQ ID NO:15. Polynucleotides encoding these polypeptides are also encompassed by the invention.

Also as mentioned above, even if deletion of one or more amino acids from the C-terminus of a protein results in modification of loss of one or more biological functions of the protein, other biological activities may still be retained. Thus, the ability of the shortened IL-20 mutein to induce and/or bind to antibodies which recognize the complete or mature of the protein generally will be retained when less than the majority of the residues of the complete or mature protein are removed from the C-terminus. Whether a particular polypeptide lacking C-terminal residues of a complete protein retains such immunologic activities can readily be determined by routine methods described herein and otherwise known in the art. It is not unlikely that an IL-20 mutein with a large number of deleted C-terminal amino acid residues may retain some biological or immungenic activities. In fact, peptides composed of as few as six IL-20 amino acid residues may often evoke an immune response.

Accordingly, the present invention further provides polypeptides having one or more residues deleted from the carboxy terminus of the amino acid sequence of the IL-20 shown in SEQ ID NO:15, up to the asparagine residue at position number 6, and polynucleotides encoding such polypeptides. In particular, the present invention provides polypeptides comprising the amino acid sequence of residues 1-$m^3$ of SEQ ID NO:15, where $m^3$ is an integer in the range of 6 to 118, and 6 is the position of the first residue from the C-terminus of the IL-20 polypeptide believed to be required for at least immunogenic activity of the IL-20 protein.

More in particular, the invention provides polynucleotides encoding polypeptides comprising, or alternatively consisting of, the amino acid sequence of residues M-1 to E-118; M-1 to P-117; M-1 to L-116; M-1 to D-115; M-1 to V-114; M-1 to P-113; M-1 to I-112; M-1 to R-111; M-1 to S-110; M-1 to P-109; M-1 to D-108; M-1 to H-107; M-1 to N-106; M-1 to I-105; M-1 to S-104; M-1 to Y-103; M-1 to G-102; M-1 to W-101; M-1 to P-100; M-1 to S-99; M-1 to L-98; M-1 to S-97; M-1 to R-96; M-1 to K-95; M-1 to N-94; M-1 to S-93; M-1 to M-92; M-1 to W-91; M-1 to L-90; M-1 to Q-89; M-1 to L-88; M-1 to N-87; M-1 to V-86; M-1 to E-85; M-1 to C-84; M-1 to K-83; M-1 to R-82; M-1 to Q-81; M-1 to A-80; M-1 to L-79; M-1 to E-78; M-1 to S-77; M-1 to S-76; M-1 to N-75; M-1 to R-74; M-1 to L-73; M-1 to Q-72; M-1 to A-71; M-1 to V-70; M-1 to M-69; M-1 to E-68; M-1 to E-67; M-1 to I-66; M-1 to N-65; M-1 to R-64; M-1 to E-63; M-1 to Y-62; M-1 to E-61; M-1 to E-60; M-1 to M-59; M-1 to R-58; M-1 to A-57; m-1 to Y-56; M-1 to P-55; M-1 to K-54; M-1 to M-53; M-1 to R-52; M-1 to S-51; M-1 to V-50; M-1 to L-49; M-1 to D-48; M-1 to L-47; M-1 to P-46; M-1 to V-45; M-1 to Q-44; M-1 to H-43; M-1 to P-42; M-1 to G-41; M-1 to P-40; M-1 to A-39; M-1 to L-38; M-1 to P-37; M-1 to G-36; M-1 to P-35; M-1 to R-34; M-1 to G-33; M-1 to Q-32; M-1 to G-31; M-1 to K-30; M-1 to R-29; M-1 to K-28; M-1 to S-27; M-1 to K-26; M-1 to P-25; M-1 to S-24; M-1 to R-23; M-1 to P-22; M-1 to Q-21; M-1 to G-20; M-1 to L-19; M-1 to G-18; M-1 to L-17; M-1 to F-16; M-1 to I-15; M-1 to S-14; M-1 to I-13; M-1 to T-12; M-1 to L-11; M-1 to L-10; M-1 to F-9; M-1 to L-8; M-1 to L-7; M-1 to N-6 of the sequence of the IL-20 sequence shown in SEQ ID NO:15. Polynucleotides encoding these polypeptides also are provided.

The invention also provides polypeptides having one or more amino acids deleted from both the amino and the carboxyl termini of an IL-20 polypeptide, which may be described generally as having residues $n^3$-$m^3$ of SEQ ID NO:15, where $n^3$ and $m^3$ are integers as described above.

A specific embodiment of the invention is an IL-20 deletion mutation expression construct for expression in *E. coli*. More specifically, this IL-20 deletion mutation expression construct for expression in *E. coli* will contain a nucleic acid insert which encodes amino acids glutamine-21 through phenlyalanine-180 of the IL-20 polypeptide sequence shown in FIG. 1 (alternatively designated amino acids glutamine-1 through phenlyalanine-160 of the IL-20 polypeptide sequence shown in SEQ ID NO:2).

The following amino acid sequences are additional preferred embodiments of the IL-20 polypeptide of the invention:

MDWPHNLLFLLTISIFLGLGQPRSPK-SKRKGQGRPGPLAPGPHQVPLDLVSRMK-PYARM EEYERNIEEMVAQLRNSSE-LAQRKCEVNLQLWMSNKRSLSPWGYSINHDP SRIPVDLPE HGACVWAV (SEQ ID NO:15) and SRMKPYARMEEYERNEEMVAQLRNSSE-LAQRKCEVNLQLWMSNKRSLSPWGYSINHD PSRIPVDLPEARCLCLGCVNPFTM-QEDRSMVSVPVFSQVPVRRRLCPPPPRT-GPCRQRAV METIAVGCTCIF (SEQ ID NO:27).

Polynucleotides encoding the above polypeptide sequence are also embodiments of the invention.

Other Mutants

In addition to terminal deletion forms of the protein discussed above, it also will be recognized by one of ordinary skill in the art that some amino acid sequences of the IL-20 polypeptide can be varied without significant effect of the structure or function of the protein. If such differences in sequence are contemplated, it should be remembered that there will be critical areas on the protein which determine activity.

Thus, the invention further includes variations of the IL-20 polypeptide which show substantial IL-20 polypeptide activity or which include regions of IL-20 protein such as the protein portions discussed below. Such mutants include deletions, insertions, inversions, repeats, and type substitutions selected according to general rules known in the art so as have little effect on activity. For example, guidance concerning how to make phenotypically silent amino acid substitutions is provided wherein the authors indicate that there are two main approaches for studying the tolerance of an amino acid sequence to change (Bowie, J. U., et al., *Science* 247:1306–1310 (1990)). The first method relies on the process of evolution, in which mutations are either accepted or rejected by natural selection. The second approach uses genetic engineering to introduce amino acid changes at specific positions of a cloned gene and selections or screens to identify sequences that maintain functionality.

As the authors state, these studies have revealed that proteins are surprisingly tolerant of amino acid substitutions. The authors further indicate which amino acid changes are likely to be permissive at a certain position of the protein. For example, most buried amino acid residues require non-polar side chains, whereas few features of surface side chains are generally conserved. Other such phenotypically silent substitutions are described by Bowie and coworkers (stipra) and the references cited therein. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Thus, the fragment, derivative or analog of the polypeptide of SEQ ID NO:2, SEQ ID NO:15, or that encoded by the deposited cDNA (ATCC Deposit No. 209232 and ATCC Deposit No. 209138), may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the above form of the polypeptide, such as an IgG Fc fusion region peptide or leader or secretory sequence or a sequence which is employed for purification of the above form of the polypeptide or a proprotein sequence. Such fragments, derivatives and analogs are deemed to be within the scope of those skilled in the art from the teachings herein.

Thus, the IL-20 of the present invention may include one or more amino acid substitutions, deletions or additions, either from natural mutations or human manipulation. As indicated, changes are preferably of a minor nature, such as conservative amino acid substitutions that do not significantly affect the folding or activity of the protein (see Table II).

TABLE II

| Conservative Amino Acid Substitutions. | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

In specific embodiments, the number of substitutions, deletions or additions in the amino acid sequence of FIG. 1 and/or any of the polypeptide fragments described herein is 30, 29, 28, 27, 26, 25, 24, 23, 22, 21, 20, 19, 18, 17, 16, 15, 14, 13, 12 ,11, 10, 9, 8, 7, 6, 5, 4, 3, 2 or 1 or 30–20, 20–10, 20–15, 15–10, 10–5 or 1–5.

Amino acids in the IL-20 protein of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. The resulting mutant molecules are then tested for biological activity such as receptor binding or in vitro proliferative activity.

Of special interest are substitutions of charged amino acids with other charged or neutral amino acids which may produce proteins with highly desirable improved characteristics, such as less aggregation. Aggregation may not only reduce activity but also be problematic when preparing pharmaceutical formulations, because aggregates can be immunogenic (Pinckard, et al., *Clin. Exp. Immunol.* 2:331–340 (1967); Robbins, et al., *Diabetes* 36:838–845 (1987); Cleland, et al., *Crit. Rev. Therapeutic Drug Carrier Systems* 10:307–377 (1993)).

Replacement of amino acids can also change the selectivity of the binding of a ligand to cell surface receptors (for example, Ostade, et al., *Nature* 361:266–268 (1993)) describes certain mutations resulting in selective binding of TNF-α to only one of the two known types of TNF receptors. Sites that are critical for ligand-receptor binding can also be determined by structural analysis such as crystallization, nuclear magnetic resonance or photoaffinity labeling (Smith, et al., *J. Mol. Biol.* 224:899–904 (1992); de Vos, et al. *Science* 255:306–312 (1992)).

Since IL-20 is a member of the cytokine-related protein family, to modulate rather than completely eliminate biological activities of IL-20 preferably mutations are made in sequences encoding amino acids in the IL-20 conserved domain, i.e., in positions −14 to 158 of SEQ ID NO:2, more preferably in residues 76 to 158 of SEQ ID NO:2, and even more preferably, in residues within this region which are not conserved in all cytokines and cytokine-like molecules. Also forming part of the present invention are isolated polynucleotides comprising nucleic acid sequences which encode the above IL-20 mutants.

The polypeptides of the present invention are preferably provided in an isolated form, and preferably are substantially purified. A recombinantly produced version of the IL-20 polypeptide can be substantially purified by the one-step method described by Smith and Johnson (*Gene* 67:31–40 (1988)). Polypeptides of the invention also can be purified from natural or recombinant sources using anti-IL-20 antibodies of the invention in methods which are well known in the art of protein purification.

The invention further provides an isolated IL-20 polypeptide comprising an amino acid sequence selected from the group consisting of: (a) the amino acid sequence of the full-length IL-20 polypeptide having the complete amino acid sequence shown in SEQ ID NO:2 (i.e., positions −20 to 160 of SEQ ID NO:2); (b) the amino acid sequence of the full-length IL-20 polypeptide having the complete amino acid sequence shown in SEQ ID NO:15 (i.e., positions 1 to 118 of SEQ ID NO:2); (c) the amino acid sequence of the full-length IL-20 polypeptide having the complete amino acid sequence shown in SEQ ID NO:2 excepting the N-terminal methionine (i.e., positions −19 to 160 of SEQ ID NO:2); (d) the amino acid sequence of the full-length IL-20 polypeptide having the complete amino acid sequence shown in SEQ ID NO:15 excepting the N-terminal methionine (i.e., positions 2 to 118 of SEQ ID NO:15); (e) the amino acid sequence of the predicted mature IL-20 polypeptide having the amino acid sequence at positions 1 to 160 in SEQ ID NO:2; (f) the amino acid sequence of the predicted mature IL-20 polypeptide having the amino acid sequence at positions 21 to 118 in SEQ ID NO:15; (f) the complete amino acid sequence encoded by the cDNA clone contained in the ATCC Deposit No. 209232; (g) the complete amino acid sequence encoded by the cDNA clone contained in the ATCC Deposit No. 209138; (h) the complete amino acid sequence excepting the N-terminal methionine encoded by the cDNA clone contained in the ATCC Deposit No. 209232; (i) the complete amino acid sequence excepting the N-terminal methionine encoded by the cDNA clone contained in the ATCC Deposit No. 209138; (j) the complete amino acid sequence of the predicted mature IL-20 polypeptide encoded by the cDNA clone contained in the ATCC Deposit No. 209232; and, (k) the complete amino acid sequence of the predicted mature IL-20 polypeptide encoded by the cDNA clone contained in the ATCC Deposit No. 209138. The polypeptides of the present invention also include polypeptides having an amino acid sequence at least 80% identical to (that is to say, at most 20% different from), more preferably at least 90% identical to (that is to say, at most 10% different from), and still more preferably 95%, 96%, 97%, 98% or 99% identical to (that is to say, at most 5%, 4%, 3%, 2% or 1% different from) those described in (a), (b), (c), (d), (e), (f), (g), (h), (i), (j) or (k), above, as well as polypeptides having an amino acid sequence with at least 90% similarity, and more preferably at least 95% similarity, to those above.

An additional embodiment of this aspect of the invention relates to a peptide or polypeptide which comprises the amino acid sequence of an epitope-bearing portion of an IL-20 polypeptide having an amino acid sequence described in (a), (b), (c), (d), (e), (f), (g), (h), (i), (j) or (k), above, as well as polypeptides having an amino acid sequence with at least 90% similarity, and more preferably at least 95% similarity, to those above.

Further polypeptides of the present invention include polypeptides which have at least 90% similarity, more preferably at least 95% similarity, and still more preferably at least 96%, 97%, 98% or 99% similarity to those described above. The polypeptides of the invention also comprise those which are at least 80% identical, more preferably at least 90% or 95% identical, still more preferably at least 96%, 97%, 98% or 99% identical to the polypeptide encoded by the deposited cDNA (ATCC Deposit No. 209232 and ATCC Deposit No. 209138) or to the polypeptide of SEQ ID NO:2, or to the polypeptide of SEQ ID NO:15, and also include portions of such polypeptides with at least 30 amino acids and more preferably at least 50 amino acids.

A further embodiment of the invention relates to a peptide or polypeptide which comprises the amino acid sequence of an IL-20 polypeptide having an amino acid sequence which contains at least one conservative amino acid substitution, but not more than 50 conservative amino acid substitutions, even more preferably, not more than 40 conservative amino acid substitutions, still more preferably not more than 30 conservative amino acid substitutions, and still even more preferably not more than 20 conservative amino acid substitutions. Of course, in order of ever-increasing preference, it is highly preferable for a peptide or polypeptide to have an amino acid sequence which comprises the amino acid sequence of an IL-20 polypeptide, which contains at least one, but not more than 10, 9, 8, 7, 6, 5, 4, 3, 2 or 1 conservative amino acid substitutions.

By "% similarity" for two polypeptides is intended a similarity score produced by comparing the amino acid sequences of the two polypeptides using the Bestfit program (Wisconsin Sequence Analysis Package, Version 8 for Unix, Genetics Computer Group, University Research Park, 575 Science Drive, Madison, Wis. 53711) and the default settings for determining similarity. Bestfit uses the local homology algorithm of Smith and Waterman (Advances in Applied Mathematics 2:482–489, 1981) to find the best segment of similarity between two sequences.

By a polypeptide having an amino acid sequence at least, for example, 95% "identical" to a reference amino acid sequence of an IL-20 polypeptide is intended that the amino acid sequence of the polypeptide is identical to the query sequence except that the polypeptide sequence may include up to five amino acid alterations per each 100 amino acids of the reference amino acid of the IL-20 polypeptide. In other words, to obtain a polypeptide having an amino acid sequence at least 95% identical to a query amino acid sequence, up to 5% of the amino acid residues in the query sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in SEQ ID NO:2 or to the amino acid sequence encoded by deposited cDNA clone can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed. A preferred method for determing the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237–245). In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are to made for the purposes of the present invention.

The polypeptide of the present invention could be used as a molecular weight marker on SDS-PAGE gels or on molecular sieve gel filtration columns using methods well known to those of skill in the art.

As described in detail below, the polypeptides of the present invention can also be used to raise polyclonal and monoclonal antibodies, which are useful in assays for detecting IL-20 protein expression as described below or as agonists and antagonists capable of enhancing or inhibiting IL-20 protein function. Further, such polypeptides can be used in the yeast two-hybrid system to "capture" IL-20 protein binding proteins which are also candidate agonists and antagonists according to the present invention. The yeast two hybrid system is described by Fields and Song (*Nature* 340:245–246 (1989)).

Epitope-Bearing Portions

In another aspect, the invention provides a peptide or polypeptide comprising an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. On the other hand, a region of a protein molecule to which an antibody can bind is defined as an "antigenic epitope." The number of immunogenic epitopes of a protein generally is less than the number of antigenic epitopes (see, for instance, Geysen, et al., *Proc. Natl. Acad. Sci. USA* 81:3998–4002 (1983)).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein (see, for instance, Sutcliffe, J. G., et al., *Science* 219:660–666 (1983)). Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Antigenic epitope-bearing peptides and polypeptides of the invention are therefore useful to raise antibodies, including monoclonal antibodies, that bind specifically to a polypeptide of the invention (see, for instance, Wilson, et al., *Cell* 37:767–778 (1984)).

Antigenic epitope-bearing peptides and polypeptides of the invention preferably contain a sequence of at least seven, more preferably at least nine and most preferably between about 15 to about 30 amino acids contained within the amino acid sequence of a polypeptide of the invention. Non-limiting examples of antigenic polypeptides or peptides that can be used to generate IL-20-specific antibodies include: a polypeptide comprising amino acid residues from about Gln-21 to about Arg-29 in FIG. 1 (SEQ ID NO:2), a polypeptide comprising amino acid residues from about Gln-21 to about Gly-41 in FIG. 1 (SEQ ID NO:2), a polypeptide comprising amino acid residues from about Ser-24 to about Gln-32 in FIG. 1 (SEQ ID NO:2), a polypeptide comprising amino acid residues from about Arg-29 to about Pro-37 in FIG. 1 (SEQ ID NO:2), a polypeptide comprising amino acid residues from about Arg-52 to about Glu-60 in FIG. 1 (SEQ ID NO:2), a polypeptide comprising amino acid residues from about Arg-52 to about Met-69 in FIG. 1 (SEQ ID NO:2), a polypeptide comprising amino acid residues from about Glu-61 to about Met-69 in FIG. 1 (SEQ ID NO:2), a polypeptide comprising amino acid residues from about Asn-75 to about Val-86 in FIG. 1 (SEQ ID NO:2), a polypeptide comprising amino acid residues from about Ser-93 to about Trp-101 in FIG. 1 (SEQ ID NO:2), a polypeptide comprising amino acid residues from about Ile-105 to about Pro-113 in FIG. 1 (SEQ ID NO:2), a polypeptide comprising amino acid residues from about Met-132 to about Ser-140 in FIG. 1 (SEQ ID NO:2), a polypeptide comprising amino acid residues from about Arg-150 to about Pro-158 in FIG. 1 (SEQ ID NO:2), a polypeptide comprising amino acid residues from about Pro-156 to about Arg-164 in FIG. 1 (SEQ ID NO:2), a polypeptide comprising amino acid residues from about Gly-161 to about Met-169 in FIG. 1 (SEQ ID NO:2), and a polypeptide comprising amino acid residues from about Val-149 to about Ala-167 in FIG. 1 (SEQ ID NO:2). These polypeptide fragments have been determined to bear antigenic epitopes of the IL-20 protein by the analysis of the Jameson-Wolf antigenic index, as shown in FIG. 3, above.

The epitope-bearing peptides and polypeptides of the invention may be produced by any conventional means (see, for example, Houghten, R. A., et al., *Proc. Natl. Acad. Sci. USA* 82:5131–5135 (1985); and U.S. Pat. No. 4,631,211 to Houghten, et al. (1986)).

Epitope-bearing peptides and polypeptides of the invention are used to induce antibodies according to methods well known in the art (see, for instance, Sutcliffe, et al., supra; Wilson, et al., supra; Chow, M., et al., *Proc. Natl. Acad. Sci. USA* 82:910–914; and Bittle, F. J., et al., *J. Gen. Virol.* 66:2347–2354 (1985)). Immunogenic epitope-bearing peptides of the invention, i.e., those parts of a protein that elicit an antibody response when the whole protein is the immunogen, are identified according to methods known in the art (see, for instance, Geysen, et al., supra). Further still, U.S. Pat. No. 5,194,392, issued to Geysen, describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092, issued to Geysen, describes a method of detecting or determining a sequence of monomers which is a topographical equivalent of a ligand which is complementary to the ligand binding site of a particular receptor of interest. Similarly, U.S. Pat. No. 5,480,971, issued to Houghten and colleagues, on Peralkylated Oligopeptide Mixtures discloses linear C1–C7-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

Fusion Proteins

As one of skill in the art will appreciate, IL-20 polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EP A 394,827; Traunecker, et al., *Nature* 331:84–86 (1988)). Fusion proteins that have a disulfide-linked dimeric structure due to the IgG part can also be more efficient in binding and neutralizing other molecules than the monomeric IL-20 protein or protein fragment alone (Fountoulakis, et al., *J. Biochem.* 270:3958–3964 (1995)).

Antibodies

IL-20 protein-specific antibodies for use in the present invention can be raised against the intact IL-20 protein or an antigenic polypeptide fragment thereof, which may be presented together with a carrier protein, such as an albumin, to an animal system (such as rabbit or mouse) or, if it is long enough (at least about 25 amino acids), without a carrier.

As used herein, the term "antibody" (Ab) or "monoclonal antibody" (Mab) is meant to include intact molecules as well as antibody fragments (such as, for example, Fab and F(ab')2 fragments) which are capable of specifically binding to IL-20 protein. Fab and F(ab')2 fragments lack the Fc fragment of intact antibody, clear more rapidly from the circulation, and may have less non-specific tissue binding of an intact antibody (Wahl, et al., *J. Nucl. Med.* 24:316–325 (1983)). Thus, these fragments are preferred.

The antibodies of the present invention may be prepared by any of a variety of methods. For example, cells expressing the IL-20 protein or an antigenic fragment thereof can be administered to an animal in order to induce the production of sera containing polyclonal antibodies. In a preferred method, a preparation of IL-20 protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or IL-20 protein binding fragments thereof). Such monoclonal antibodies can be prepared using hybridoma technology (Kohler, et al., *Nature* 256:495 (1975); Kohler, et al., *Eur. J. Immunol.* 6:511 (1976); Kohler, et al., *Eur. J. Immunol.* 6:292 (1976); Hammerling, et al., in: *Monoclonal Antibodies and T-Cell Hybridlomas*, Elsevier, N.Y., (1981) pp. 563–681)). In general, such procedures involve immunizing an animal (preferably a mouse) with an IL-20 protein antigen or, more preferably, with an IL-20 protein-expressing cell. Suitable cells can be recognized by their capacity to bind anti-IL-20 protein antibody. Such cells may be cultured in any suitable tissue culture medium; however, it is preferable to culture cells in Earle's modified Eagle's medium supplemented with 10% fetal bovine serum (inactivated at about 56° C.), and supplemented with about 10 $\mu$g/l of nonessential amino acids, about 1,000 U/ml of penicillin, and about 100 $\mu$g/ml of streptomycin. The splenocytes of such mice are extracted and fused with a suitable myeloma cell line. Any suitable myeloma cell line may be employed in accordance with the present invention; however, it is preferable to employ the parent myeloma cell line (SP2O), available from the American Type Culture Collection, Manassas, Va. After fusion, the resulting hybridoma cells are selectively maintained in HAT medium, and then cloned by limiting dilution as described by Wands and colleagues (*Gastroenterology* 80:225–232 (1981)). The hybridoma cells obtained through such a selection are then assayed to identify clones which secrete antibodies capable of binding the IL-20 protein antigen.

Alternatively, additional antibodies capable of binding to the IL-20 protein antigen may be produced in a two-step procedure through the use of anti-idiotypic antibodies. Such a method makes use of the fact that antibodies are themselves antigens, and that, therefore, it is possible to obtain an antibody which binds to a second antibody. In accordance with this method, IL-20 protein-specific antibodies are used to immunize an animal, preferably a mouse. The splenocytes of such an animal are then used to produce hybridoma cells, and the hybridoma cells are screened to identify clones which produce an antibody whose ability to bind to the IL-20 protein-specific antibody can be blocked by the IL-20 protein antigen. Such antibodies comprise anti-idiotypic antibodies to the IL-20 protein-specific antibody and can be used to immunize an animal to induce formation of further IL-20 protein-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, IL-20 protein-binding fragments can be produced through the application of recombinant DNA technology or through synthetic chemistry.

For in vivo use of anti-IL-20 in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art (Morrison, *Science* 229:1202 (1985); Oi, et al., *BioTechniques* 4:214 (1986); Cabilly, et al., U.S. Pat. No. 4,816,567; Taniguchi, et al., EP 171496; Morrison, et al., EP 173494; Neuberger, et al., WO 8601533; Robinson, et al., WO 8702671; Boulianne, et al., *Nature* 312:643 (1984); Neuberger, et al., *Nature* 314:268 (1985).

Immune System-related Disorders

Diagnosis

The present inventors have discovered that IL-20 is expressed in the thymus. For a number of immune system-related disorders, substantially altered (increased or decreased) levels of IL-20 gene expression can be detected in immune system tissue or other cells or bodily fluids (e.g., sera, plasma, urine, synovial fluid or spinal fluid) taken from an individual having such a disorder, relative to a "standard" IL-20 gene expression level, that is, the IL-20 expression level in immune system tissues or bodily fluids from an individual not having the immune system disorder. Thus, the invention provides a diagnostic method useful during diagnosis of a immune system disorder, which involves measuring the expression level of the gene encoding the IL-20 protein in immune system tissue or other cells or body fluid from an individual and comparing the measured gene expression level with a standard IL-20 gene expression level, whereby an increase or decrease in the gene expression level compared to the standard is indicative of an immune system disorder.

In particular, it is believed that certain tissues in mammals with cancer of the immune system express significantly enhanced levels of the IL-20 protein and mRNA encoding the IL-20 protein when compared to a corresponding "standard" level. Further, it is believed that enhanced levels of the IL-20 protein can be detected in certain body fluids (e.g., sera, plasma, urine, and spinal fluid) from mammals with such a cancer when compared to sera from mammals of the same species not having the cancer.

Thus, the invention provides a diagnostic method useful during diagnosis of a immune system disorder, including cancers of this system, which involves measuring the expression level of the gene encoding the IL-20 protein in immune system tissue or other cells or body fluid from an individual and comparing the measured gene expression level with a standard IL-20 gene expression level, whereby an increase or decrease in the gene expression level compared to the standard is indicative of an immune system disorder.

Where a diagnosis of a disorder in the immune system, including diagnosis of a tumor, has already been made according to conventional methods, the present invention is useful as a prognostic indicator, whereby patients exhibiting enhanced IL-20 gene expression will experience a worse clinical outcome relative to patients expressing the gene at a level nearer the standard level.

By "assaying the expression level of the gene encoding the IL-20 protein" is intended qualitatively or quantitatively measuring or estimating the level of the IL-20 protein or the level of the mRNA encoding the IL-20 protein in a first biological sample either directly (e.g., by determining or estimating absolute protein level or mRNA level) or relatively (e.g., by comparing to the IL-20 protein level or mRNA level in a second biological sample). Preferably, the IL-20 protein level or mRNA level in the first biological sample is measured or estimated and compared to a standard IL-20 protein level or mRNA level, the standard being taken from a second biological sample obtained from an individual not having the disorder or being determined by averaging levels from a population of individuals not having a disorder of the immune system. As will be appreciated in the art, once a standard IL-20 protein level or mRNA level is known, it can be used repeatedly as a standard for comparison.

By "biological sample" is intended any biological sample obtained from an individual, body fluid, cell line, tissue culture, or other source which contains IL-20 protein or mRNA. As indicated, biological samples include body fluids (such as sera, plasma, urine, synovial fluid and spinal fluid) which contain free mature IL-20 protein, immune system tissue, and other tissue sources found to express complete or mature IL-20 or an IL-20 receptor. Methods for obtaining tissue biopsies and body fluids from mammals are well known in the art. Where the biological sample is to include mRNA, a tissue biopsy is the preferred source.

The present invention is useful for diagnosis or treatment of various immune system-related disorders in mammals, preferably humans. Such disorders include tumors, cancers, interstitial lung disease (such as Langerhans cell granulomatosis), and any disregulation of immune cell function including, but not limited to, autoimmunity, arthritis, leukemias, lymphomas, immunosuppression, immunity, humoral immunity, inflammatory bowel disease, myelo suppression, and the like.

Total cellular RNA can be isolated from a biological sample using any suitable technique such as the single-step guanidinium-thiocyanate-phenol-chloroform method described by Chomczynski and Sacchi (*Anal. Biochem.*

162:156–159 (1987)). Levels of mRNA encoding the IL-20 protein are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

Assaying IL-20 protein levels in a biological sample can occur using antibody-based techniques. For example, IL-20 protein expression in tissues can be studied with classical immunohistological methods (Jalkanen, M., et al., *J. Cell. Biol.* 101:976–985 (1985); Jalkanen, M., et al., *J. Cell. Biol.* 105:3087–3096 (1987)). Other antibody-based methods useful for detecting IL-20 protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine ($^{125}I$, $^{121}I$), carbon ($^{14}C$), sulfur ($^{35}S$), tritium ($^{3}H$), indium ($^{112}In$), and technetium ($^{99m}Tc$), and fluorescent labels, such as fluorescein and rhodamine, and biotin.

In addition to assaying IL-20 protein levels in a biological sample obtained from an individual, IL-20 protein can also be detected in vivo by imaging. Antibody labels or markers for in vivo imaging of IL-20 protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

An IL-20 protein-specific antibody or antibody fragment which has been labeled with an appropriate detectable imaging moiety, such as a radioisotope (for example, $^{131}I$, $^{112}In$, $^{99m}Tc$), a radio-opaque substance, or a material detectable by nuclear magnetic resonance, is introduced (for example, parenterally, subcutaneously or intraperitoneally) into the mammal to be examined for immune system disorder. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}Tc$. The labeled antibody or antibody fragment will then preferentially accumulate at the location of cells which contain IL-20 protein. In vivo tumor imaging is described by Burchiel and coworkers (Chapter 13 in *Tumor Imaging: The Radiochemical Detection of Cancer*, Burchiel, S. W. and Rhodes, B. A., eds., Masson Publishing Inc. (1982)).

Treatment

As noted above, IL-20 polynucleotides and polypeptides are useful for diagnosis of conditions involving abnormally high or low expression of IL-20 activities. Given the cells and tissues where IL-20 is expressed as well as the activities modulated by IL-20, it is readily apparent that a substantially altered (increased or decreased) level of expression of IL-20 in an individual compared to the standard or "normal" level produces pathological conditions related to the bodily system(s) in which IL-20 is expressed and/or is active.

Based on its ability to alter expression of the cellular transcription factor NF-κB and induce IL-6 expression, IL-20 may be used to treat B-cell neoplasms, including chronic lymphocytic leukemia (CLL) and B-lymphocytic leukemia (BLL). Further, an IL-20-mediated induction of IL-6 expression can also be used to activate mature lymphoid cells, which have cytolytic activities. As a result, IL-20 can be used as an anticancer and antiviral treatment. Various immunodeficiencies, for example, in T- and B-lymphocytes, or immune disorders, for example, rheumatoid arthritis, may also be beneficially effected by treatment with IL-20. Immunodeficiencies such as leukopenia, a reduction in the number of circulating leukocytes in the peripheral blood, may be the result of viral infections, for example, HIV, severe exposure to radiation, side effects of cancer therapy or the result of other medical treatment. Therapeutic treatment of leukopenia with IL-20 compositionsmay avoid undesirable side effects caused by treatment with presently available drugs. Other conditions susceptible for IL-20 include patients recovering from bone marrow transplants. IL-20 may also be used to augment the humoral or cellular immune response in vivo in coadministration with other therapeutic agents. For example, IL-20 may be used to enhance the efficacy of viral antigen vaccines, such as HIV or tumor antigen vaccines.

Primarily through its effects on expression of the cellular transcription factor NF-κB and IL-6 expression, IL-20 also functions as a hybridomal growth factor in culture medium for hybridoma cell lines to increase the yield thereof.

IL-20 may also be useful in immunotherapeutic and anti-inflammation compositions. IL-20 may also be used for the treatment of patients suffering from chemotherapy from bone marrow transplants. IL-20 may be further used to treat corneal damage, keratitis, and ulcers.

Among the other treatments IL-20 may be used for include conditions such as thrombocytopenia, in which IL-20 will enhance differentiation into platelet producing cells. IL-20 may also be used to restore neutrophil and platelet counts in treatment of cancer and in bone marrow transplantation.

IL-20 may also be used to induce liver cells to produce a number of proteins called "acute phase proteins". The acute phase proteins are usually induced after an acute insult, such as traumatic or bacterial shock. Accordingly, administration of IL-20 may be beneficial in promoting recovery.

IL-20 may also be used in cell transplant therapy including autogenous bone marrow graft therapy.

IL-20 may also be employed to enhance erythropoietin production for treating anemias associated with inflammation, renal failure, AIDS, and cancer.

IL-20 may be used, alone or incombination with other therapeutic products, in the treatment of diseases characterized by a decreased level of either myeloid or lymphoid cells of the hematopoietic system. This protein may also be capable of stimulating accessory and mature cells, for example, monocytes to produce other hematopoietic-like factors which, in turn stimulate the formation of colonies of other hematopoietic cells, as well as other hematopoietic-like activities.

It is well-known in the art that, in addition to a specific cellular function, cellular receptor molecules may also often be exploited by a virus as a means of initiating entry into a potential host cell. For example, it was recently discovered by Wu and colleagues (*J. Exp. Med.* 185:1681–1691 (1997)) that the cellular chemokine receptor CCR5 functions not only as a cellular chemokine receptor, but also as a receptor for macrophage-tropic human immunodeficiency virus (HIV)-1. In addition, RANTES, MIP-1α, and MIP-1β, which are agonists for the cellular chemokine receptor CCR5, inhibit entry of various strains of HIV-1 into susceptible cell lines (Cocchi, F., et al., *Science* 270:1811–1815 (1995)). Thus, the invention also provides a method of treating an individual exposed to, or infected with, a virus through the prophylactic or therapeutic administration of IL-20, or an agonist or antagonist thereof, to block or disrupt the interaction of a viral particle with the IL-20 receptor and, as a result, block the initiation or continuation of viral infectivity.

The IL-20 of the present invention binds to the IL-20 receptor and, as such, is likely to block immuno-tropic viral infections. Further, expression patterns of cytokines and cytokine receptors suggest that the IL-20 receptor is expressed primarily in hematopoietic and neural tissues. These observations further suggest that agonists and antagonists, including ligands, of IL-20 may be useful as a method of blocking or otherwise regulating the infectivity of immunotropic and neurotropic viral infections. A non-limiting list of viruses which infect humans and can infect cells of the hematopoietic and nervous systems includes such retroviruses as HIV-1, HIV-2, human T-cell lymphotropic virus (HTLV)-I, and HTLV-II, as well as other DNA and RNA viruses such as herpes simplex virus (HSV)-1, HSV-2, HSV-6, cytomegalovirus (CMV), Epstein-Barr virus (EBV), herpes samirii, adenoviruses, rhinoviruses, influenza viruses, reoviruses, and the like.

The ability of the IL-20 of the present invention, or agonists or antagonists thereof, to prophylactically or therapeutically block viral infection may be easily tested by the skilled artisan. For example, Simmons and coworkers (Science 276:276–279 (1997)) and Arenzana-Seisdedos and colleagues (*Nature* 383:400 (1996)) each outline a method of observing suppression of HIV-1 infection by an antagonist of the CCR5 chemokine receptor and of the CC chemokine RANTES, respectively, in cultured peripheral blood mononuclear cells. Cells are cultured and infected with a virus, HIV-1 in both cases noted above. An agonist or antagonist of the CC chemokine or its receptor is then immediately added to the culture medium. Evidence of the ability of the agonist or antagonist of the chemokine or cellular receptor is determined by evaluating the relative success of viral infection at 3, 6, and 9 days postinfection.

Administration of a pharmaceutical composition comprising an amount of an isolated IL-20, or an agonist or antagonist thereof, of the invention to an individual either infected with a virus or at risk for infection with a virus is performed as described below.

It will also be appreciated by one of ordinary skill that, since the IL-20 protein of the invention is a member of the cytokine family of polypeptides, the mature secreted form of the protein may be released in soluble form from the cells which express the IL-20 by proteolytic cleavage. Therefore, when IL-20 mature form is added from an exogenous source to cells, tissues or the body of an individual, the protein will exert its physiological activities on its target cells of that individual.

Therefore, it will be appreciated that conditions caused by a decrease in the standard or normal level of IL-20 activity in an individual, particularly disorders of the immune system, can be treated by administration of IL-20 polypeptide (in the form of the mature protein). Thus, the invention also provides a method of treatment of an individual in need of an increased level of IL-20 activity comprising administering to such an individual a pharmaceutical composition comprising an amount of an isolated IL-20 polypeptide of the invention, particularly a mature form of the IL-20 protein of the invention, effective to increase the IL-20 activity level in such an individual.

Since IL-20 is a novel homologue of the recently described cytokine IL-17, it will have a wide range of cytokine-like activities. IL-20 may be employed to enhance host defenses against resistant chronic and acute infections, for example, mycobacterial infections via the attraction and activation of microbicidal leukocytes. IL-20 may also be employed to increase T-cell proliferation by the stimulation of IL-2 biosynthesis for the treatment of T-cell mediated auto-immune diseases and lymphocytic leukemias. IL-20 may also be employed to regulate hematopoiesis, by regulating the activation and differentiation of various hematopoietic progenitor cells, for example, to release mature leukocytes from the bone marrow following chemotherapy, i.e., in stem cell mobilization. IL-20 may also be employed to treat sepsis. Also, stimulation of the cell by IL-20 strongly induces IL-6 expression. IL-6 is a potent growth factor for myelomas, plasmacytomas, and hybridomas and is involved in the growth of Lennert's Lymphoma T-cells. As a result, IL-20 and IL-20 agonists may be used in the treatment of such cancers, analogous disease states, and others known to those of skill in the art.

Schwann cells, and microglia and astrocytes are the immunocompetent cells of the peripheral and central nervous systems, respectively, that secrete a variety of immune and inflammatory mediators. Inflammatory processes involving reactive microglia, e.g. those associated with the lesions found following stroke or in multiple sclerosis, and with beta-amyloid containing plaques in Alzheimer's Disease, have been proposed to contribute to the neuronal pathology characteristic of these clinical conditions. In the peripheral nervous system, there is increasing evidence that Schwann cells play an essential role in the pathogenesis associated with autoimmune inflammatory peripheral nerve disease as well as other demylinating diseases such as Guillain-Barr syndrome. Furthermore, all three cell types are targets for numerous interleukins, including IL-20.

Formulations

The IL-20 polypeptide composition will be formulated and dosed in a fashion consistent with good medical practice, taking into account the clinical condition of the individual patient (especially the side effects of treatment with IL-20 polypeptide alone), the site of delivery of the IL-20 polypeptide composition, the method of administration, the scheduling of administration, and other factors known to practitioners. The "effective amount" of IL-20 polypeptide for purposes herein is thus determined by such considerations.

As a general proposition, the total pharmaceutically effective amount of IL-20 polypeptide administered parenterally per dose will be in the range of about 1 $\mu$g/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the IL-20 polypeptide is typically administered at a dose rate of about 1 $\mu$g/kg/hour to about 50 $\mu$g/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing the IL-20 of the invention may be administered orally, rectally, parenterally, intracistemally, intravaginally, intraperitoneally, topically (as by powders, ointments, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrastemal, subcutaneous and intraarticular injection and infusion.

The IL-20 polypeptide is also suitably administered by sustained-release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (Sidman, U., et al., *Biopolymers* 22:547–556 (1983)), poly(2-hydroxyethyl methacrylate; Langer, R., et al., *J. Biomed. Mater. Res.* 15:167–277 (1981), and Langer, R., *Chem. Tech.* 12:98–105 (1982)), ethylene vinyl acetate (Langer, R., et al., *Id.*) or poly-D-(−)-3-hydroxybutyric acid (EP 133,988). Sustained-release IL-20 polypeptide compositions also include liposomally entrapped IL-20 polypeptide. Liposomes containing IL-20 polypeptide are prepared by methods known in the art (DE 3,218,12 1; Epstein, et al., *Proc. Natl. Acad. Sci.* (*USA*) 82:3688–3692 (1985); Hwang, et al., *Proc. Natl. Acad. Sci.* (*USA*) 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324). Ordinarily, the liposomes are of the small (about 200–800 Angstroms) unilamellar type in which the lipid content is greater than about 30 mol. percent cholesterol, the selected proportion being adjusted for the optimal IL-20 polypeptide therapy.

For parenteral administration, in one embodiment, the IL-20 polypeptide is formulated generally by mixing it at the desired of purity, in a unit dosage injectable form (solution, suspension, or emulsion), with a pharmaceutically acceptable carrier, i.e. one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the IL-20 polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The IL-20 polypeptide is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of IL-20 polypeptide salts.

IL-20 polypeptide to be used for therapeutic administration must be sterile. Sterility is readily accomplished by filtration through sterile filtration membranes (e.g., 0.2 micron membranes). Therapeutic IL-20 polypeptide compositions generally are placed into a container having a sterile access port, for example, an intravenous solution bag or vial having a stopper pierceable by a hypodermic injection needle.

IL-20 polypeptide ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous IL-20 polypeptide solution, and the resulting mixture is lyophilized. The infusion solution is prepared by reconstituting the lyophilized IL-20 polypeptide using bacteriostatic water-for-injection (WFI).

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

Agonists and Antagonists—Assays and Molecules

The invention also provides a method of screening compounds to identify those which enhance or block the action of IL-20 on cells, such as its interaction with IL-20-binding molecules such as receptor molecules. An agonist is a compound which increases the natural biological functions of IL-20 or which functions in a manner similar to IL-20, while antagonists decrease or eliminate such functions.

In another aspect of this embodiment the invention provides a method for identifying a receptor protein or other ligand-binding protein which binds specifically to an IL-20 polypeptide. For example, a cellular compartment, such as a membrane or a preparation thereof, may be prepared from a cell that expresses a molecule that binds IL-20. The preparation is incubated with labeled IL-20 and complexes of IL-20 bound to the receptor or other binding protein are isolated and characterized according to routine methods known in the art. Alternatively, the IL-20 polypeptide may be bound to a solid support so that binding molecules solubilized from cells are bound to the column and then eluted and characterized according to routine methods.

In the assay of the invention for agonists or antagonists, a cellular compartment, such as a membrane or a preparation thereof, may be prepared from a cell that expresses a molecule that binds IL-20, such as a molecule of a signaling or regulatory pathway modulated by IL-20. The preparation is incubated with labeled IL-20 in the absence or the presence of a candidate molecule which may be an IL-20 agonist or antagonist. The ability of the candidate molecule to bind the binding molecule is reflected in decreased binding of the labeled ligand. Molecules which bind gratuitously, i.e., without inducing the effects of IL-20 on binding the IL-20 binding molecule, are most likely to be good antagonists. Molecules that bind well and elicit effects that are the same as or closely related to IL-20 are agonists.

IL-20-like effects of potential agonists and antagonists may by measured, for instance, by determining activity of a second messenger system following interaction of the candidate molecule with a cell or appropriate cell preparation, and comparing the effect with that of IL-20 or molecules that elicit the same effects as IL-20. Second messenger systems that may be useful in this regard include but are not limited to AMP guanylate cyclase, ion channel or phosphoinositide hydrolysis second messenger systems.

Another example of an assay for IL-20 antagonists is a competitive assay that combines IL-20 and a potential antagonist with membrane-bound IL-20 receptor molecules or recombinant IL-20 receptor molecules under appropriate conditions for a competitive inhibition assay. IL-20 can be labeled, such as by radioactivity, such that the number of IL-20 molecules bound to a receptor molecule can be determined accurately to assess the effectiveness of the potential antagonist.

Potential antagonists include small organic molecules, peptides, polypeptides and antibodies that bind to a polypeptide of the invention and thereby inhibit or extinguish its activity. Potential antagonists also may be small organic molecules, a peptide, a polypeptide such as a closely related protein or antibody that binds the same sites on a binding molecule, such as a receptor molecule, without inducing IL-20-induced activities, thereby preventing the action of IL-20 by excluding IL-20 from binding.

Other potential antagonists include antisense molecules. Antisense technology can be used to control gene expression through antisense DNA or RNA or through triple-helix formation. Antisense techniques are discussed in a number of studies (for example, Okano, *J. Neurochem.* 56:560 (1991); "Oligodeoxynucleotides as Antisense Inhibitors of Gene Expression." CRC Press, Boca Raton, Fla. (1988)). Triple helix formation is discussed in a number of studies, as well (for instance, Lee, et al., *Nucleic Acids Research* 6:3073 (1979); Cooney, et al., *Science* 241:456 (1988); Dervan, et al., *Science* 251:1360 (1991)). The methods are based on binding of a polynucleotide to a complementary DNA or RNA. For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of IL-20. The antisense RNA oligonucleotide hybridizes to the mRNA in vivo and blocks translation of the mRNA molecule into IL-20 polypeptide. The oligonucleotides described above can also be delivered to cells such that the antisense RNA or DNA may be expressed in vivo to inhibit production of IL-20 protein.

The agonists and antagonists may be employed in a composition with a pharmaceutically acceptable carrier, e.g., as described above.

The antagonists may be employed for instance to inhibit the activation of macrophages and their precursors, and of neutrophils, basophils, B lymphocytes and some T-cell subsets, e.g., activated and CD8 cytotoxic T cells and natural killer cells, in certain auto-immune and chronic inflammatory and infective diseases. Examples of auto-immune diseases include multiple sclerosis, and insulin-dependent diabetes. The antagonists may also be employed to treat infectious diseases including silicosis, sarcoidosis, idiopathic pulmonary fibrosis by preventing the activation of mononuclear phagocytes. They may also be employed to treat idiopathic hypereosinophilic syndrome by preventing eosinophil production. Antagonists may also be employed to treat rheumatoid arthritis by preventing the activation of monocytes in the synovial fluid in the joints of patients. Monocyte activation plays a significant role in the pathogenesis of both degenerative and inflammatory arthropathies. The antagonists may be employed to interfere with the deleterious cascades attributed primarily to IL-1 and TNF, which prevents the biosynthesis of other inflammatory cytokines. In this way, the antagonists may be employed to prevent inflammation. Antibodies against IL-20 may be employed to bind to and inhibit IL-20 activity to treat such conditions described above. Any of the above antagonists may be employed in a composition with a pharmaceutically acceptable carrier, e.g., as hereinafter described.

Gene Mapping

The nucleic acid molecules of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

In certain preferred embodiments in this regard, the cDNA herein disclosed is used to clone genomic DNA of an IL-20 protein gene. This can be accomplished using a variety of well known techniques and libraries, which generally are available commercially. The genomic DNA then is used for in situ chromosome mapping using well known techniques for this purpose.

In addition, in some cases, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Fluorescence in situ hybridization ("FISH") of a cDNA clone to a metaphase chromosomal spread can be used to provide a precise chromosomal location in one step. This technique can be used with probes from the cDNA as short as 50 or 60 bp (for a review of this technique, see Verma, et al., *Human Chromosomes: A Manual Of Basic Techniques*, Pergamon Press, New York (1988)).

Once a sequence has been mapped to a precise chromosomal location, the physical position of the sequence on the chromosome can be correlated with genetic map data. Such data are found, for example, on the World Wide Web (McKusick, V. *Mendelian Inheritance In Man*, available on-line through Johns Hopkins University, Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

Having generally described the invention, the same will be more readily understood by reference to the following examples, which are provided by way of illustration and are not intended as limiting.

EXAMPLES

Example 1

Isolation of the IL-20 cDNA Clone From the Deposited Sample

The cDNA for IL-20 is inserted into the Eco RI and Xho I restriction sites in the multiple cloning site of pBluescript.

(Stratagene.) pBluescript contains an ampicillin resistance gene and may be transformed into *E. coli* strain DH10B, available from Life Technologies. (See, for instance, Gruber, C. E., et al., *Focus* 15:59-(1993).)

Two approaches can be used to isolate IL-20 from the deposited sample. First, the deposited clone is transformed into a suitable host (such as XL-1 Blue (Stratagene)) using techniques known to those of skill in the art, such as those provided by the vector supplier or in related publications or patents. The transformants are plated on 1.5% agar plates (containing the appropriate selection agent, e.g., ampicillin) to a density of about 150 transformants (colonies) per plate. A single colony is then used to generate DNA using nucleic acid isolation techniques well known to those skilled in the art. (e.g., Sambrook et al., Molecular Cloning: A Laboratory Manual, 2nd Edit., (1989), Cold Spring Harbor Laboratory Press.)

Alternatively, two primers of 17–20 nucleotides derived from both ends of the SEQ ID NO:1 (i.e., within the region of SEQ ID NO:1 bounded by the 5' nucleotide and the 3' nucleotide of the clone) are synthesized and used to amplify the IL-20 cDNA using the deposited cDNA plasmid as a template. The polymerase chain reaction is carried out under routine conditions, for instance, in 25 ul of reaction mixture with 0.5 ug of the above cDNA template. A convenient reaction mixture is 1.5–5 mM $MgCl_2$, 0.01% (w/v) gelatin, 20 uM each of dATP, dCTP, dGTP, dTTP, 25 pmol of each primer and 0.25 Unit of Taq polymerase. Thirty five cycles of PCR (denaturation at 94° C. for 1 min; annealing at 55° C. for 1 min; elongation at 72° C. for 1 min) are performed with a Perkin-Elmer Cetus automated thermal cycler. The amplified product is analyzed by agarose gel electrophoresis and the DNA band with expected molecular weight is excised and purified. The PCR product is verified to be the selected sequence by subcloning and sequencing the DNA product.

Several methods are available for the identification of the 5' or 3' non-coding portions of the IL-20 gene which may not be present in the deposited clone. These methods include but are not limited to, filter probing, clone enrichment using specific probes, and protocols similar or identical to 5' and 3' "RACE" protocols which are well known in the art. For instance, a method similar to 5' RACE is available for generating the missing 5' end of a desired full-length transcript. (Fromont-Racine et al., Nucleic Acids Res. 21(7):1683–1684 (1993).)

Briefly, a specific RNA oligonucleotide is ligated to the 5' ends of a population of RNA presumably containing full-length gene RNA transcripts. A primer set containing a primer specific to the ligated RNA oligonucleotide and a primer specific to a known sequence of the IL-20 gene of interest is used to PCR amplify the 5' portion of the IL-20 full-length gene. This amplified product may then be sequenced and used to generate the full length gene.

This above method starts with total RNA isolated from the desired source, although poly-A+RNA can be used. The RNA preparation can then be treated with phosphatase if necessary to eliminate 5' phosphate groups on degraded or damaged RNA which may interfere with the later RNA ligase step. The phosphatase should then be inactivated and the RNA treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase.

This modified RNA preparation is used as a template for first strand cDNA synthesis using a gene specific oligonucleotide. The first strand synthesis reaction is used as a template for PCR amplification of the desired 5' end using a primer specific to the ligated RNA oligonucleotide and a primer specific to the known sequence of the gene of interest. The resultant product is then sequenced and analyzed to confirm that the 5' end sequence belongs to the IL-20 gene.

Example 2

Isolation of IL-20 Genomic Clones

A human genomic P1 library (Genomic Systems, Inc.) is screened by PCR using primers selected for the cDNA sequence corresponding to SEQ ID NO:1., according to the method described in Example 1. (See also, Sambrook.)

Example 3

Expression and Purification of "His-tagged" IL-20 in *E. coli*

The bacterial expression vector pQE9 (pD10) is used for bacterial expression in this example. (QIAGEN, Inc., 9259 Eton Avenue, Chatsworth, Calif., 91311). pQE9 encodes ampicillin antibiotic resistance ("Ampr") and contains a bacterial origin of replication ("ori"), an IPTG inducible promoter, a ribosome binding site ("RBS"), six codons encoding histidine residues that allow affinity purification using nickel-nitrilo-tri-acetic acid ("Ni-NTA") affinity resin sold by QIAGEN, Inc., supra, and suitable single restriction enzyme cleavage sites. These elements are arranged such that an inserted DNA fragment encoding a polypeptide expresses that polypeptide with the six His residues (i e., a "6×His tag") covalently linked to the amino terminus of that polypeptide.

The DNA sequence encoding the desired portion of the IL-20 protein comprising the mature form of the IL-20 amino acid sequence is amplified from the deposited cDNA clone using PCR oligonucleotide primers which anneal to the amino terminal sequences of the desired portion of the IL-20 protein and to sequences in the deposited construct 3' to the cDNA coding sequence. Additional nucleotides containing restriction sites to facilitate cloning in the pQE9 vector are added to the 5' and 3' primer sequences, respectively.

For cloning the mature form of the IL-20 protein, the 5' primer has the sequence 5' GAT CGC <u>GGA TCC</u> CAG CCC AGG AGC CCC AAA AGC AAG AGG AAG-3' (SEQ ID NO:5) containing the underlined Bam I restriction site followed by 30 nucleotides of the amino terminal coding sequence of the mature IL-20 sequence in SEQ ID NO:2. One of ordinary skill in the art would appreciate, of course, that the point in the protein coding sequence where the 5' primer begins may be varied to amplify a DNA segment encoding any desired portion of the complete IL-20 protein shorter or longer than the mature form of the protein. The 3' primer has the sequence 5' GAT CGC <u>AAG CTT</u> CAG GTT TAT CAG AAG ATG CAG GTG CAG CCC ACA GC-3' (SEQ ID NO:6) containing the underlined Hind III restriction site followed by 35 nucleotides complementary to the 3' end of the coding sequence of the IL-20 DNA sequence in FIG. 1.

The amplified IL-20 DNA fragment and the vector pQE9 are digested with Bam I and Hind III and the digested DNAs are then ligated together. Insertion of the IL-20 DNA into the restricted pQE9 vector places the IL-20 protein coding region downstream from the IPTG-inducible promoter and in-frame with an initiating AUG and the six histidine codons.

The ligation mixture is transformed into competent *E. coli* cells using standard procedures such as those described by Sambrook and colleagues (*Molecular Cloning: a Laboratory Manual*, *2nd Ed.*; Cold Spring Harbor Laboratory Press, Cold Spring Harbor, N.Y. (1989)). *E. coli* strain M15/rep4, containing multiple copies of the plasmid pREP4, which expresses the lac repressor and confers kanamycin resistance ("Kanr"), is used in carrying out the illustrative example described herein. This strain, which is only one of many that are suitable for expressing IL-20 protein, is available commercially (QIAGEN, Inc., supra). Transformants are identified by their ability to grow on LB plates in the presence of ampicillin and kanamycin. Plasmid DNA is isolated from resistant colonies and the identity of the cloned DNA confirmed by restriction analysis, PCR and DNA sequencing.

Clones containing the desired constructs are grown overnight ("O/N") in liquid culture in LB media supplemented with both ampicillin (100 μg/ml) and kanamycin (25 μg/ml). The O/N culture is used to inoculate a large culture, at a dilution of approximately 1:25 to 1:250. The cells are grown to an optical density at 600 nm ("OD600") of between 0.4 and 0.6. Isopropyl-β-D-thiogalactopyranoside ("IPTG") is then added to a final concentration of 1 mM to induce transcription from the lac repressor sensitive promoter; by inactivating the lad repressor. Cells subsequently are incubated further for 3 to 4 hours. Cells then are harvested by centrifugation.

The cells are then stirred for 3–4 hours at 4° C. in 6M guanidine-HCl, pH 8. The cell debris is removed by centrifugation, and the supernatant containing the IL-20 is loaded onto a nickel-nitrilo-tri-acetic acid ("Ni-NTA") affinity resin column (QIAGEN, Inc., supra). Proteins with a 6×His tag bind to the Ni-NTA resin with high affinity and can be purified in a simple one-step procedure (for details see: The QIAexpressionist, 1995, QIAGEN, Inc., supra). Briefly the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the IL-20 is eluted with 6 M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M-1M urea gradient in 500 mM NaCl, 20% glycerol, 20 mM Tris/HCl pH 7.4, containing protease inhibitors. The renaturation should be performed over a period of 1.5 hours or more. After renaturation the proteins can be eluted by the addition of 250 mM immidazole. Immidazole is removed by a final dialyzing step against PBS or 50 mM sodium acetate pH 6 buffer plus 200 mM NaCl. The purified protein is stored at 4° C. or frozen at −80° C.

The following alternative method may be used to purify IL-20 expressed in *E. coli* when it is present in the form of inclusion bodies. Unless otherwise specified, all of the following steps are conducted at 4–10° C.

Upon completion of the production phase of the *E. coli* fermentation, the cell culture is cooled to 4–10° C. and the cells are harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells ware then lysed by passing the solution through a microfluidizer (Microfuidics, Corp. or APV Gaulin, Inc.) twice at 4000–6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2–4 hours. After 7000×g centrifugation for 15 min., the pellet is discarded and the IL-20 polypeptide-containing supernatant is incubated at 4° C. overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4° C. without mixing for 12 hours prior to further purification steps.

To clarify the refolded IL-20 polypeptide solution, a previously prepared tangential filtration unit equipped with 0.16 μm membrane filter with appropriate surface area (e.g., Filtron), equilibrated with 40 mM sodium acetate, pH 6.0 is employed. The filtered sample is loaded onto a cation exchange resin (e.g., Poros HS-50, Perseptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 mm of the effluent is continuously monitored. Fractions are collected and further analyzed by SDS-PAGE.

Fractions containing the IL-20 polypeptide are then pooled and mixed with 4 volumes of water. The diluted sample is then loaded onto a previously prepared set of tandem columns of strong anion (Poros HQ-50, Perseptive Biosystems) and weak anion (Poros CM-20, Perseptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant $A_{280}$ monitoring of the effluent. Fractions containing the IL-20 polypeptide (determined, for instance, by 16% SDS-PAGE) are then pooled.

The resultant IL-20 polypeptide exhibits greater than 95% purity after the above refolding and purification steps. No major contaminant bands are observed from Commassie blue stained 16% SDS-PAGE gel when 5 μg of purified protein is loaded. The purified protein is also tested for endotoxin/LPS contamination, and typically the LPS content is less than 0.1 ng/ml according to LAL assays.

IL-20 was expressed essentially as described above from a related bacterial expression vector designated pHE-4. In expression studies using the W3110 strain of *E. coli*, IL-20 polypeptide is found in inclusion bodies. The IL-20 polypeptide present in inclusion bodies was solubilized with 3–4 M guanidine in 0.1 M Na phosphate buffer, pH 8, 10 nM EDTA. Extraction performed with 4 M or 8 M urea resulted in apparent proteolytic degradation of the induced IL-20 protein upon dilution of the urea concentration to 4M or after dialysis against 50 mM sodium acetate buffer, pH 6, 0.1M NaCl, 2 mM EDTA . The 4 M guanidine extract of IL-20 inclusion bodies was found to retain solubility and remain intact after dilution to 0.3 M guanidine if extracted overnight in the presence of 10 mM DTT or 5 mM cysteine.

As IL-20 contains 8 cysteine residues, it was of interest to analyze whether or not the reason for the protein being insoluble after removal of guanidine was due to the presence of disulfide-linked aggregates. SDS-PAGE analysis of the 0.3M guanidine solubilized fraction under non-reducing conditions resulted in a higher electrophorectic mobility versus reduced sample suggestive of intramolecular disulfide bond formation. In addition, no high molecular weight species were noted. Also, size exclusion analysis in the presence of 0.4M guanidine indicated that the protein is either a monomer or dimer and is not present as a high molecular weight homo- or hetero-protein aggregates. The only time IL-20 disulfide-linked aggregates were found using these methods was when inclusion bodies were solubilized in the presence of reduced/oxidized glutathione.

Lowering of the guanidine concentration by dialysis against 0.1 M NaCl in buffers at pH 5.5, 6, 8, or 9 all resulted in precipitation of the protein along with other impurities. However, after dialysis against pH 3.5 acetate buffer in 0.125 M NaCl there was a significant amount of soluble IL-20 which was about ~70% pure. Attempts to further purify IL-20 by HS chromatography were not successful as the majority of the protein was not able to be eluted from the column; a minor amount was eluted at 1 M NaCl but showed negative enrichment. In addition, size exclusion analysis of the pH 3.5 soluble IL-20 was found to elute as an aggregate and as a broad included peak suggestive of interaction with column or as protein subunits displaying monomer/dimer equilibrium. This did effect some enrichment of the protein but with poor yield. Thus, the data indicate that under all present conditions employed IL-20 did not retain significant solubility in the absence of guanidine but displayed limited solubility at pH 3.5.

To produce IL-20 that was soluble under physiologic pH, solubilization conditions were employed to optimize the yield of soluble protein. The protein extracts solubilized in 4 M guanidine from inclusions bodies were allowed to "refold" in the absence and presence of reducing agent (5 mM cysteine) at 4 different concentrations of guanidine (i.e., from 0.75 to 0.075 M) and at either pH 7 or 8. Under these conditions the best yield of IL-20 was found in the pH 7 in the presence of cysteine. However, after dialysis to remove all the guanidine there was complete proteolysis of IL-20 to lower molecular weight species. Attempts to block proteolysis with protease inhibitors was not effective. In addition, rapid dilution of the guanidine extract followed by binding to cation exchange column was tried in an attempt to avoid proteolysis by separating this activity from IL-20. Upon elution from the HS column there was no enrichment for intact IL-20 and the yield of soluble intact protein was poor.

Amino acid residues Gln-21 through Phe-180 of the IL-20 polypeptide shown in FIG. 1 and in SEQ ID NO:2 were expressed from the pHE-4 bacterial expression vector as described above with the following modifications. IL-20 polypeptide was prepared by extraction of inclusion bodies in 4M guanidine in extract buffer (0.1M TRIS buffer, pH 8, 2 MM EDTA) in the presence of 13 mM DTT. The extract was diluted in extract buffer after 1 h to guanidine and DTT concentrations of 1.5 M and 5 mM, respectively. After 24 h at 4° C. the extract was centrifuged and dialyzed against 50 mM sodium acetate pH 5, 0.15M NaCl, 2 mM EDTA. The pH 5 dialysate was centrifuged, diluted to 8.4 mS conductivity and passed over an anion exchange column (HQ-Poros50). The protein did not bind. This protein was ~90% pure with an N-terminal sequence of MQPRS.

An additional bacterial expression construct was generated to express amino acid residues Arg-23 through Phe-180 of the IL-20 sequence shown in FIG. 1 and SEQ ID NO:2. This IL-20 bacterial expression construct was transformed into W3110 *E. coli* cells and induced with IPTG. The Arg-23/Phe-180 IL-20 polypeptide was expressed and found in inclusion bodies. The inclusion bodies were washed and solubilized with 2–4M guanidine-HCl and the protein was examined by gel electrophoresis.

Example 4

Cloning and Expression of IL-20 Protein in a Baculovirus Expression System

In this illustrative example, the plasmid shuttle vector pA2 is used to insert the cloned DNA encoding complete protein, including its naturally associated secretory signal (leader) sequence, into a baculovirus to express the mature IL-20 protein, using standard methods as described by Summers and colleagues (*A Manual of Methods for Baculovirus Vectors and Insect Cell Culture Procedures*, Texas Agricultural Experimental Station Bulletin No. 1555 (1987)). This expression vector contains the strong polyhedrin promoter of the *Autographa californica* nuclear polyhedrosis virus (ACMNPV) followed by convenient restriction sites such as Bam HI, Xba I and Asp 718. The polyadenylation site of the simian virus 40 ("SV40") is used for efficient polyadenylation. For easy selection of recombinant virus, the plasmid contains the beta-galactosidase gene from *E. coli* under control of a weak Drosophila promoter in the same orientation, followed by the polyadenylation signal of the polyhedrin gene. The inserted genes are flanked on both sides by viral sequences for cell-mediated homologous recombination with wild-type viral DNA to generate a viable virus that express the cloned polynucleotide.

Many other baculovirus vectors could be used in place of the vector above, such as pAc373, pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, by Luckow and coworkers (*Virology* 170:31–39 (1989)).

The cDNA sequence encoding the full length IL-20 protein in the deposited clone, including the AUG initiation codon and the naturally associated leader sequence shown in SEQ ID NO:2, is amplified using PCR oligonucleotide primers corresponding to the 5' and 3' sequences of the gene. The 5' primer has the sequence 5' GAT CGC GGA TCC GCC ATC ATG GAC TGG CCT CAC AAC CTG CTG TTT CTT CTT AC 3' (SEQ ID NO:7) containing the underlined Bam HI restriction enzyme site, an efficient signal for initiation of translation in eukaryotic cells (Kozak, M., *J. Mol. Biol.* 196:947–950 (1987)), followed by 35 of nucleotides of the sequence of the complete IL-20 protein shown in FIG. 1, beginning with the AUG initiation codon. The 3' primer has the sequence 5' GAT CGC GGT ACC CAG GTT TAT CAG AAG ATG CAG GTG CAG CCC ACA GC 3' (SEQ ID NO:8) containing the underlined Asp 718 restriction site followed by 35 nucleotides complementary to the 3' noncoding sequence in FIG. 1.

The amplified fragment is isolated from a 1% agarose gel using a commercially available kit ("Geneclean," BIO 101 Inc., La Jolla, Calif.). The fragment then is digested with Bam HI and Asp 718 and again is purified on a 1% agarose gel. This fragment is designated herein F1.

The plasmid is digested with the restriction enzymes Bam HI and Asp 718 and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.). This vector DNA is designated herein "V1".

Fragment F1 and the dephosphorylated plasmid V1 are ligated together with T4 DNA ligase. *E. coli* HB 101 or other suitable *E. coli* hosts such as XL-1 Blue (Statagene Cloning Systems, La Jolla, Calif.) cells are transformed with the ligation mixture and spread on culture plates. Bacteria are identified that contain the plasmid with the human IL-20 gene by digesting DNA from individual colonies using Bam HI and Asp 718 and then analyzing the digestion product by gel electrophoresis. The sequence of the cloned fragment is confirmed by DNA sequencing. This plasmid is designated herein pA2IL-20.

Five μg of the plasmid pA2L-20 is co-transfected with 1.0 μg of a commercially available linearized baculovirus DNA ("BaculoGold™ baculovirus DNA", Pharmingen, San Diego, Calif.),.using the lipofection method described by Felgner and colleagues (*Proc. Natl. Acad. Sci. USA* 84:7413–7417 (1987)). One μg of BaculoGold™ virus DNA and 5 μg of the plasmid pA2IL-20 are mixed in a sterile well of a microtiter plate containing 50 μl of serum-free Grace's medium (Life Technologies Inc., Gaithersburg, Md.). Afterwards, 10 μl Lipofectin plus 90 μl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is then incubated for 5 hours at 27° C. The transfection solution is then removed from the plate and 1 ml of Grace's insect medium supplemented with 10% fetal calf serum is added. Cultivation is then continued at 27° C. for four days.

After four days the supernatant is collected and a plaque assay is performed, as described by Summers and Smith (supra). An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10). After appropriate incubation, blue stained plaques are picked with the tip of a micropipettor (e.g., Eppendorf). The agar containing the recombinant viruses is then resuspended in a microcentrifuge tube containing 200 μl of Grace's medium and the suspension containing the recombinant baculovirus is used to infect Sf9 cells seeded in 35 mm dishes. Four days later the supernatants of these culture dishes are harvested and then they are stored at 4° C. The recombinant virus is called V-IL-20.

To verify the expression of the IL-20 gene Sf9 cells are grown in Grace's medium supplemented with 10% heat-inactivated FBS. The cells are infected with the recombinant baculovirus V-IL-20 at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 μCi of $^{35}$S-methionine and 5 μCi $^{35}$S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the mature form of the IL-20 protein, and thus the cleavage point and length of the naturally associated secretory signal peptide.

Example 5

Cloning and Expression of IL-20 in Mammalian Cells

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRs) from Retroviruses, e.g., RSV, HTLV1, HIVI and the early promoter of the cytomegalovirus (CMV). However, cellular elements can also be used (e.g., the human actin promoter). Suitable expression vectors for use in practicing the present invention include, for example, vectors such as pSVL and pMSG (Pharmacia, Uppsala, Sweden), pRSVcat (ATCC 37152), pSV2dhfr (ATCC 37146) and pBC12MI (ATCC 67109). Mammalian host cells that could be used include, human Hela, 293, H9 and Jurkat cells, mouse NIH3T3 and C127 cells, Cos 1, Cos 7 and CV1, quail QC1–3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) marker is useful to develop cell lines that carry several hundred or even several thousand copies of the gene of interest. Another useful selection marker is the enzyme glutamine synthase (G S; Murphy, et al., *Biochem J.* 227:277–279 (1991); Bebbington, et al., *Bio/Technology* 10:169–175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

The expression vectors pC1 and pC4 contain the strong promoter (LTR) of the Rous Sarcoma Virus (Cullen, et al., *Mol. Cel. Biol.* 5:438–447 (1985)) plus a fragment of the CMV-enhancer (Boshart, et al., *Cell* 41:521–530 (1985)). Multiple cloning sites, e.g., with the restriction enzyme cleavage sites Bam HI, Xba I and Asp 718, facilitate the cloning of the gene of interest. The vectors contain in addition the 3' intron, the polyadenylation and termination signal of the rat preproinsulin gene.

Example 5(a)

Cloning and Expression in COS Cells

The expression plasmid, pIL-20HA, is made by cloning a portion of the cDNA encoding the mature form of the IL-20 protein into the expression vector pcDNAI/Amp or pcDNAIII (which can be obtained from Invitrogen, Inc.).

The expression vector pcDNAI/amp contains: (1) an *E. coli* origin of replication effective for propagation in *E. coli* and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron; (5) several codons encoding a hemagglutinin fragment (i.e., an "HA" tag to facilitate purification) followed by a termination codon and polyadenylation signal arranged so that a cDNA can be conveniently placed under expression control of the CMV promoter and operably linked to the SV40 intron and the polyadenylation signal by means of restriction sites in the polylinker. The HA tag corresponds to an epitope derived from the influenza hemagglutinin protein described by Wilson and colleagues (*Cell* 37:767 (1984)). The fusion of the HA tag to the target protein allows easy detection and recovery of the recombinant protein with an antibody that recognizes the HA epitope. pcDNAIII contains, in addition, the selectable neomycin marker.

A DNA fragment encoding the complete IL-20 polypeptide is cloned into the polylinker region of the vector so that recombinant protein expression is directed by the CMV promoter. The plasmid construction strategy is as follows. The IL-20 cDNA of the deposited clone is amplified using primers that contain convenient restriction sites, much as described above for construction of vectors for expression of IL-20 in *E. coli*. Suitable primers include the following, which are used in this example. The 5' primer, containing the underlined Asp 718 site, a Kozak sequence, an AUG start codon, and 35 nucleotides of the 5' coding region of the complete IL-20 polypeptide, has the following sequence: 5' GAT CGC <u>GGT ACC</u> GCC ATC ATG GAC TOG CCT CAC AAC CTG CTG TTT CTT CTT AC 3' (SEQ ID NO:9). The 3' primer, containing the underlined Bam HI and 35 of nucleotides complementary to the 3' coding sequence immediately before the stop codon, has the following sequence: 5' GAT CGC <u>GGA TCC</u> CAG GTT TAT CAG AAG ATG CAG GTG CAG CCC ACA GC 3' (SEQ ID NO:10).

The PCR amplified DNA fragment and the vector, pcDNAI/Amp, are digested with Bam HI and Avp 718 and then ligated. The ligation mixture is transformed into *E. coli* strain SURE (Stratagene Cloning Systems, La Jolla, Calif. 92037), and the transformed culture is plated on ampicillin media plates which then are incubated to allow growth of ampicillin resistant colonies. Plasmid DNA is isolated from resistant colonies and examined by restriction analysis or other means for the presence of the fragment encoding the complete IL-20 polypeptide. For expression of recombinant IL-20, COS cells are transfected with an expression vector, as described above, using DEAE-dextran, as described, for instance, by Sambrook and coworkers (*Molecular Cloning: a laboratory Manual*, Cold Spring Laboratory Press, Cold Spring Harbor, N.Y. (1989)). Cells are incubated under conditions for expression of IL-20 by the vector.

Expression of the IL-20-HA fusion protein is detected by radiolabeling and immunoprecipitation, using methods described in, for example Harlow and colleagues (*Antibodies: A Laboratory Manual*, *2nd Ed.*; Cold Spring Harbor Laboratory Press, Cold Spring Harbor, N.Y. (1988)). To this end, two days after transfection, the cells are labeled by incubation in media containing $^{35}$S-cysteine for 8 hours. The cells and the media are collected, and the cells are washed and the lysed with detergent-containing RIPA buffer: 150 mM NaCl, 1% NP-40, 0.1% SDS, 1% NP-40, 0.5% DOC, 50 mM TRIS, pH 7.5, as described by Wilson and colleagues (supra). Proteins are precipitated from the cell lysate and from the culture media using an HA-specific monoclonal antibody. The precipitated proteins then are analyzed by SDS-PAGE and autoradiography. An expression product of the expected size is seen in the cell lysate, which is not seen in negative controls.

Example 5(b)

Cloning and Expression in CHO Cells

The vector pC4 is used for the expression of IL-20 polypeptide. Plasmid pC4 is a derivative of the plasmid pSV2-dhfr (ATCC Accession No. 37146). The plasmid contains the mouse DHFR gene under control of the SV40 early promoter. Chinese hamster ovary- or other cells lacking dihydrofolate activity that arc transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., et al., *J. Biol. Chem.* 253:1357–1370 (1978); Hamlin, J. L. and Ma, C. *Biochem. et Biophys. Acta*, 1097:107–143 (1990); Page, M. J. and Sydenham, M. A. *Biotechnology* 9:64–68 (1991)). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains for expressing the gene of interest the strong promoter of the long terminal repeat (LTR) of the Rouse Sarcoma Virus (Cullen, et al., *Mol. Cell. Biol.* 5:438–447 (1985)) plus a fragment isolated from the enhancer of the immediate early gene of human cytomegalovirus (CMV; Boshart, et al., *Cell* 41:521–530 (1985)). Downstream of the promoter are the following single restriction enzyme cleavage sites that allow the integration of the genes: Bam HI, Xba I, and Asp 718. Behind these cloning sites the plasmid contains the 3' intron and polyadenylation site of the rat preproinsulin gene. Other high efficiency promoters can also be used for the expression, e.g., the human β-actin promoter, the SV40 early or late promoters or the long terminal repeats from other retroviruses, e.g., HIV and HTLVI. Clontech's Tet-Off and Tet-On gene expression systems and similar systems can be used to express the IL-20 polypeptide in a regulated way in mammalian cells (Gossen, M., and Bujard, H. *Proc. Natl. Acad. Sci. USA* 89:5547–5551 (1992)). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction enzymes Bam HI and Asp 718 and then dephosphorylated using calf intestinal phosphates by procedures known in the art. The vector is then isolated from a 1% agarose gel.

The DNA sequence encoding the complete IL-20 polypeptide is amplified using PCR oligonucleotide primers corresponding to the 5' and 3' sequences of the desired portion of the gene. The 5' primer containing the underlined Bam HI site, a Kozak sequence, an AUG start codon, and 35 nucleotides of the 5' coding region of the complete IL-20 polypeptide, has the following sequence: 5'-GAT CGC GGA TCC GCC ATC ATG GAC TGG CCT CAC AAC CTG CTG TTT CTT CTT AC-3' (SEQ ID NO:7). The 3' primer, containing the underlined Asp 718 and 35 of nucleotides complementary to the 3' coding sequence immediately before the stop codon as shown in FIG. 1 (SEQ ID NO:1), has the following sequence: 5'-GAT CGC GGT ACC CAG GTT TAT CAG AAG ATG CAG GTG CAG CCC ACA GC-3' (SEQ ID NO:8).

The amplified fragment is digested with the endonucleases Bam HI and Asp 718 and then purified again on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. Five μg of the expression plasmid pC4 is cotransfected with 0.5 μg of the plasmid pSVneo using lipofectin (Felgner, et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 μM, 2 μM, 5 μM, 10 mM, 20 mM). The same procedure is repeated until clones are obtained which grow at a concentration of 100–200 μM. Expression of the desired gene product is analyzed, for instance, by SDS-PAGE and Western blot or by reversed phase HPLC analysis.

Example 5(c)

Analysis of IL-20 Polypeptides Expressed in COS and CHO Cells

IL-20 CHO clones were selected by RT-PCR and amplified to 1 micromolar of methotrexate (Irina Knyazev, PD). Conditioned media (CHO-5 serum-free media without methotrexate) from 7 CHO clones were analyzed for IL-20 expression by SDS-PAGE followed by silver staining. Comparison of the protein pattern in conditioned media from IL-20 clones versus the control pC4 media revealed that several clones (numbers 7, 10, 16 & 44) expressed a novel protein of ~20 kDa not present in pC4 media. The conditioned media was also analyzed by RP-HPLC analysis and a unique peak was present in IL-20 conditioned media compared to pC4 media; the peak from one positive clone, #16, was collected and subjected to N-terminal sequence analysis. The N-terminal sequence SRMKP, was found. These results indicate that the unique HPLC peak corresponds to IL-20, however, this sequence starts at residue 51 and not at residue 23 like the baculovirus-expressed IL-20 protein.

Three CHO clones (numbers 10, 16 and 20) were selected for continued amplification in the presence of 10 micromolar methotrexate (Irina Knyazev, PD). SDS-PAGE analysis of the conditioned media under serum-free conditions in CHO 5 media revealed the presence of two novel protein bands when compared to pC4 vector conditioned media from 2 and 6 day samples. These bands had apparent molecular sizes of ~20 and 23 kDa. Western blot and N-terminal sequence analyses were performed in order to determine if the 23 and 20 kDa bands correspond to full-length secreted and the previously observed truncated versions of IL-20 and/or to differentially glycosylated species. The conditioned media were subjected to SDS-PAGE analysis and the gels blotted onto ProBlott membrane. The N-terminal sequence analysis of the 20 and 23 kDa bands revealed that the lower 20 kDa band corresponded to the truncated protein having the sequence, SRMKP (which corresponds to amino acids Ser-51 presumably through Phe-180 of the IL-20 sequence shown in FIG. 1 (SEQ ID NO:2), but also may correspond with one or more polypeptides beginning with Ser-51 and ending with any amino acid located at or near the IL-20 C-terminus, for example Ile-179, Cys-178, Thr-177, Cys-176, Gly-175, Val-174, Ala-173, Ile-172, Thr-171, Glu-170, or any other combination of amino acids provided in the N- and C-terminal deletion lists provided in the specification). The sequence of the upper band did not appear to be IL-20 suggesting that the N-terminus is blocked (possibly with a pyroglutamic residue as the mature form of IL-20 is predicted by SignalP to start at glutamine residue 21 (FIG. 1 (SEQ ID NO:2))). Western blots were performed using the rabbit anti-IL-20 sera prepared against the bacterially expressed protein; the *E. coli*-expressed protein was used as positive control. The results indicated that both the 20 and 23 kDa bands bind to the antibody and no binding observed with the pC4 control conditioned media. Moreover, as the lower 20 kDa band had the same apparent mobility as the full-length *E. coli* protein indicating that it is glycosylated like the 23 kDa band; this is consistent with the presence of a single N-glycosylation site at residue 75 which would still be present in the truncated protein. The blot also revealed the presence of other apparent minor breakdown products of IL-20. Thus, overall the data indicate that the major unique protein species expressed by the CHO clones correspond to IL-20 with the upper band apparently representing full-length protein and lower a proteolytically cleaved species.

Further analyses of IL-20 polypeptide preparations produced in CHO cell cultures resulted in the following observations. Day 4 conditioned media (325 mL) from IL-20 expressing clone #16 grown in T-flasks was purified. The pH of the media was adjusted to pH 6 to increase binding to the strong-cation exchange resin (Poros HS50). The HS50 bound material was eluted with increasing concentration of NaCl and analyzed by SDS-PAGE. Major protein bands of ~23 and 22 kDa and minor bands of 18 and 14 kDa were observed in both the 0.5 and 0.8M NaCl fractions which were similar in size to bands previously detected in conditioned media by immunoblot analysis of conditioned media). Immunoblot analysis of the 0.8M NaCl HS50 fractions indicated that all of these bands were IL-20. No immunoreactive bands were detected in the material not bound to the HS50 column indicating that under these conditions IL-20 binds quantitatively to the cation exchange column.

The 23 and 22 kDa IL-20 bands were subjected to N-terminal sequence analysis. The 23 kDa had three closely spaced N-termini starting at Ser27, Arg29 and Lys30 (FIG. 1 (SEQ ID NO:2)). Whereas the 18 kDa IL-20 band had two N-termini starting at residues Ser51 and Met53 (FIG. 1 (SEQ ID NO:2)). The presence of truncated forms of the protein are indicative of post-translational proteolytic processing. This appears to be a trypsin-like activity as the N-termini, Arg29, Ser 30 and Met52 (FIG. 1 (SEQ ID NO:2)) are preceded by a basic residue. Ser51 (FIG. 1 (SEQ ID NO:2)) is preceded by a valine residue and may not be processed by the same enzyme. The N-terminus of baculovirus expressed IL-20 was residue Arg23 (FIG. 1 (SEQ ID NO:2)). Thus, under present conditions IL-20 present in CHO conditioned media appears to be present in several forms due to post-translational proteolysis. Whether or not all these forms retain biological activity are not yet known.

In repeated analyses of purification protocols which might be responsible for the presence of truncated forms of IL-20, the conditioned media was left at pH 7. In addition, a serine protease inhibitor (Pefabloc) and a cysteine protease inhibitor (E64) were added. The conditioned media were applied to the HS50 column and the bound proteins analyzed by SDS-PAGE. Under these conditions the IL-20 was eluted in the 0.5M (FIG. 1, CHO 22 and 16; lanes 1 & 2, respectively) and 0.8M NaCl and was approximately 80% pure. However, significantly less of the 16 and 14 kDa forms were present. In addition, there was a more distinct 23 kDa band present in this preparation compared to the IL-20 purified from the T flask conditioned media. After 24 h there was an appearance of the 18 and 16 kDa forms in the HS50 fractions. It appears that the processing to the 18 and 16 kDa forms still occurs in the HS50 fraction despite addition of the E64 and Pefabloc protease inhibitors.

N-terminal sequence analysis of this band revealed an IL-20 N-terminus starting at residue Arg23 (40%) which is the same as baculovirus-expressed IL-20 In addition, N-termini starting at residue Arg29 (20%) and Lys30 (20%) were also observed. Thus, as in baculovirus-expressed IL-20, after cleavage of the signal peptide the secreted protein the N-termninus starts with residue Arg23 (FIG. 1 (SEQ ID NO:2)).

The 0.5 and 0.8M NaCl HS50 fractions were analyzed for binding to the IL-17-like receptor by BIAcore analysis (see Example 31). The peak fractions were pooled and dialyzed against 25 mM HEPES buffer, pH 7.2, 0.1M NaCl. Binding activity was found in the 0.5 and 0.8M NaCl fractions but not in IL-20 negative fractions (as indicated by SDS-PAGE). The greatest binding was found in the 0.8M NaCl fraction which is enriched for the full length mature protein (Arg23) (FIG. 1 (SEQ ID NO:2)). The binding appeared to be specific because it showed saturation with increasing concentrations of protein and little binding was observed to a non-derivatized control dextran surface.

The IL-20 protein purified from CHO conditioned media displayed variability in ratio of the major proteolytically processed forms which had apparent molecular masses by SDS-PAGE of ~23, 22 and 18 kDa. The N-termini of the 23, 22, and 18 kDa forms are R23 (full-length), S27, R29, S30 (delta 4, 6 & 7), and S51 & M52 (delta 30 & 31), respectively (FIG. 1 (SEQ ID NO:2)).

There was quite significant variability in the ratio of the different forms found in spinner cultures compared to Bioreactor cultures. The lower cell density spinner cultures displayed less processing to the 18 kDa forms. The data suggested that the proteolytic processing was cell density dependent. It was also noted that there was no change in the amount of the lower MW forms after 1 weeks storage of the media at 4° C. (in the presence of 5 mM EDTA).

Several chromatographic separations were tried in an attempt to separate the 23/22 and 18 kDa forms including heparin affinity chromatography, weak-cation exchange and size separation. In all cases no significant separation was observed suggesting that the proteolytic processed and full length forms form heteroligomeric forms. The size exclusion data are consistent with a dimeric structure.

Example 6

Tissue Distribution of IL-20 mRNA Expression

Northern blot analysis is carried out to examine IL-20 gene expression in human tissues, using methods described by, among others, Sambrook and colleagues (supra). A cDNA probe containing the entire nucleotide sequence of the IL-20 protein (SEQ ID NO:1) is labeled with $^{32}P$ using the rediprime™ DNA labeling system (Amersham Life Science), according to manufacturer's instructions. After labeling, the probe is purified using a CHROMA SPIN-100™ column (Clontech Laboratories, Inc.), according to manufacturer's protocol number PT1200-1. The purified labeled probe is then used to examine various human tissues for IL-20 mRNA.

Multiple Tissue Northern (MTN) blots containing various human tissues (H) or human immune system tissues (IM) are obtained from Clontech and are examined with the labeled probe using ExpressHyb™ hybridization solution (Clontech) according to manufacturer's protocol number PT1190-1. Following hybridization and washing, the blots are mounted and exposed to film at −70° C. overnight, and films developed according to standard procedures. Results of Northern blot experiments performed essentially as described above indicate that a major mRNA of approximately 5 kb is detected predominantly in the thymus, and, to a lesser degree, in the adrenal cortex, spleen, pancreas, and only at very low levels in the lymph node, peripheral blood lymphocytes, fetal liver, adrenal medulla, thyroid, small intestine, stomach and heart. A major mRNA of approximately 1 kb, with a minor mRNA at approximately 5 kb was detected in additional experiments in the testis and spinal cord and, to a lesser extent, in bone marrow and small intestine.

Recent observations indicate that IL-20 mRNA itself is increased in activated T-cells when compared to resting T-cells.

Example 7

Effect of IL-20 on the Proliferation of HT-29 Cells

Human tumor cell lines including breast carcinoma MDA-MB-231, colon cancer HT-29, prostate cancer PC-3 and osteogenic sarcoma MNNG/HOS were obtained from ATCC and cultured in the medium recommended for each cell line by ATCC.

Tumor cells were harvested by trypsinization and seeded in wells of a 96-well plate at 5,000 cells/well in the appropriate growth medium. IL-20 protein (or supernatant) was then added at concentrations from 0 to 10000 ng/ml in basal medium. Taxol at a concentration of 50 ng/ml is used as a positive control. The appropriate buffer (without protein) is utilized as a negative control. The cells were incubated in a final volume of 200 ul for 4–5 days. AlamarBlue was added to each well to a final concentration of 10%. The cells are incubated for 4 hr. Cell viability was measured by reading in a CytoFluor fluorescence reader with excitation at 530 nm and emission at 590 nm.

Results from initial experiments performed essentially as described above indicate that IL-20 supernatants have stimulatory effects on the growth of HT-29 cells in vitro.

Example 8

Chromosomal Mapping of IL-20

An oligonucleotide primer set is designed according to the sequence at the 5' end of SEQ ID NO:1. This primer preferably spans about 100 nucleotides. This primer set is then used in a polymerase chain reaction under the following set of conditions: 30 seconds, 95° C.; 1 minute, 56° C.; 1 minute, 70° C. This cycle is repeated 32 times followed by one 5 minute cycle at 70° C. Human, mouse, and hamster DNA is used as template in addition to a somatic cell hybrid panel containing individual chromosomes or chromosome fragments (Bios, Inc). The reactions is analyzed on either 8% polyacrylamide gels or 3.5% agarose gels. Chromosome mapping is determined by the presence of an approximately 100 bp PCR fragment in the particular somatic cell hybrid.

Example 9

Construction of N-Terminal and/or C-Terminal Deletion Mutants

The following general approach may be used to clone a N-termninal or C-terminal IL-20 deletion mutant. Generally, two oligonucleotide primers of about 15–25 nucleotides are derived from the desired 5' and 3' positions of a polynucleotide of SEQ ID NO:1. The 5' and 3' positions of the primers are determined based on the desired IL-20 polynucleotide fragment. An initiation and stop codon are added to the 5' and 3' primers respectively, if necessary, to express the IL-20 polypeptide fragment encoded by the polynucleotide fragment. Preferred IL-20 polynucleotide fragments are those encoding the N-terminal and C-terminal deletion mutants disclosed above in the "Polynucleotide and Polypeptide Fragments" section of the Specification.

Additional nucleotides containing restriction sites to facilitate cloning of the IL-20 polynucleotide fragment in a desired vector may also be added to the 5' and 3' primer sequences. The IL-20 polynucleotide fragment is amplified from genomic DNA or from the deposited cDNA clone using the appropriate PCR oligonucleotide primers and conditions discussed herein or known in the art. The IL-20 polypeptide fragments encoded by the IL-20 polynucleotide fragments of the present invention may be expressed and purified in the same general manner as the full length polypeptides, although routine modifications may be necessary due to the differences in chemical and physical properties between a particular fragment and full length polypeptide.

As a means of exemplifying, but not limiting, the present invention, the polynucleotide encoding the IL-20 polypeptide fragment Ser-24 through Cys-178 (FIG. 1 (SEQ ID NO:2)) is amplified and cloned as follows: A 5' primer is generated comprising a restriction enzyme site followed by an initiation codon in frame with the polynucleotide sequence encoding the N-terminal portion of the polypeptide fragment beginning with Ser-24. A complementary 3' primer is generated comprising a restriction enzyme site followed by a stop codon in frame with the polynucleotide sequence encoding C-terminal portion of the IL-20 polypeptide fragment ending with Cys-178.

The amplified polynucleotide fragment and the expression vector are digested with restriction enzymes which recognize the sites in the primers. The digested polynucleotides are then ligated together. The IL-20 polynucleotide fragment is inserted into the restricted expression vector, preferably in a manner which places the IL-20 polypeptide fragment coding region downstream from the promoter. The ligation mixture is transformed into competent *E. coli* cells using standard procedures and as described in the Examples herein. Plasmid DNA is isolated from resistant colonies and the identity of the cloned DNA confirmed by restriction analysis, PCR and DNA sequencing.

Example 10

Protein Fusions of IL-20

IL-20 polypeptides are preferably fused to other proteins. These fusion proteins can be used for a variety of applications. For example, fusion of IL-20 polypeptides to His-tag, HA-tag, protein A, IgG domains, and maltose binding protein facilitates purification. (See Example 3; see also EP A 394,827; Traunecker, et al., *Nature* 331:84–86 (1988).) Similarly, fusion to IgG-1, IgG-3, and albumin increases the halflife time in vivo. Nuclear localization signals fused to IL-20 polypeptides can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made by modifying the following protocol, which outlines the fusion of a polypeptide to an IgG molecule, or the protocol described in Example 3.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector.

For example, if pC4 (Accession No. 209646) is used, the human Fc portion can be ligated into the Bam HI cloning site. Note that the 3' Bam HI site should be destroyed. Next, the vector containing the human Fc portion is re-restricted with Bam HI, linearizing the vector, and IL-20 polynucleotide, isolated by the PCR protocol described in Example 1, is ligated into this Bam HI site. Note that the polynucleotide is cloned without a stop codon, otherwise a fusion protein will not be produced. The sequence of the human IgG Fc region is as follows: 5'-GGG ATC CGG AGC CCA AAT CTT CTG ACA AAA CTC ACA CAT GCC CAC CGT GCC CAG CAC CTG AAT TCG AGG GTG CAC CGT CAG TCT TCC TCT TCC CCC CAA AAC CCA AGG ACA CCC TCA TGA TCT CCC GGA CTC CTG AGG TCA CAT GCG TGG TGG TGG ACG TAA GCC ACG AAG ACC CTG AGG TCA AGT TCA ACT GGT ACG TGG ACG GCG TGG AGG TGC ATA ATG CCA AGA CAA AGC CGC GGG AGG AGC AGT ACA ACA GCA CGT ACC GTG TGG TCA GCG TCC TCA CCG TCC TGC ACC AGG ACT GGC TGA ATG GCA AGG AGT ACA AGT GCA AGG TCT CCA ACA AAG CCC TCC CAA CCC CCA TCG AGA AAA CCA TCT CCA AAG CCA AAG GGC AGC CCC GAG AAC CAC AGG TGT ACA CCC TGC CCC CAT CCC GGG ATG AGC TGA CCA AGA ACC AGG TCA GCC TGA CCT GCC TGG TCA AAG GCT TCT ATC CAA GCG ACA TCG CCG TGG AGT GGG AGA GCA ATG GGC AGC CGG AGA ACA ACT ACA AGA CCA CGC CTC CCG TGC TGG ACT CCG ACG GCT CCT TCT TCC TCT ACA GCA AGC TCA CCG TGG ACA AGA GCA GGT GGC AGC AGG GGA ACG TCT TCT CAT GCT CCG TGA TGC ATG AGG CTC TGC ACA ACC ACT ACA CGC AGA AGA GCC TCT CCC TGT

CTC CGG GTA AAT GAG TGC GAC GGC CGC GAC TCT AGA GGA T-3' (SEQ ID NO:16).

If the naturally occurring signal sequence is used to produce the secreted protein, pC4 does not need a second signal peptide. Alternatively, if the naturally occurring signal sequence is not used, the vector can be modified to include a heterologous signal sequence. (See, e.g., WO 96/34891.)

Example 11

Production of an Antibody

The antibodies of the present invention can be prepared by a variety of methods. (See, Current Protocols, Chapter 2.) For example, cells expressing IL-20 are administered to an animal to induce the production of sera containing polyclonal antibodies. In a preferred method, a preparation of IL-20 protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or protein binding fragments thereof). Such monoclonal antibodies can be prepared using hybridoma technology. (Kohler, et al., *Nature* 256:495 (1975); Kohler, et al., *Eur. J. Immunol.* 6:511 (1976); Kohler, et al., *Eur. J. Immunol.* 6:292 (1976); Hammerling, et al., in: Monoclonal Antibodies and T-Cell Hybridomas, Elsevier, N.Y., pp. 563–681 (1981).) In general, such procedures involve immunizing an animal (preferably a mouse) with IL-20 polypeptide or, more preferably, with a secreted IL-20 polypeptide-expressing cell. Such cells may be cultured in any suitable tissue culture medium; however, it is preferable to culture cells in Earle's modified Eagle's medium supplemented with 10% fetal bovine serum (inactivated at about 56° C.), and supplemented with about 10 g/l of nonessential amino acids, about 1,000 U/ml of penicillin, and about 100 ug/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP20), available from the ATCC. After fusion, the resulting hybridoma cells are selectively maintained in HAT medium, and then cloned by limiting dilution as described by Wands et al. (Gastroenterology 80:225–232 (1981).) The hybridoma cells obtained through such a selection are then assayed to identify clones which secrete antibodies capable of binding the IL-20 polypeptide.

Alternatively, additional antibodies capable of binding to IL-20 polypeptide can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the IL-20 protein-specific antibody can be blocked by IL-20. Such antibodies comprise anti-idiotypic antibodies to the IL-20 protein-specific antibody and can be used to immunize an animal to induce formation of further IL-20 protein-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, secreted IL-20 protein-binding fragments can be produced through the application of recombinant DNA technology or through synthetic chemistry.

For in vivo use of antibodies in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. (See, for review, Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neubergeret al., Nature 314:268 (1985).)

Example 12

Production of IL-20 Protein for High-throughput Screening Assays

The following protocol produces a supernatant containing IL-20 polypeptide to be tested. This supernatant can then be used in the Screening Assays described in Examples 14–21.

First, dilute Poly-D-Lysine (644 587 Boehringer-Mannheim) stock solution (1 mg/ml in PBS) 1:20 in PBS (w/o calcium or magnesium 17-516F Biowhittaker) for a working solution of 50 ug/ml. Add 200 ul of this solution to each well (24 well plates) and incubate at RT for 20 minutes. Be sure to distribute the solution over each well (note: a 12-channel pipetter may be used with tips on every other channel). Aspirate the Poly-D-Lysine solution and rinse with 1 ml PBS (Phosphate Buffered Saline). The PBS should remain in the well until just prior to plating the cells and plates may be poly-lysine coated in advance for up to two weeks.

Plate 293T cells (do not carry cells past P+20) at $2\times10^5$ cells/well in 0.5 ml DMEM(Dulbecco's Modified Eagle Medium)(with 4.5 G/L glucose and L-glutarnine (12-604F Biowhittaker))/10% heat inactivated FBS(14-503F Biowhittaker)/1×Penstrep(17-602E Biowhittaker). Let the cells grow overnight.

The next day, mix together in a sterile solution basin: 300 ul Lipofectamine (18324-012 Gibco/BRL) and 5 ml Optimem I (31985070 Gibco/BRL)/96-well plate. With a small volume multi-channel pipetter, aliquot approximately 2 ug of an expression vector containing a polynucleotide insert, produced by the methods described in Examples 8–10, into an appropriately labeled 96-well round bottom plate. With a multi-channel pipetter, add 50 ul of the Lipofectamine/Optimem I mixture to each well. Pipette up and down gently to mix. Incubate at RT 15–45 minutes. After about 20 minutes, use a multi-channel pipetter to add 150 ul Optimem I to each well. As a control, one plate of vector DNA lacking an insert should be transfected with each set of transfections.

Preferably, the transfection should be performed by tag-teaming the following tasks. By tag-teaming, hands on time is cut in half, and the cells do not spend too much time on PBS. First, person A aspirates off the media from four 24-well plates of cells, and then person B rinses each well with 0.5-ml PBS. Person A then aspirates off PBS rinse, and person B, using a12-channel pipetter with tips on every other channel, adds the 200 ul of DNA/Lipofectamine/Optimem I complex to the odd wells first, then to the even wells, to each row on the 24-well plates. Incubate at 37° C. for 6 hours.

While cells are incubating, prepare appropriate media, either 1%BSA in DMEM with 1×penstrep, or HGS CHO-5 media (116.6 mg/L of CaCl2 (anhyd); 0.00130 mg/L $CuSO_4$—$5H_2O$; 0.050 mg/L of $Fe(NO_3)_3$—$9H_2O$; 0.417 mg/L of $FeSO_4$—$7H_2O$; 311.80 mg/L of KCl; 28.64 mg/L of $NaH_2PO_4$—$H_2O$; 71.02 mg/L of $Na_2$HPO4; 0.4320 mg/L of $ZnSO_4$—$7H_2O$; 0.002 mg/L of Arachidonic Acid; 1.022 mg/L of Cholesterol; 0.070 mg/L of DL-alpha-Tocopherol-Acetate; 0.0520 mg/L of Linoleic Acid; 0.010 mg/L of Linolenic Acid; 0.010 mg/L of Myristic Acid; 0.010 mg/L of Oleic Acid; 0.010 mg/L of Palmitric Acid; 0.010 mg/L of Palmitic Acid; 100 mg/L of Pluronic F-68; 0.010 mg/L of Stearic Acid; 2.20 mg/L of Tween 80; 4551 mg/L of D-Glucose; 130.85 mg/ml of L-Alanine; 147.50 mg/ml of L-Arginine-HCL; 7.50 mg/ml of L-Asparagine-$H_2O$; 6.65 mg/ml of L-Aspartic Acid; 29.56 mg/ml of L-Cystine-2HCL—$H_2O$; 31.29 mg/ml of L-Cystine-2HCL; 7.35 mg/ml of L-Glutamic Acid; 365.0 mg/ml of L-Glutamine; 18.75 mg/ml of Glycine; 52.48 mg/ml of L-Histidine-HCL—$H_2O$; 106.97 mg/ml of L-Isoleucine; 111.45 mg/ml of L-Leucine; 163.75 mg/ml of L-Lysine HCL; 32.34 mg/ml of L-Methionine; 68.48 mg/ml of L-Phenylalainine; 40.0 mg/ml of L-Proline; 26.25 mg/ml of L-Serine; 101.05 mg/ml of L-Threonine; 19.22 mg/ml of L-Tryptophan; 91.79 mg/ml of L-Tryrosine-2Na—$2H_2O$; and 99.65 mg/ml of L-Valine; 0.0035 mg/L of Biotin; 3.24 mg/L of D-Ca Pantothenate; 11.78 mg/L of Choline Chloride; 4.65 mg/L of Folic Acid; 15.60 mg/L of i-Inositol; 3.02 mg/L of Niacinamide; 3.00 mg/L of Pyridoxal HCL; 0.031 mg/L of Pyridoxine HCL; 0.319 mg/L of Riboflavin; 3.17 mg/L of Thiamine HCL; 0.365 mg/L of Thymidine; 0.680 mg/L of Vitamin $B_{12}$; 25 mM of HEPES Buffer; 2.39 mg/L of Na Hypoxanthine; 0.105 mg/L of Lipoic Acid; 0.081 mg/L of Sodium Putrescine-2HCL; 55.0 mg/L of Sodium Pyruvate; 0.0067 mg/L of Sodium Selenite; 20 uM of Ethanolamine; 0.122 mg/L of Ferric Citrate; 41.70 mg/L of Methyl-B-Cyclodextrin complexed with Linoleic Acid; 33.33 mg/L of Methyl-B-Cyclodextrin complexed with Oleic Acid; 10 mg/L of Methyl-B-Cyclodextrin complexed with Retinal Acctate. Adjust osmolarity to 327 mOsm) with 2 mm glutamine and 1×penstrep. (BSA (81-068-3 Bayer) 100 gm dissolved in ~1L DMEM for a 10% BSA stock solution). Filter the media and collect 50 ul for endotoxin assay in 15 ml polystyrene conical.

The transfection reaction is terminated, preferably by tag-teaming, at the end of the incubation period. Person A aspirates off the transfection media, while person B adds 1.5 ml appropriate media to each well. Incubate at 37° C. for 45 or 72 hours depending on the media used: 1%BSA for 45 hours or CHO-5 for 72 hours.

On day four, using a 300 ul multichannel pipetter, aliquot 600 ul in one 1 ml deep well plate and the remaining supernatant into a 2 ml deep well. The supernatants from each well can then be used in the assays described in Examples 14–21.

It is specifically understood that when activity is obtained in any of the assays described below using a supernatant, the activity originates from either the IL-20 polypeptide directly (e.g., as a secreted protein) or by IL-20 inducing expression of other proteins, which are then secreted into the supernatant. Thus, the invention further provides a method of identifying the protein in the supernatant characterized by an activity in a particular assay.

Example 13

Construction of GAS Reporter Construct

One signal transduction pathway involved in the differentiation and proliferation of cells is called the Jaks-STATs pathway. Activated proteins in the Jaks-STATs pathway bind to gamma activation site "GAS" elements or interferon-sensitive responsive element ("ISRE"), located in the promoter of many genes. The binding of a protein to these elements alter the expression of the associated gene.

GAS and ISRE elements are recognized by a class of transcription factors called Signal Transducers and Activators of Transcription, or "STATs." There are six members of the STATs family. Stat1 and Stat3 are present in many cell types, as is Stat2 (as response to IFN-alpha is widespread). Stat4 is more restricted and is not in many cell types though it has been found in T helper class I, cells after treatment with IL-12. Stat5 was originally called mammary growth factor, but has been found at higher concentrations in other cells including myeloid cells. It can be activated in tissue culture cells by many cytokines.

The STATs are activated to translocate from the cytoplasm to the nucleus upon tyrosine phosphorylation by a set of kinases known as the Janus Kinase ("Jaks") family. Jaks represent a distinct family of soluble tyrosine kinases and include Tyk2, Jak1, Jak2, and Jak3. These kinases display significant sequence similarity and are generally catalytically inactive in resting cells.

The Jaks are activated by a wide range of receptors summarized in Table III below. (Adapted from review by Schidler and Darnell, *Ann. Rev. Biochem.* 64:621–51 (1995).) A cytokine receptor family, capable of activating Jaks, is divided into two groups: (a) Class I includes receptors for IL-2, IL-3, IL-4, IL-6, IL-7, IL-9, IL-11, IL-12, IL-15, Epo, PRL, GH, G-CSF, GM-CSF, LIF, CNTF, and thrombopoietin; and (b) Class 2 includes IFN-a, LFN-g, and IL-10. The Class 1 receptors share a conserved cysteine motif (a set of four conserved cysteines and one tryptophan) and a WSXWS motif (a membrane proxial region encoding Trp-Ser-Xxx-Trp-Ser (SEQ ID NO:17)).

Thus, on binding of a ligand to a receptor, Jaks are activated, which in turn activate STATs, which then translocate and bind to GAS elements. This entire process is encompassed in the Jaks-STATs signal transduction pathway. Therefore, activation of the Jaks-STATs pathway, reflected by the binding of the GAS or the ISRE element, can be used to indicate proteins involved in the proliferation and differentiation of cells. For example, growth factors and cytokines are known to activate the Jaks-STATs pathway. (See Table III below.) Thus, by using GAS elements linked to reporter molecules, activators of the Jaks-STATs pathway can be identified.

TABLE III

| Ligand | JAKs tyk2 | Jak1 | Jak2 | Jak3 | STATS | GAS (elements) or ISRE |
|---|---|---|---|---|---|---|
| IFN family | | | | | | |
| IFN-a/B | + | + | − | − | 1,2,3 | ISRE |
| IFN-g | | + | + | − | 1 | GAS (IRF1 > Lys6 > IFP) |
| Il-10 | + | ? | ? | − | 1,3 | |
| gp130 family | | | | | | |
| IL-6 (Pleiotrohic) | + | + | + | ? | 1,3 | GAS (IRF1 > Lys6 > IFP) |
| Il-11 (Pleiotrohic) | ? | + | ? | ? | 1,3 | |
| OnM (Pleiotrohic) | ? | + | + | ? | 1,3 | |
| LIF (Pleiotrohic) | ? | + | + | ? | 1,3 | |
| CNTF (Pleiotrohic) | −/+ | + | + | ? | 1,3 | |
| G-CSF (Pleiotrohic) | ? | + | ? | ? | 1,3 | |
| IL-12 (Pleiotrohic) | + | − | + | + | 1,3 | |
| g-C family | | | | | | |
| IL-2 (lymphocytes) | − | + | − | + | 1,3,5 | GAS |
| IL-4 (lymph/myeloid) | − | + | − | + | 6 | GAS (IRF1 = IFP >> Ly6) (IgH) |
| IL-7 (lymphocytes) | − | + | − | + | 5 | GAS |
| IL-9 (lymphocytes) | − | + | − | + | 5 | GAS |
| IL-13 (lymphocyte) | − | + | ? | ? | 6 | GAS |
| IL-15 | ? | + | ? | + | 5 | GAS |
| gp140 family | | | | | | |
| IL-3 (myeloid) | − | − | + | − | 5 | GAS (IRF1 > IFP >> Ly6) |
| IL-5 (myeloid) | − | − | + | − | 5 | GAS |
| GM-CSF (myeloid) | − | − | + | − | 5 | GAS |
| Growth hormone family | | | | | | |
| GH | ? | − | + | − | 5 | |
| PRL | ? | +/− | + | − | 1,3,5 | |
| EPO | ? | − | + | − | 5 | GAS (B-CAS > IRF1 = IFP >> Ly6) |
| Receptor Tyrosine Kinases | | | | | | |
| EGF | ? | + | + | − | 1,3 | GAS (IRF1) |
| PDGF | ? | + | + | − | 1,3 | |
| CSF-1 | ? | + | + | − | 1,3 | GAS (not IRF1) |

To construct a synthetic GAS containing promoter element, which is used in the Biological Assays described in Examples 14–15, a PCR based strategy is employed to generate a GAS-SV40 promoter sequence. The 5' primer contains four tandem copies of the GAS binding site found in the IRF1 promoter and previously demonstrated to bind STATs upon induction with a range of cytokines (Rothman et al., *Immunity* 1:457–468 (1994).), although other GAS or ISRE elements can be used instead. The 5' primer also contains 18 bp of sequence complementary to the SV40 early promoter sequence and is flanked with an Xho I site. The sequence of the 5' primer is: 5'-GCG CCT CGA GAT TTC CCC GAA ATC TAG ATT TCC CCG AAA TGA TTT CCC CGA AAT GAT TTC CCC GAA ATA TCT GCC ATC TCA ATT AG-3' (SEQ ID NO:18). The downstream primer is complementary to the SV40 promoter and is flanked with a Hin dIII site: 5'-GCG GCA AGC TTT TTG CAA AGC CTA GGC-3' (SEQ ID NO:19).

PCR amplification is performed using the SV40 promoter template present in the β-gal:promoter plasmid obtained from Clontech. The resulting PCR fragment is digested with Xho I and Hin dIII and subcloned into BLSK2-. (Stratagene.) Sequencing with forward and reverse primers confirms that the insert contains the following sequence: 5'-CTC GAG ATT TCC CCG AAA TCT AGA TTT CCC CGA AAT GAT TTC CCC GAA ATG ATT TCC CCG AAA TAT CTG CCA TCT CAA TTA GTC AGC AAC CAT AGT CCC GCC CCT AAC TCC GCC CAT CCC GCC CCT AAC TCC GCC CAG TTC CGC CCA TTC TCC GCC CCA TGG CTG ACT AAT TTT TTT TAT TTA TGC AGA GGC CGA GGC CGC CTC GGC CTC TGA GCT ATT CCA GAA GTA GTG AGG AGG CTT TTT TGG AGG CCT AGG CTT TTG CAA AAA GCT T-3' (SEQ ID NO:20).

With this GAS promoter element linked to the SV40 promoter, a GAS:SEAP2 reporter construct is next engineered. Here, the reporter molecule is a secreted alkaline phosphatase, or "SEAP." Clearly, however, any reporter molecule can be instead of SEAP, in this or in any of the other Examples. Well known reporter molecules that can be used instead of SEAP include chloramphenicol acetyltransferase (CAT), luciferase, alkaline phosphatase, B-galactosidase, green fluorescent protein (GFP), or any protein detectable by an antibody.

The above sequence confirmed synthetic GAS-SV40 promoter element is subcloned into the pSEAP-Promoter vector obtained from Clontech using Hin dII and Xho I, effectively replacing the SV40 promoter with the amplified GAS:SV40 promoter element, to create the GAS-SEAP vector. However, this vector does not contain a neomycin resistance gene, and therefore, is not preferred for mammalian expression systems. Thus, in order to generate mammalian stable cell lines expressing the GAS-SEAP reporter, the GAS-SEAP cassette is removed from the GAS-SEAP vector using Sal I and Not I, and inserted into a backbone vector containing the neomycin resistance gene, such as pGFP-1 (Clontech), using these restriction sites in the multiple cloning site, to create the GAS-SEAP/Neo vector. Once this vector is transfected into mammalian cells, this vector can then be used as a reporter molecule for GAS binding as described in Examples 14–15.

Other constructs can be made using the above description and replacing GAS with a different promoter sequence. For example, construction of reporter molecules containing NF-κB and EGR promoter sequences are described in Examples 16 and 17. However, many other promoters can be substituted using the protocols described in these Examples. For instance, SRE, IL-2, NFAT, or Osteocalcin promoters can be substituted, alone or in combination (e.g., GAS/NF-κB/EGR, GAS/NF-κB, Il-2/NFAT, or NF-κB/GAS). Similarly, other cell lines can be used to test reporter construct activity, such as HELA (epithelial), HUVEC (endothelial), Reh (B-cell), Saos-2 (osteoblast), HUVAC (aortic), or Cardiomyocyte.

Example 14

High-throughput Screening Assay for T-cell Activity

The following protocol is used to assess T-cell activity of IL-20 by determining whether IL-20 supernatant proliferates and/or differentiates T-cells. T-cell activity is assessed using the GAS/SEAP/Neo construct produced in Example 13. Thus, factors that increase SEAP activity indicate the ability to activate the Jaks-STATS signal transduction pathway. The T-cell used in this assay is Jurkat T-cells (ATCC Accession No. TIB-152), although Molt-3 cells (ATCC Accession No. CRL-1552) and Molt-4 cells (ATCC Accession No. CRL-1582) cells can also be used.

Jurkat T-cells are lymphoblastic CD4+ Th1 helper cells. In order to generate stable cell lines, approximately 2 million Jurkat cells are transfected with the GAS-SEAP/neo vector using DMRIE-C (Life Technologies)(transfection procedure described below). The transfected cells are seeded to a density of approximately 20,000 cells per well and transfectants resistant to 1 mg/ml genticin selected. Resistant colonies are expanded and then tested for their response to increasing concentrations of interferon gamma. The dose response of a selected clone is demonstrated.

Specifically, the following protocol will yield sufficient cells for 75 wells containing 200 ul of cells. Thus, it is either scaled up, or performed in multiple to generate sufficient cells for multiple 96 well plates. Jurkat cells are maintained in RPMI+10% serum with 1%Pen-Strep. Combine 2.5 mls of OPTI-MEM (Life Technologies) with 10 ug of plasmid DNA in a T25 flask. Add 2.5 ml OPTI-MEM containing 50 ul of DMRIE-C and incubate at room temperature for 15–45 mins. During the incubation period, count cell concentration, spin down the required number of cells ($10^7$ per transfection), and resuspend in OPTI-MEM to a final concentration of $10^7$ cells/ml. Then add 1 ml of $1\times10^7$ cells in OPTI-MEM to T25 flask and incubate at 37° C. for 6 hrs. After the incubation, add 10 ml of RPMI+15% serum.

The Jurkat:GAS-SEAP stable reporter lines are maintained in RPMI+10% serum, 1 mg/ml Genticin, and 1% Pen-Strep. These cells are treated with supernatants containing IL-20 polypeptides or IL-20 induced polypeptides as produced by the protocol described in Example 12.

On the day of treatment with the supernatant, the cells should be washed and resuspended in fresh RPMI+10% serum to a density of 500,000 cells per ml. The exact number of cells required will depend on the number of supernatants being screened. For one 96 well plate, approximately 10 million cells (for 10 plates, 100 million cells) are required.

Transfer the cells to a triangular reservoir boat, in order to dispense the cells into a 96 well dish, using a 12 channel pipette. Using a 12 channel pipette, transfer 200 ul of cells into each well (therefore adding 100,000 cells per well). After all the plates have been seeded, 50 ul of the supernatants are transferred directly from the 96 well plate containing the supernatants into each well using a 12 channel pipette. In addition, a dose of exogenous interferon gamma (0.1, 1.0, 10 ng) is added to wells H9, H10, and H11 to serve as additional positive controls for the assay. The 96 well dishes containing Jurkat cells treated with supernatants are placed in an incubator for 48 hrs (note: this time is variable between 48–72 hrs). 35 ul samples from each well are then transferred to an opaque 96 well plate using a 12 channel pipette. The opaque plates should be covered (using sellophene covers) and stored at −20° C. until SEAP assays are performed according to Example 18. The plates containing the remaining treated cells are placed at 4° C. and serve as a source of material for repeating the assay on a specific well if desired. As a positive control, 100 Unit/ml interferon gamma can be used which is known to activate Jurkat T cells. Over 30 fold induction is typically observed in the positive control wells.

Example 15

High-throughput Screening Assay Identifying Myeloid Activity

The following protocol is used to assess myeloid activity of IL-20 by determining whether IL-20 proliferates and/or differentiates myeloid cells. Myeloid cell activity is assessed using the GAS/SEAP/Neo construct produced in Example 13. Thus, factors that increase SEAP activity indicate the ability to activate the Jaks-STATS signal transduction pathway. The myeloid cell used in this assay is U937, a pre-monocyte cell line, although TF-1, HL60, or KG1 can be used.

To transiently transfect U937 cells with the GAS/SEAP/Neo construct produced in Example 13, a DEAE-Dextran method (Kharbanda et. al., 1994, Cell Growth & Differentiation, 5:259–265) is used. First, harvest $2\times10^7$ U937 cells and wash with PBS. The U937 cells are usually grown in RPMI 1640 medium containing 10% heat-inactivated fetal bovine serum (FEBS) supplemented with 100 units/ml penicillin and 100 mg/ml streptomycin. Next, suspend the cells in 1 ml of 20 mM Tris-HCl (pH 7.4) buffer containing 0.5 mg/ml DEAE-Dextran, 8 ug GAS-SEAP2 plasmid DNA, 140 mM NaCl, 5 mM KCl, 375 uM $Na_2HPO_4.7H_2O$, 1 mM $MgCl_2$, and 675 uM $CaCl_2$. Incubate at 37° C. for 45 min. Wash the cells with RPMI 1640 medium containing 10% FBS and then resuspend in 10 ml complete medium and incubate at 37° C. for 36 hr.

The GAS-SEAP/U937 stable cells are obtained by growing the cells in 400 ug/ml G418. The G418-free medium is used for routine growth but every one to two months, the cells should be re-grown in 400 ug/ml G418 for couple of passages. These cells are tested by harvesting $1\times10^8$ cells (this is enough for ten 96-well plates assay) and wash with PBS. Suspend the cells in 200 ml above described growth medium, with a final density of $5\times10^5$ cells/ml. Plate 200 ul cells per well in the 96-well plate (or $1\times10^5$ cells/well). Add 50 ul of the supernatant prepared by the protocol described in Example 12. Incubate at 37° C. for 48 to 72 hr. As a positive control, 100 Unit/ml interferon gamma can be used which is known to activate U937 cells. Over 30 fold induction is typically observed in the positive control wells. SEAP assay the supernatant according to the protocol described in Example 18.

Example 16

High-throughput Screening Assay Identifying Neuronal Activity

When cells undergo differentiation and proliferation, a group of genes are activated through many different signal transduction pathways. One of these genes, EGR1 (early growth response gene 1), is induced in various tissues and cell types upon activation. The promoter of EGR1 is responsible for such induction. Using the EGR1 promoter linked to reporter molecules, activation of cells can be assessed by IL-20.

Particularly, the following protocol is used to assess neuronal activity in PC12 cell lines. PC12 cells (rat phenochromocytoma cells) are known to proliferate and/or differentiate by activation with a number of mitogens, such as TPA (tetradecanoyl phorbol acetate), NGF (nerve growth factor), and EGF (epidermal growth factor). The EGR1 gene expression is activated during this treatment. Thus, by stably transfecting PC12 cells with a construct containing an EGR promoter linked to SEAP reporter, activation of PC12 cells by IL-20 can be assessed.

The EGR/SEAP reporter construct can be assembled by the following protocol. The EGR-1 promoter sequence (−633 to +1) (Sakamoto K et al., Oncogene 6:867–871 (1991)) can be PCR amplified from human genomic DNA using the following primers: 5' primer: 5'-GCG CTC GAG GGA TGA CAG CGA TAG AAC CCC GG-3' (SEQ ID NO:21) and 3' primer: 5'-GCG AAG CTT CGC GAC TCC CCG GAT CCG CCT C-3' (SEQ ID NO:22).

Using the GAS:SEAP/Neo vector produced in Example 13, EGR1 amplified product can then be inserted into this vector. Linearize the GAS:SEAP/Neo vector using restriction enzymes Xho I and Hin dIII, removing the GAS/SV40 stuffer. Restrict the EGR1 amplified product with these same enzymes. Ligate the vector and the EGR1 promoter.

To prepare 96 well-plates for cell culture, two mls of a coating solution (1:30 dilution of collagen type I (Upstate Biotech Inc. Cat#08-115) in 30% ethanol (filter sterilized)) is added per one 10 cm plate or 50 ml per well of the 96-well plate, and allowed to air dry for 2 hr. PC12 cells are routinely grown in RPMI-1640 medium (Bio Whittaker) containing 10% horse serum (JRH BIOSCIENCES, Cat. # 12449-78P), 5% heat-inactivated fetal bovine serum (FBS) supplemented with 100 units/ml penicillin and 100 ug/ml streptomycin on a precoated 10 cm tissue culture dish. One to four split is done every three to four days. Cells are removed from the plates by scraping and resuspended with pipetting up and down for more than 15 times. Transfect the EGR/SEAP/Neo construct into PC12 using the Lipofectamnine protocol described in Example 12. EGR-SEAP/PC12 stable cells are obtained by growing the cells in 300 ug/ml G418. The G418-free medium is used for routine growth but every one to two months, the cells should be re-grown in 300 ug/ml G418 for couple of passages.

To assay for neuronal activity, a 10 cm plate with cells around 70 to 80% confluent is screened by removing the old medium. Wash the cells once with PBS (Phosphate buffered saline). Then starve the cells in low serum medium (RPMI-1640 containing 1% horse serum and 0.5% FBS with antibiotics) overnight. The next morning, remove the medium and wash the cells with PBS. Scrape off the cells from the plate, suspend the cells well in 2 ml low serum medium. Count the cell number and add more low serum medium to reach final cell density as $5\times10^5$ cells/ml.

Add 200 ul of the cell suspension to each well of 96-well plate (equivalent to $1\times10^5$ cells/well). Add 50 ul supernatant produced by Example 12, 37° C. for 48 to 72 hr. As a positive control, a growth factor known to activate PC12 cells through EGR can be used, such as 50 ng/ul of Neuronal Growth Factor (NGF). Over fifty-fold induction of SEAP is typically seen in the positive control wells. SEAP assay the supernatant according to Example 18.

Example 17

High-throughput Screening Assay for T-cell Activity

NF-κB (Nuclear Factor-κB) is a transcription factor activated by a wide variety of agents including the inflammatory cytokines IL-1 and TNF, CD30 and CD40, lymphotoxin-alpha and lymphotoxin-beta, by exposure to LPS or thrombin, and by expression of certain viral gene products. As a transcription factor, NF-κB regulates the expression of genes involved in immune cell activation, control of apoptosis (NF-κB appears to shield cells from apoptosis), B- and T-cell development, anti-viral and antimicrobial responses, and multiple stress responses.

In non-stimulated conditions, NF-κB is retained in the cytoplasm with I-KB (Inhibitor κB). However, upon stimulation, I-κB is phosphorylated and degraded, causing NF-κB to shuttle to the nucleus, thereby activating transcription of target genes. Target genes activated by NF-κB include IL-2, IL-6, GM-CSF, ICAM-1 and class 1 MHC.

Due to its central role and ability to respond to a range of stimuli, reporter constructs utilizing the NF-κB promoter element are used to screen the supernatants produced in Example 12. Activators or inhibitors of NF-κB are useful in treating diseases. For example, inhibitors of NF-κB could be used to treat those diseases related to the acute or chronic activation of NF-κB, such as rheumatoid arthritis.

To construct a vector containing the NF-κB promoter element, a PCR based strategy is employed. The upstream primer contains four tandem copies of the NF-κB binding site (GGG GAC TTT CCC) (SEQ ID NO:23), 18 bp of sequence complementary to the 5' end of the SV40 early promoter sequence, and is flanked with an Xho I site: 5'-GCG GCC TCG AGG GGA CTT TCC CGG GGA CTT TCC GGG GAC TTT CCG GGA CTT TCC ATC CTG CCA TCT CAA TTA G-3' (SEQ ID NO:24). The downstream primer is complementary to the 3' end of the SV40 promoter and is flanked with a Hin dIII site: 5'-GCG GCA AGC TTT TTG CAA AGC CTA GGC-3' (SEQ ID NO:25).

PCR amplification is performed using the SV40 promoter template present in the gal:promoter plasmid obtained from Clontech. The resulting PCR fragment is digested with Xho I and Hin dIII and subcloned into BLSK2-. (Stratagene) Sequencing with the T7 and T3 primers confirms the insert contains the following sequence: 5'-CTC GAG GGG ACT TTC CCG GGG ACT TTC CGG GGA CTT TCC GGG ACT TTC CAT CTG CCA TCT CAA TTA GTC AGC AAC CAT AGT CCC GCC CCT AAC TCC GCC CAT CCC GCC CCT AAC TCC GCC CAG TTC CGC CCA TTC TCC GCC CCA TGG CTG ACT AAT TTT TTT TAT TTA TGC AGA GGC CGA GGC CGC CTC GGC CTC TGA GCT ATT CCA GAA GTA GTG AGG AGG CTT TTT TGG AGG CCT AGG CTT TTG CAA AAA GCT T-3' (SEQ ID NO:26).

Next, replace the SV40 minimal promoter element present in the pSEAP2-promoter plasmid (Clontech) with this NF-κB/SV40 fragment using Xho I and Hin dIII. However, this vector does not contain a neomycin resistance gene, and therefore, is not preferred for mammalian expression systems. In order to generate stable mammalian cell lines, the NF-κB/SV40/SEAP cassette is removed from the above NF-κB/SEAP vector using restriction enzymes Sal I and Not I, and inserted into a vector containing neomycin resistance. Particularly, the NF-κB/SV40/SEAP cassette was inserted into pGFP-1 (Clontech), replacing the GFP gene, after restricting pGFP-1 with Sal I and Not I.

Once NF-κB/SV40/SEAP/Neo vector is created, stable Jurkat T-cells are created and maintained according to the protocol described in Example 14. Similarly, the method for assaying supernatants with these stable Jurkat T-cells is also described in Example 14. As a positive control, exogenous TNF alpha (0.1, 1, 10 ng) is added to wells H9, H10, and H11, with a 5–10 fold activation typically observed.

Example 18

Assay for SEAP Activity

As a reporter molecule for the assays described in Examples 14–17, SEAP activity is assayed using the Tropix Phospho-light Kit (Cat. BP-400) according to the following general procedure. The Tropix Phospho-light Kit supplies the Dilution, Assay, and Reaction Buffers used below.

Prime a dispenser with the 2.5×Dilution Buffer and dispense 15 ul of 2.5×dilution buffer into Optiplates containing 35 ul of a supernatant. Seal the plates with a plastic sealer and incubate at 65° C. for 30 min. Separate the Optiplates to avoid uneven heating. Cool the samples to room temperature for 15 minutes. Empty the dispenser and prime with the Assay Buffer. Add 50 ml Assay Buffer and incubate at room temperature 5 min. Empty the dispenser and prime with the Reaction Buffer (see Table IV below). Add 50 ul Reaction Buffer and incubate at room temperature for 20 minutes. Since the intensity of the chemiluminescent signal is time dependent, and it takes about 10 minutes to read 5 plates on luminometer, one should treat 5 plates at each time and start the second set 10 minutes later. Read the relative light unit in the luminometer. Set H12 as blank, and print the results. An increase in chemiluminescence indicates reporter activity.

TABLE IV

Reaction Buffer Formulation:

| # of plates | Rxn buffer diluent (ml) | CSPD (ml) |
|---|---|---|
| 10 | 60 | 3 |
| 11 | 65 | 3.25 |
| 12 | 70 | 3.5 |
| 13 | 75 | 3.75 |
| 14 | 80 | 4 |
| 15 | 85 | 4.25 |
| 16 | 90 | 4.5 |
| 17 | 95 | 4.75 |
| 18 | 100 | 5 |
| 19 | 105 | 5.25 |
| 20 | 110 | 5.5 |
| 21 | 115 | 5.75 |
| 22 | 120 | 6 |
| 23 | 125 | 6.25 |
| 24 | 130 | 6.5 |
| 25 | 135 | 6.75 |
| 26 | 140 | 7 |
| 27 | 145 | 7.25 |
| 28 | 150 | 7.5 |
| 29 | 155 | 7.75 |
| 30 | 160 | 8 |
| 31 | 165 | 8.25 |
| 32 | 170 | 8.5 |
| 33 | 175 | 8.75 |
| 34 | 180 | 9 |
| 35 | 185 | 9.25 |
| 36 | 190 | 9.5 |
| 37 | 195 | 9.75 |
| 38 | 200 | 10 |
| 39 | 205 | 10.25 |
| 40 | 210 | 10.5 |
| 41 | 215 | 10.75 |

TABLE IV-continued

Reaction Buffer Formulation:

| # of plates | Rxn buffer diluent (ml) | CSPD (ml) |
|---|---|---|
| 42 | 220 | 11 |
| 43 | 225 | 11.25 |
| 44 | 230 | 11.5 |
| 45 | 235 | 11.75 |
| 46 | 240 | 12 |
| 47 | 245 | 12.25 |
| 48 | 250 | 12.5 |
| 49 | 255 | 12.75 |
| 50 | 260 | 13 |

Example 19

High-throughput Screening Assay Identifying Changes in Small Molecule Concentration and Membrane Permeability Binding of a ligand to a receptor is known to alter intracellular levels of small molecules, such as calcium, potassium, sodium, and pH, as well as alter membrane potential. These alterations can be measured in an assay to identify supernatants which bind to receptors of a particular cell. Although the following protocol describes an assay for calcium, this protocol can easily be modified to detect changes in potassium, sodium, pH, membrane potential, or any other small molecule which is detectable by a fluorescent probe.

The following assay uses Fluorometric Imaging Plate Reader ("FLIPR") to measure changes in fluorescent molecules (Molecular Probes) that bind small molecules. Clearly, any fluorscent molecule detecting a small molecule can be used instead of the calcium fluorescent molecule, fluo-3, used here.

For adherent cells, seed the cells at 10,000–20,000 cells/well in a Co-star black 96-well plate with clear bottom. The plate is incubated in a $CO_2$ incubator for 20 hours. The adherent cells are washed two times in Biotek washer with 200 ul of HBSS (Hank's Balanced Salt Solution) leaving 100 ul of buffer after the final wash. A stock solution of 1 mg/ml fluo-3 is added in 10% pluronic acid DMSO. To load the cells with fluo-3, 50 ul of 12 ug/ml fluo-3 is added to each well. The plate is incubated at 37° C. in a $CO_2$ incubator for 60 min. The plate is washed four times in the Biotek washer with HBSS leaving 100 ul of buffer.

For non-adherent cells, the cells are spun down from culture media. Cells are re-suspended to 2–5×$10^6$ cells/ml with HBSS in a 50-ml conical tube. 4 ul of 1 mg/ml fluo-3 solution in 10% pluronic acid DMSO is added to each ml of cell suspension. The tube is then in a 37° C. water bath for 30–60 min. The cells are washed twice with HBSS, resuspended to 1×$10^6$ cells/ml, and dispensed into a microplate, 100 ul/well. The plate is centrifuged at 1000 rpm for 5 min. The plate is then washed once in Denley CellWash with 200 ul, followed by an aspiration step to 100 ul final volume.

For a non-cell based assay, each well contains a fluorescent molecule, such as fluo-3. The supernatant is added to the well, and a change in fluorescence is detected.

To measure the fluorescence of intracellular calcium, the FLIPR is set for the following parameters: (1) System gain is 300–800 mW; (2) Exposure time is 0.4 second; (3) Camera F/stop is F/2; (4) Excitation is 488 nm; (5) Emission is 530 nm; and (6) Sample addition is 50 ul. Increased emission at 530 nm indicates an extracellular signaling event caused by the a molecule, either IL-20 or a molecule induced by IL-20, which has resulted in an increase in the intracellular $Ca^{2+}$ concentration.

Example 20

High-throughput Screening Assay Identifying Tyrosine Kinase Activity

The Protein Tyrosine Kinases (PTK) represent a diverse group of transmembrane and cytoplasmic kinases. Within the Receptor Protein Tyrosine Kinase RPTK) group are receptors for a range of mitogenic and metabolic growth factors including the PDGF, FGF, EGF, NGF, HGF and Insulin receptor subfamilies. In addition there are a large family of RPTKs for which the corresponding ligand is unknown. Ligands for RPTKs include mainly secreted small proteins, but also membrane-bound and extracellular matrix proteins.

Activation of RPTK by ligands involves ligand-mediated receptor dimerization, resulting in transphosphorylation of the receptor subunits and activation of the cytoplasmic tyrosine kinases. The cytoplasmic tyrosine kinases include receptor associated tyrosine kinases of the src-family (e.g., src, yes, lck, lyn, fyn) and non-receptor linked and cytosolic protein tyrosine kinases, such as the Jak family, members of which mediate signal transduction triggered by the cytokine superfamily of receptors (e.g., the Interleukins, Interferons, GM-CSF, and Leptin).

Because of the wide range of known factors capable of stimulating tyrosine kinase activity, identifying whether IL-20 or a molecule induced by IL-20 is capable of activating tyrosine kinase signal transduction pathways is of interest. Therefore, the following protocol is designed to identify such molecules capable of activating the tyrosine kinase signal transduction pathways.

Seed target cells (e.g., primary keratinocytes) at a density of approximately 25,000 cells per well in a 96 well Loprodyne Silent Screen Plates purchased from Nalge Nunc (Naperville, Ill.). The plates are sterilized with two 30 minute rinses with 100% ethanol, rinsed with water and dried overnight. Some plates are coated for 2 hr with 100 ml of cell culture grade type I collagen (50 mg/ml), gelatin (2%) or polylysine (50 mg/ml), all of which can be purchased from Sigma Chemicals (St. Louis, Mo.) or 10% Matrigel purchased from Becton Dickinson (Bedford, Mass.), or calf serum, rinsed with PBS and stored at 4° C. Cell growth on these plates is assayed by seeding 5,000 cells/well in growth medium and indirect quantitation of cell number through use of alamarBlue as described by the manufacturer Alamar Biosciences, Inc. (Sacramento, Calif.) after 48 hr. Falcon plate covers #3071 from Becton Dickinson (Bedford, Mass.) are used to cover the Loprodyne Silent Screen Plates. Falcon Microtest III cell culture plates can also be used in some proliferation experiments.

To prepare extracts, A431 cells are seeded onto the nylon membranes of Loprodyne plates (20,000/200 ml/well) and cultured overnight in complete medium. Cells are quiesced by incubation in serum-free basal medium for 24 hr. After 5–20 minutes treatment with EGF (60 ng/ml) or 50 ul of the supernatant produced in Example 12, the medium was removed and 100 ml of extraction buffer ((20 mM HEPES pH 7.5, 0.15 M NaCl, 1% Triton X-100, 0.1% SDS, 2 mM Na3VO4, 2 mM Na4P2O7 and a cocktail of protease inhibitors (# 1836170) obtained from Boeheringer Mannheim (Indianapolis, Ind.) is added to each well and the plate is shaken on a rotating shaker for 5 minutes at 4° C. The plate is then placed in a vacuum transfer manifold and the extract filtered through the 0.45 mm membrane bottoms of each well using house vacuum. Extracts are collected in a 96-well catch/assay plate in the bottom of the vacuum manifold and immediately placed on ice. To obtain extracts clarified by centrifugation, the content of each well, after detergent solubilization for 5 minutes, is removed and centrifuged for 15 min at 4° C. at 16,000×g.

Test the filtered extracts for levels of tyrosine kinase activity. Although many methods of detecting tyrosine kinase activity are known, one method is described here. Generally, the tyrosine kinase activity of a supernatant is evaluated by determining its ability to phosphorylate a tyrosine residue on a specific substrate (a biotinylated peptide). Biotinylated peptides that can be used for this purpose include PSKI (corresponding to amino acids 6–20 of the cell division kinase cdc2-p34) and PSK2 (corresponding to amino acids 1–17 of gastrin). Both peptides are substrates for a range of tyrosine kinases and are available from Boehringer Mannheim.

The tyrosine kinase reaction is set up by adding the following components in order. First, add 10 ul of 5 uM Biotinylated Peptide, then 10 ul ATP/$Mg_{2+}$ (5 mM ATP/50 mM $MgCl_2$), then 10 ul of 5×Assay Buffer (40 mM imidazole hydrochloride, pH7.3, 40 mM beta-glycerophosphate, 1 mM EGTA, 100 mM $MgCl_2$, 5 mM $MnCl_2$ 0.5 mg/ml BSA), then 5 ul of Sodium Vanadate(1 mM), and then 5 ul of water. Mix the components gently and preincubate the reaction mix at 30° C. for 2 min. Initial the reaction by adding 10 ul of the control enzyme or the filtered supernatant. The tyrosine kinase assay reaction is then terminated by adding 10 ul of 120 mm EDTA and place the reactions on ice.

Tyrosine kinase activity is determined by transferring 50 ul aliquot of reaction mixture to a microtiter plate (MTP) module and incubating at 37° C. for 20 min. This allows the streptavadin coated 96 well plate to associate with the biotinylated peptide. Wash the MTP module with 300 ul/well of PBS four times. Next add 75 ul of anti-phospotyrosine antibody conjugated to horse radish peroxidase(anti-P-Tyr-POD(0.5 u/ml)) to each well and incubate at 37° C. for one hour. Wash the well as above.

Next add 100 ul of peroxidase substrate solution (Boehringer Mannheim) and incubate at room temperature for at least 5 mins (up to 30 min). Measure the absorbance of the sample at 405 nm by using ELISA reader. The level of bound peroxidase activity is quantitated using an ELISA reader and reflects the level of tyrosine kinase activity.

Example 21

High-throughput Screening Assay Identifying Phosphorylation Activity

As a potential alternative and/or compliment to the assay of protein tyrosine kinase activity described in Example 20, an assay which detects activation (phosphorylation) of major intracellular signal transduction intermediates can also be used. For example, as described below one particular assay can detect tyrosine phosphorylation of the Erk-1 and Erk-2 kinases. However, phosphorylation of other molecules, such as Raf, JNK, p38 MAP, Map kinase kinase (MEK), MEK kinase, Src, Muscle specific kinase (MuSK), IRAK, Tec, and Janus, as well as any other phosphoserine, phosphotyrosine, or phosphothreonine molecule, can be detected by substituting these molecules for Erk-1 or Erk-2 in the following assay.

Specifically, assay plates are made by coating the wells of a 96-well ELISA plate with 0.1 ml of protein G (1 ug/ml) for 2 hr at room temp, (RT). The plates are then rinsed with PBS and blocked with 3% BSA/PBS for 1 hr at RT. The protein G plates are then treated with 2 commercial monoclonal antibodies (100 ng/well) against Erk-1 and Erk-2 (1 hr at RT) (Santa Cruz Biotechnology). (To detect other molecules, this step can easily be modified by substituting a monoclonal antibody detecting any of the above described molecules.) After 3–5 rinses with PBS, the plates are stored at 4° C. until use.

A431 cells are seeded at 20,000/well in a 96-well Loprodyne filterplate and cultured overnight in growth medium. The cells are then starved for 48 hr in basal medium (DMEM) and then treated with EGF (6 ng/well) or 50 ul of the supernatants obtained in Example 12 for 5–20 minutes. The cells are then solubilized and extracts filtered directly into the assay plate. After incubation with the extract for 1 hr at RT, the wells are again rinsed. As a positive control, a commercial preparation of MAP kinase (10 ng/well) is used in place of A431 extract. Plates are then treated with a commercial polyclonal (rabbit) antibody (1 ug/ml) which specifically recognizes the phosphorylated epitope of the Erk-1 and Erk-2 kinases (1 hr at RT). This antibody is biotinylated by standard procedures. The bound polyclonal antibody is then quantitated by successive incubations with Europium-streptavidin and Europium fluorescence enhancing reagent in the Wallac DELFIA instrument (time-resolved fluorescence). An increased fluorescent signal over background indicates a phosphorylation by IL-20 or a molecule induced by IL-20.

Example 22

Method of Determining Alterations in the IL-20 Gene

RNA isolated from entire families or individual patients presenting with a phenotype of interest (such as a disease) is be isolated. cDNA is then generated from these RNA samples using protocols known in the art. (See, Sambrook.) The cDNA is then used as a template for PCR, employing primers surrounding regions of interest in SEQ ID NO:1. Suggested PCR conditions consist of 35 cycles at 95° C. for 30 seconds; 60–120 seconds at 52–58° C.; and 60–120 seconds at 70° C., using buffer solutions described in Sidransky, D., et al., Science 252:706 (1991).

PCR products are then sequenced using primers labeled at their 5' end with T4 polynucleotide kinase, employing SequiTherm Polymerase. (Epicentre Technologies). The intron-exon borders of selected exons of IL-20 are also determined and genomic PCR products analyzed to confirm the results. PCR products harboring suspected mutations in IL-20 are then cloned and sequenced to validate the results of the direct sequencing. PCR products of IL-20 are cloned into T-tailed vectors as described in Holton, T. A. and Graham, M. W., Nucleic Acids Research, 19:1156 (1991) and sequenced with T7 polymerase (United States Biochemical). Affected individuals are identified by mutations in IL-20 not present in unaffected individuals.

Genomic rearrangements are also observed as a method of determining alterations in the IL-20 gene. Genomic clones isolated according to Example 2 are nick-translated with digoxigenindeoxy-uridine 5'-triphosphate (Boehringer Manheim), and FISH performed as described in Johnson, C. et al., Methods Cell Biol. 35:73–99 (1991). Hybridization with the labeled probe is carried out using a vast excess of human cot-1 DNA for specific hybridization to the IL-20 genomic locus. Chromosomes are counterstained with 4,6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson, Cv. et al., Genet. Anal. Tech. Appl., 8:75 (1991).) Image collection, analysis and chromosomal fractional length measurements are performed using the ISee Graphical Program System. (Inovision Corporation, Durham, N.C.) Chromosome alterations of the genomic region of IL-20 (hybridized by the probe) are identified as insertions, deletions, and translocations. These IL-20 alterations are used as a diagnostic marker for an associated disease.

Example 23

Method of Detecting Abnormal Levels of IL-20 in a Biological Sample

IL-20 polypeptides can be detected in a biological sample, and if an increased or decreased level of IL-20 is detected, this polypeptide is a marker for a particular phenotype. Methods of detection are numerous, and thus, it is understood that one skilled in the art can modify the following assay to fit their particular needs.

For example, antibody-sandwich ELISAs are used to detect IL-20 in a sample, preferably a biological sample. Wells of a microtiter plate are coated with specific antibodies to IL-20, at a final concentration of 0.2 to 10 ug/ml. The antibodies are either monoclonal or polyclonal and are produced by the method described in Example 11. The wells are blocked so that non-specific binding of IL-20 to the well is reduced. The coated wells are then incubated for >2 hours at RT with a sample containing IL-20. Preferably, serial dilutions of the sample should be used to validate results. The plates are then washed three times with deionized or distilled water to remove unbounded IL-20. Next, 50 ul of specific antibody-alkaline phosphatase conjugate, at a concentration of 25–400 ng, is added and incubated for 2 hours at room temperature. The plates are again washed three times with deionized or distilled water to remove unbounded conjugate. Add 75 ul of 4-methylumbelliferyl phosphate (MUP) or p-nitrophenyl phosphate (NPP) substrate solution to each well and incubate 1 hour at room temperature. Measure the reaction by a microtiter plate reader. Prepare a standard curve, using serial dilutions of a control sample, and plot IL-20 polypeptide concentration on the X-axis (log scale) and fluorescence or absorbance of the Y-axis (linear scale). Interpolate the concentration of the IL-20 in the sample using the standard curve.

Example 24

Formulating a Polypeptide

The IL-20 composition will be formulated and dosed in a fashion consistent with good medical practice, taking into account the clinical condition of the individual patient (especially the side effects of treatment with the IL-20 polypeptide alone), the site of delivery, the method of administration, the scheduling of administration, and other factors known to practitioners. The "effective amount" for purposes herein is thus determined by such considerations.

As a general proposition, the total pharmaceutically effective amount of IL-20 administered parenterally per dose will be in the range of about 1 ug/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, IL-20 is typically administered at a dose rate of about 1 ug/kg/hour to about 50 ug/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing IL-20 are administered orally, rectally, parenterally, intracistemally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

IL-20 is also suitably administered by sustained-release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (Sidman, U. et al., Biopolymers 22:547–556 (1983)), poly(2-hydroxyethyl methacrylate) (R. Langer et al., J. Biomed. Mater. Res. 15:167–277 (1981), and R. Langer, Chem. Tech. 12:98–105 (1982)), ethylene vinyl acetate (R. Langer et al.) or poly-D-(−)-3-hydroxybutyric acid (EP 133,988). Sustained-release compositions also include liposomally entrapped IL-20 polypeptides. Liposomes containing the IL-20 are prepared by methods known per se: DE 3,218,121; Epstein et al., Proc. Natl. Acad. Sci. USA 82:3688–3692 (1985); Hwang et al., Proc. Natl. Acad. Sci. USA 77:4030–4034 (1980); EP 52,322; EP 36,676; EP 88,046; EP 143,949; EP 142,641; Japanese Pat. Appl. 83–118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal secreted polypeptide therapy.

For parenteral administration, in one embodiment, IL-20 is formulated generally by mixing it at the desired of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting IL-20 uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

IL-20 is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of polypeptide salts. IL-20 used for therapeutic administration can be sterile. Sterility is readily accomplished by filtration through sterile filtration membranes (e.g., 0.2 micron membranes). Therapeutic polypeptide compositions generally are placed into a container having a sterile access port, for example, an intravenous solution bag or vial having a stopper pierceable by a hypodermic injection needle.

IL-20 polypeptides ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous IL-20 polypeptide solution, and the resulting mixture is lyophilized. The infusion solution is prepared by reconstituting the lyophilized IL-20 polypeptide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, IL-20 may be employed in conjunction with other therapeutic compounds.

Example 25

Method of Treating Decreased Levels of IL-20

The present invention relates to a method for treating an individual in need of a decreased level of IL-20 activity in the body comprising, administering to such an individual a composition comprising a therapeutically effective amount of IL-20 antagonist. Preferred antagonists for use in the present invention are IL-20-specific antibodies.

Moreover, it will be appreciated that conditions caused by a decrease in the standard or normal expression level of IL-20 in an individual can be treated by administering IL-20, preferably in the secreted form. Thus, the invention also provides a method of treatment of an individual in need of an increased level of IL-20 polypeptide comprising administering to such an individual a pharmaceutical composition comprising an amount of IL-20 to increase the activity level of IL-20 in such an individual.

For example, a patient with decreased levels of IL-20 polypeptide receives a daily dose 0.1–100 ug/kg of the polypeptide for six consecutive days. Preferably, the polypeptide is in the secreted form. The exact details of the dosing scheme, based on administration and formulation, are provided in Example 24.

Example 26

Method of Treating Increased Levels of IL-20

The present invention also relates to a method for treating an individual in need of an increased level of IL-20 activity in the body comprising administering to such an individual a composition comprising a therapeutically effective amount of IL-20 or an agonist thereof.

Antisense technology is used to inhibit production of IL-20. This technology is one example of a method of decreasing levels of IL-20 polypeptide, preferably a secreted form, due to a variety of etiologies, such as cancer.

For example, a patient diagnosed with abnormally increased levels of IL-20 is administered intravenously antisense polynucleotides at 0.5, 1.0, 1.5, 2.0 and 3.0 mg/kg day for 21 days. This treatment is repeated after a 7-day rest period if the treatment was well tolerated. The formulation of the antisense polynucleotide is provided in Example 24.

Example 27

Method of Treatment Using Gene Therapy—Ex Vivo

One method of gene therapy transplants fibroblasts, which are capable of expressing IL-20 polypeptides, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., DNA, 7:219–25 (1988)), flanked by the long terminal repeats of the Moloney murine sarcoma virus, is digested with Eco RI and Hin dIII and subsequently treated with calf intestinal phosphatase. The linear vector is fractionated on agarose gel and purified, using glass beads.

The cDNA encoding IL-20 can be amplified using PCR primers which correspond to the 5' and 3' end sequences respectively as set forth in Example 1. Preferably, the 5' primer contains an Eco RI site and the 3' primer includes a Hin dIII site. Equal quantities of the Moloney murine sarcoma virus linear backbone and the amplified Eco RI and Hin dIII fragment are added together, in the presence of T4 DNA ligase. The resulting mixture is maintained under conditions appropriate for ligation of the two fragments. The ligation mixture is then used to transform bacteria HB 101, which are then plated onto agar containing kanamycin for the purpose of confirming that the vector contains properly inserted IL-20.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the IL-20 gene is then added to the media and the packaging cells transduced with the vector. The packaging cells now produce infectious viral particles containing the IL-20 gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether IL-20 protein is produced. The engineered fibroblasts are then transplanted onto the host, either alone or after having been grown to confluence on cytodex 3 microcarrier beads.

Example 28

Method of Treatment Using Gene Therapy—in Vivo

Another aspect of the present invention is using in vivo gene therapy methods to treat disorders, diseases and conditions. The gene therapy method relates to the introduction of naked nucleic acid (DNA, RNA, and antisense DNA or RNA) IL-20 sequences into an animal to increase or decrease the expression of the IL-20 polypeptide. The IL-20 polynucleotide may be operatively linked to a promoter or any other genetic elements necessary for the expression of the IL-20 polypeptide by the target tissue. Such gene therapy and delivery techniques and methods are known in the art, see, for example, WO90/11092, WO98/11779; U.S. Pat. Nos. 5,693,622, 5,705,151, 5,580,859; Tabata H. et al. (1997) Cardiovasc. Res. 35(3):470–479, Chao J et al. (1997) Pharmacol. Res. 35(6):517–522, Wolff J. A. (1997) Neuromuscul. Disord. 7(5):314–318, Schwartz B. et al. (1996) Gene Ther. 3(5):405–411, Tsurumi Y. et al. (1996) Circulation 94(12):3281–3290 (incorporated herein by reference).

The IL-20 polynucleotide constructs may be delivered by any method that delivers injectable materials to the cells of an animal, such as, injection into the interstitial space of tissues (heart, muscle, skin, lung, liver, intestine and the like). The IL-20 polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the IL-20 polynucleotides may also be delivered in liposome formulations (such as those taught in Feigner P. L. et al. (1995) Ann. NY Acad. Sci. 772:126–139 and Abdallah B. et al. (1995) Biol. Cell 85(1):1–7) which can be prepared by methods well known to those skilled in the art.

The IL-20 polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The IL-20 polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked IL-20 polynucleotide injection, an effective dosage amount of DNA or RNA will be in the range of from about 0.05 g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked IL-20 polynucleotide constructs can be delivered to arteries during angioplasty by the catheter used in the procedure.

The dose response effects of injected IL-20 polynucleotide in muscle in vivo is determined as follows. Suitable IL-20 template DNA for production of mRNA coding for IL-20 polypeptide is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The IL-20 template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 um cross-section of the individual quadriceps muscles is histochemically stained for IL-20 protein expression. A time course for IL-20 protein expression may be done in a similar fashion except that quadriceps from different mice are harvested at different times. Persistence of IL-20 DNA in muscle following injection may be determined by Southern blot analysis after preparing total cellular DNA and HIRT supernatants from injected and control mice. The results of the above experimentation in mice can be use to extrapolate proper dosages and other treatment parameters in humans and other animals using IL-20 naked DNA.

Example 29

IL-20-mediated Induction of IL-6 and IL-8 in Rheumatoid Arthritis Synoviocytes An analysis of the use of IL-20 to treat rheumatoid arthritis (RA) may be performed, for example, through the use of an adjuvant-induced arthritis (AIA) model in rats. AIA is a well-characterized and reproducible animal model of rheumatoid arthritis which is well-known to one of ordinary skill in the art (Pearson, *Ann. Rheum. Dis.* 15:379 (1956); Pearson & Wood, *Arthritis Rheum.* 2:440 (1959)). IL-20 is expected to affect angiogensis and/or endothelial cell proliferation required to sustain the invading pannus in bone and cartilage observed in this animal model of RA. Lewis and BB rats (available from Charles River Lab, Raleigh, N.C. and the University of Massachusetts Medical Center, Worcester, Mass.) are used as the common and responsive strains for adjuvant-induced arthritis in these experiments.

Initiation of the arthritic condition is induced by the intradermal injection of 0.1 ml adjuvant (5 mg/ml) into the base of the tail. Groups of 5 to 6 rats receive either 0.1 to 1.0 mg/kg IL-20 or vehicle intra-articularly 20 days after the injection of adjuvant. At this timepoint, acute inflammation reaches a maximal level and chronic pannus formation will have just begun. The effect of IL-20 on pannus formation is analyzed radiologically once each week after day 15 following adjuvant challenge essentially as described by Taurog and colleagues (*J. Exp. Med.* 162:962 (1985)). Briefly, rats are anesthetized with ether or chloral hydrate and positioned so that both hind limbs are X-rayed together. The X-ray films is examined blindly using a scoring system of 0–3 for periosteal reaction, bony erosions, joint space narrowing and destruction. When there is a significant amount of joint damage in vehicle-treated rats, the animals are sacrificed. At this point, the paws are evaluated histologically for the relative degree of tissue damage and for the therapeutic effect IL-20 has elicited on these joints. Finally, IL-20- and vehicle-treated animals undergo a clinical evaluation twice per week to assess hind paw volume using a plethysmometer system and body weight.

Alternatively, the use of IL-20 to treat RA may be examined by using a human RA synoviocyte analysis. The aim of this assay is to test the potential effect of IL-20 and its soluble receptor(s) as angonist or antagonist on synoviocytes activation and proliferation.

Rheumatoid synoviocytes are isolated from RA patients undergoing knee or wrist synovectomy and cultured in 150 $cm^2$ flasks. Nonadherent cells are removed and adherent cells are trypsinized at confluence and passaged. Synoviocytes used between passages 3 and 8 constitute a homogenous population of fibroblast-like cells. Synoviocytes are cultured in 96-well plates in a final volume of 200 $\mu$l of the medium. IL-20 polypeptides (or human IL-17 as a control) are added at different concentrations to the medium at the onset of the culture. Subsequently, cell-free supernatants are collected after 72 hr, and stored at −20° C. for further use in cytokine assays. Concentrations of IL-6 and IL-8 are measured by ELISA.

Results from analyses of the effect(s) of IL-20 polypeptide produced by the baculovirus methods described above in Example 4 indicate that IL-20 produced by baculoviral cultures induces a dose-dependent production of IL-6 and IL-8 in RA synoviocytes. In these analyses, IL-20 recombinant protein from baculovirus was tested on synoviocytes (RSFI, passage #6). ESP-2 was selected as endotoxin control for IL-20 at highest dose tested. Comparing with ESP-2 treatment, which showed minimal effect, IL-20 induced a dose-dependent production of both IL-6 and IL-8 at day 3, but had no observable effect on synoviocyte proliferation. The same batch of IL-20 protein was subsequently retested on synoviocytes (RSFI, passage #10) in comparison with recombinant human IL-17. A similar dose-dependent effect of IL-20 on the production of IL-6 and IL-8 was obtained. However, rhIL-17 induced a stronger response. Similar analyses using IL-20 produced from CHO cells by the methods described in Example 5, have shown no effects.

Thus, these results suggest that IL-20 may be useful to treat rheumatoid arthritis and other related immunoregulatory disorders and diseases.

Example 30

Effects of IL-20 on Smooth Muscle and Fibroblast Activation and/or Proliferation An analysis of the potential effects of IL-20 smooth muscle and fibroblast activation and/or proliferation are performed as follows. Human aortic smooth muscle cells (AoSMC) and normal human dermal fiblroblast (NHDF) and similar cell types are stimulated with IL-20, and cell proliferation and L-6 production are analyzed. IL-17 is used as a positive control. The ability of IL-20 to affect IL-17 activity may also be tested.

The effect(s) of supernatants from cultures of CHO cells expressing IL-20 (see Example 5) on the proliferation of normal human dermal fibroblasts (NHDF) and aortic smooth muscle cells (AoSMC) have been preliminarily examined as follows.

Human AoSMC or dermal fibroblast were seeded in wells of 96-well plates (2/cell type) and subsequently incubated in growth arrest media for 24 hours. Various IL-20 supernatants (s10, s16, and s22) or supernatant controls (CHO media and pC4 CHO supernatant) and assay controls (PDGF, Insulin, IL-1 and IL-17) were then added at various dilutions. The cells were incubated in a final volume of 200 ul for 3 days. Conditioned media aliquots were taken from AoSMC and NHDF cells treated with IL-20 supernatants (s10, s16, and s22); supernatant controls (CHO media and pC4 CHO supernatant); and assay controls (insulin, IL-1 and IL-17). Samples were then subjected to L-6 ELISA assay and signal detected using Au-congugated streptavidin and readings taken with a Wallac/Delfia fluorometer. IL6 concentration was determined by correlation with within-plate IL-6 standards.

Results from these experiments indicate that IL-20 supernatants s10 and s16 (at a 1/4 dilution) significantly stimulated IL-6 production in AoSMC above that of CHO media or pC4 controls. IL-20 s22 did not show any stimulatory activity for AoSMC. NHDF IL-6 production was not stimulated by any IL-20 supernatants. IL-17 control stimulated and IL-1α control greatly stimulated IL-6 production in both AoSMC and NHDF.

Partially purified IL-20 protein samples were tested (at approximate doses of 10, 100, and 1000 ng/ml) for stimulation of IL-6 production in AoSMC and NHDF. IL-17 (1, 10, and 100 ng/ml) was used as a positive control. Data were also collected for cotreatment of NHDF with IL-20 and IL-17, to test if IL-20 may have an additive or blocking effect on IL-17 induction of IL-6. IL-20 samples consisted of: (a) HS Pool I (P1) containing mostly slightly truncated form of IL-20 (18 kDa) and (b) HS Pool II (P2) containing mostly full length form of IL-20 (23 kDa).

Treatment with IL-20 P1 or P2 did not stimulate IL-6 production in either AoSMC or NHDF. Very slight co-stimulatory (IL-20 P1) or inhibitory (L-20 P2) effect on IL-17 induction of IL-6 in NHDF was detected.

Thus, these results suggest that IL-20 may be useful as a modulator of smooth muscle and fibroblast activation and/or proliferation.

Example 31

Analysis of IL-20 Receptor Candidates

IL-20 receptor candidates are screened for IL-20 binding using BIACORE technology which enables monitoring of binding events between two or more molecules, in real time, without the use of labels. BIACORE technology relies on the phenomenon of surface plasmon resonance (SPR) which occurs when surface plasmon waves are excited at a metal/liquid interface. Light is directed at, and reflected from, the side of the surface not in contact with sample, and SPR causes a reduction in the reflected light intensity at a specific combination of angle and wavelength. Biomolecular binding events cause changes in the refractive index at the surface layer, which are detected as changes in the SPR signal.

The conditioned culture supernatants from three IL-20 CHO clones (numbers 10, 16 and 22), as well as, IL-17 (purchased from R&D) were analyzed for binding to IL 17-like receptors. The data indicate that compared to the negative control conditioned media (pC4 vector alone) that all clones showed greater binding. The binding was approximately 115 RU for clones 16 and 22, ~65 RU for clone 10 and ~20 RU for pC4. This binding was greater than that found for IL-17 which was ~60 RU measured at 25 ug/mL. The exact concentration of IL-20 in the culture supernatants is not known but is estimated to be comparable to IL-17, i.e., ~25 ug/mL. This result suggests that the IL-17 receptor binds both ligands, and may even bind IL-20 better.

The binding of IL-20 and IL-17 to IL-17 receptor (IL 17R-Fc) and an IL-17 receptor homolog (IL-17RH-Fc (see copending U.S. patent application Ser. No. 09/154,219)) after immobilization of the receptor on a BIAcore flow cell. Two CHO cell IL-20 preparations were first analyzed as they contain different N-terminal forms of the protein. IL-17 (R&D) ligand was also analyzed. The results indicate that IL-20 predominately bound to the IL-17RH and to a much lesser extent to IL-17R. The dissociation of IL-20 from the IL-17RH appeared to be biphasic for both batches which might be due to the presence different N-terminally truncated forms of the protein present in both batches. In contrast, IL-17 bound almost exclusively to the IL-17R which little or no binding to IL-17RH.

Thus, these results suggest that IL-20 interacts with the IL-17 receptor and to the IL-17-receptor-like protein described above. As a result, IL-20 may be useful to modulate the receptor activation pathways in which these receptors are involved. lL-20 polypeptides of the invention may be used as an agonist or antagonist for binding of either the same or other IL-20 polypeptides of the invention and/or other related or unrelated polypeptides which interact with these receptor molecules, e.g., IL-17. IL-20 polypeptides of the invention may thus be useful in the diagnosis and/or treatment of immune disorders involving the IL-17 and IL-17RLP molecules as known in the art and as described above.

It will be clear that the invention may be practiced otherwise than as particularly described in the foregoing description and examples. Numerous modifications and variations of the present invention are possible in light of the above teachings and, therefore, are within the scope of the appended claims. One of skill in the art will immediately recognize that any of the Examples set forth above may also be practiced using any of the IL-20 molecules and sequences of the invention, particularly those set forth in SEQ ID NO:15, SEQ ID NO:28, and SEQ ID NO:29, by designing primer sequences and the like accordingly.

The entire disclosure of all publications (including patents, patent applications, journal articles, laboratory manuals, books, or other documents) cited herein are hereby incorporated by reference.

Further, the Sequence Listing submitted herewith, and the Sequence Listing submitted with U.S. patent application Ser. No. 09/115,832, filed on Jul. 15, 1998, the Sequence the Sequence Listing submitted with U.S. Provisional Application Serial No. 60/052,870, filed on Jul. 16, 1997, the Sequence Listing submitted with U.S. Provisional Application Serial No. 60/060,140, filed on Sep. 26, 1997, and the Sequence Listing submitted with U.S. Provisional Application Serial No. 60/055,952, filed on Aug. 18, 1997, in both computer and paper forms are hereby incorporated by reference in their entireties.

What is claimed is:

1. An isolated polypeptide consisting of a member selected from the group consisting of:

(a) a polypeptide set forth as amino acid residues −20 to 160 of SEQ ID NO:2;

(b) a polypeptide set forth as amino acid residues −19 to 160 of SEQ ID NO:2;

(c) a polypeptide set forth as amino acid residues 1 to 160 of SEQ ID NO:2;

(d) a polypeptide set forth as amino acid residues 2 to 160 of SEQ ID NO:2;

(e) a polypeptide set forth as amino acid residues 3 to 160 of SEQ ID NO:2;

(f) a polypeptide set forth as amino acid residues 4 to 160 of SEQ ID NO:2;

(g) a polypeptide set forth as amino acid residues 5 to 160 of SEQ ID NO:2;

(h) a polypeptide set forth as amino acid residues 6 to 160 of SEQ ID NO:2;

(i) a polypeptide set forth as amino acid residues 7 to 160 of SEQ ID NO:2;

(j) a polypeptide set forth as amino acid residues 8 to 160 of SEQ ID NO:2;

(k) a polypeptide set forth as amino acid residues 9 to 160 of SEQ ID NO:2;

(l) a polypeptide set forth as amino acid residues 10 to 160 of SEQ ID NO:2;

(m) a polypeptide having the amino acid sequence encoded by the cDNA clone contained in ATCC Deposit No. 209232;

(n) a polypeptide, excluding the N-terminal methionine residue, having the amino acid sequence encoded by the cDNA clone contained in ATCC Deposit No. 209232; and (o) a polypeptide having the amino acid sequence of a mature polypeptide encoded by the cDNA clone contained in ATCC Deposit No. 209232.

2. The isolated polypeptide of claim 1, wherein said polypeptide is (a).

3. The isolated polypeptide of claim 1, wherein said polypeptide is (b).

4. The isolated polypeptide of claim 1, wherein said polypeptide is (c).

5. The isolated polypeptide of claim 1, wherein said polypeptide is (d).

6. The isolated polypeptide of claim 1, wherein said polypeptide is (e).

7. The isolated polypeptide of claim 1, wherein said polypeptide is (f).

8. The isolated polypeptide of claim 1, wherein said polypeptide is (g).

9. The isolated polypeptide of claim 1, wherein said polypeptide is (h).

10. The isolated polypeptide of claim 1, wherein said polypeptide is (i).

11. The isolated polypeptide of claim 1, wherein said polypeptide is (j).

12. The isolated polypeptide of claim 1, wherein said polypeptide is (k).

13. The isolated polypeptide of claim 1, wherein said polypeptide is (l).

14. The isolated polypeptide of claim 1, wherein said polypeptide is (m).

15. The isolated polypeptide of claim 1, wherein said polypeptide is (n).

16. The isolated polypeptide of claim 1, wherein said polypeptide is (o).

17. The isolated polypeptide of claim 1, linked to a heterologous polypeptide.

18. A composition comprising the polypeptide of claim 1 in a pharmaceutically acceptable carrier.

* * * * *